United States Patent [19]

Harrison et al.

[11] Patent Number: 5,474,998
[45] Date of Patent: Dec. 12, 1995

[54] ARTHROPODICIDAL PYRAZOLINES, PYRAZOLIDINES AND HYDRAZINES

[75] Inventors: Charles R. Harrison, Newark; Renee M. Lett, Wilmington; Stephen F. McCann, Bear; Rafael Shapiro, Wilmington; Thomas M. Stevenson, Newark, all of Del.

[73] Assignee: E. I. Du Pont de Nemours and Company, Wilmington, Del.

[21] Appl. No.: 971,974

[22] PCT Filed: Aug. 1, 1991

[86] PCT No.: PCT/US91/05334

§ 371 Date: Feb. 16, 1993

§ 102(e) Date: Feb. 16, 1993

[87] PCT Pub. No.: WO92/03421

PCT Pub. Date: Mar. 5, 1992

Related U.S. Application Data

[60] which is a continuation-in-part of Ser. No. 569,044, Aug. 17, 1990, abandoned, which is a continuation-in-part of Ser. No. 573,954, Aug. 27, 1990, abandoned, and a continuation-in-part of Ser. No. 595,151, Oct. 9, 1990, abandoned.

[51] Int. Cl.$^6$ .................... C07D 401/04; C07D 403/04; A01N 43/56; A01N 43/56

[52] U.S. Cl. .................. 514/254; 548/311.7; 548/356.5; 548/358.1; 548/358.5; 546/256; 546/271; 544/238; 544/331; 544/298; 544/405; 548/359.1; 514/269; 514/256; 514/333; 514/338; 514/397; 514/406; 514/407

[58] Field of Search ................ 548/359.1, 359.5, 548/311.7, 358.5; 514/406, 254, 269, 256, 397; 546/256; 544/238, 405

[56] References Cited

FOREIGN PATENT DOCUMENTS

| 286346 | 10/1988 | European Pat. Off. . |
| 305201 | 4/1990 | European Pat. Off. . |

*Primary Examiner*—John M. Ford

[57] ABSTRACT

Arthropodicidal pyrazoline, pyrazolidine and hydrazine compounds, including all their geometric and stereoisomers, agriculturally suitable salts thereof and compositions containing them; and a method for controlling arthropods employing said compounds which are:

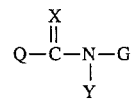

and

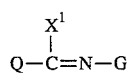

wherein Q, X, X$^1$, Y and G are as defined in the text.

8 Claims, No Drawings

ARTHROPODICIDAL PYRAZOLINES, PYRAZOLIDINES AND HYDRAZINES

RELATIONSHIP TO OTHER APPLICATIONS

This application is a Sec. 371 application of PCT/US91/05334, filed Aug. 1, 1991, which is a continuation-in-part of U.S. Ser. No. 07/569,044, filed Aug. 17, 1990; which is a continuation-in-part of U.S. Ser. No. 07/573,954, filed Aug. 27, 1990; and U.S. Ser. No. 07/595,151, filed Oct. 9, 1990, all of which are abandoned.

1. Field of the Invention

This invention concerns arthropodicidal pyrazolines, pyrazolidines and hydrazines, compositions containing them, and a method for their use to control arthropods.

2. State of the Art

WO 88/07,994 and EPA 330,678 disclose insecticidal pyrazolines. U.S. Pat. No. 4,547,524 discloses benzoyl hydrazone derivatives as insecticides. WO 88/00197 discloses substituted semicarbazones derived from chromanones and thiochromanones as insecticide intermediates. EP-3,913, EP 26,040 and EP 254,461 disclose substituted hydrazone insecticides. *J. Org. Chem.*, 1987, 52, 2277 discloses pyrazolines as does Chem Soc., Jap., 55, 2450 (1982).

*J. Ind. Chem. Soc.*, 37, pages 443 to 450 (1960) discloses a compound of the formula:

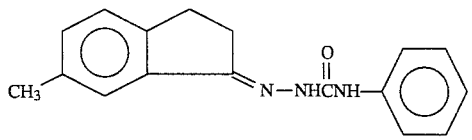

but no utility therefor.

Vaughn, *J. Org. Chem.*, 20 (1955), pages 1619 to 1626, discloses 1,5-diphenyl-2-pyrazoline-3-carboxamide. No utility is given for the disclosed compound which, in any event, does not suggest a compound of the instant invention.

Harhash et al., *J. Heterocyclic Chem.*, 21 (1984), at page 1013, discloses the preparation of five pyrazoline compounds, none of which is disclosed in the instant application. No utility is given for any of said compounds:

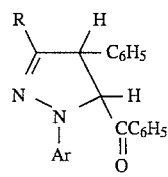

where R/Ar are $C_6H_5/C_6H_5$; $CO_2C_2H_5/C_6H_5$; $C(O)NHC_6H_5H_5$; $CH=CHC_6H_5/C_6H_5$; and $CH_3/4—NO_2—C_6H_4$.

U.S. Pat. No. 4,070,365 discloses insecticidal compounds of the formula

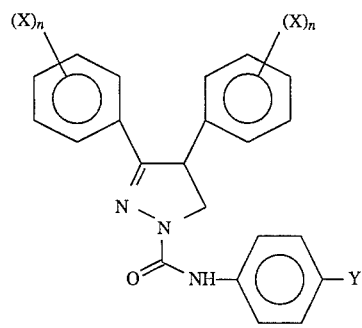

wherein X is halogen; and Y is halogen, $NO_2$ or alkyl.

EP 153,127 discloses insecticidal compounds of the formula

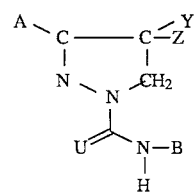

wherein

A is unsubstituted or substituted phenyl; B is unsubstituted or substituted phenyl; U is O, S or NR; Y is alkyl, unsubstituted or substituted phenyl, or C(X)G; Z is H, cycloalkyl, unsubstituted or substituted phenyl $R^4$—Q; X is O or S; and G and $R^4$—Q are broadly defined.

SUMMARY OF THE INVENTION

The invention pertains to compounds of Formula I and II, including all geometric and stereoisomers, agriculturally suitable salts thereof, agricultural compositions containing them and their use for the control of arthropods in both agronomic and non-agronomic uses. The compounds are:

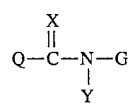

and

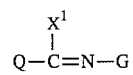

wherein:

Q is selected from the group

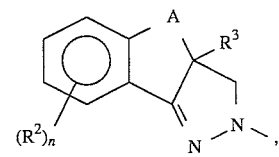

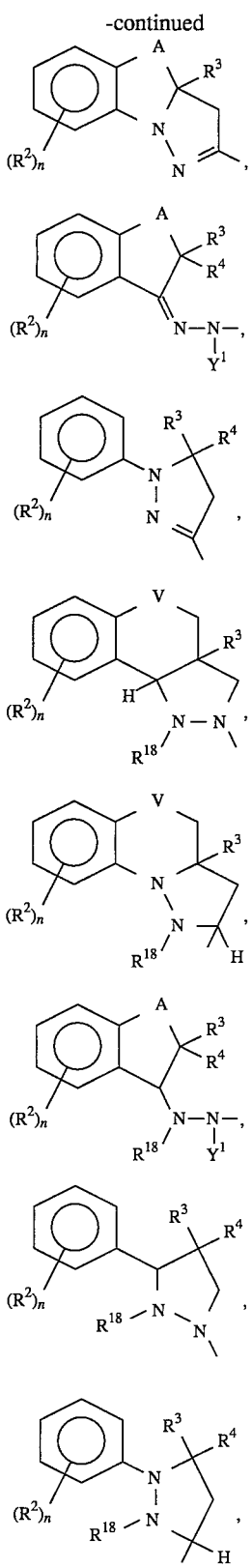
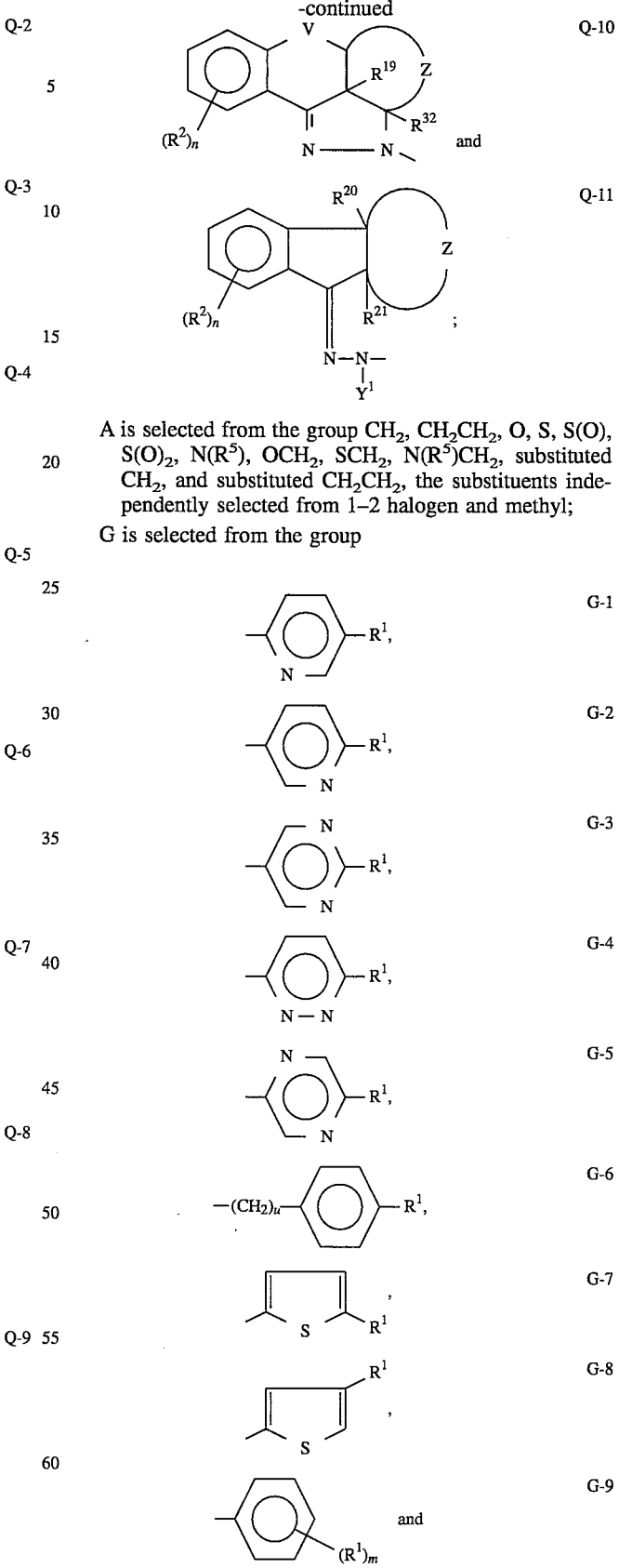
A is selected from the group $CH_2$, $CH_2CH_2$, O, S, S(O), $S(O)_2$, $N(R^5)$, $OCH_2$, $SCH_2$, $N(R^5)CH_2$, substituted $CH_2$, and substituted $CH_2CH_2$, the substituents independently selected from 1–2 halogen and methyl;
G is selected from the group -continued

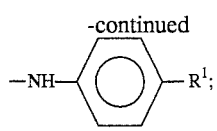
G-10

X is selected from the group O, S and N—$X^2$;

$X^1$ is selected from the group Cl, Br, $OR^6$, $SR^6$ and $N(R^6)R^7$;

$X^2$ is selected from the group $R^6$, OH, $OR^6$, CN, $SO_2R^6$, $SO_2Ph$, $OC(O)N(R^7)R^8$, $OC(O)OC_1$—$C_6$ alkyl, $N(R^7)R^8$ and phenyl optionally substituted with $R^9$;

Y and $Y^1$ are independently selected from the group H, $C_1$–$C_6$ alkyl, benzyl, $C_2$–$C_6$ alkoxyalkyl, CHO, $C_2$–$C_6$ alkylcarbonyl, $C_2$–$C_6$ alkoxycarbonyl, $C_2$–$C_6$ haloalkylcarbonyl, $C_1$–$C_6$ alkylthio, $C_1$–$C_6$ haloalkylthio, phenylthio, $R^{10}OC(O)N(R^{11})S$— and $R^{12}(R^{13})NS$—;

$R^1$, $R^2$ and $R^{14}$ are independently selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, $N_3$, SCN, $NO_2$, $OR^{15}$, $SR^{15}$, $S(O)R^{15}$, $S(O)_2R^{15}$, $OC(O)R^{15}$, $OS(O)_2R_{15}$, $CO_2R^{15}$, $C(O)R^{15}$, $C(O)N(R^{15})R^{16}$, $SO_2N(R^{15})R^{16}$, $N(R^{15})R^{16}$, $N(R^{16})C(O)R^{15}$, $OC(O)NHR^{15}$, $N(R^{16})C(O)NHR^{15}$, $N(R^{16})SO_2R^{15}$, phenyl optionally substituted with 1 to 3 substituents independently selected from W and benzyl optionally substituted with 1 to 3 substituents independently selected from W; or when m, n or p is 2, $(R^1)_2$ can be taken together, or $(R^2)_2$ can be taken together or $(R^{14})_2$ can be taken together as —$OCH_2O$, —$OCF_2O$, $OCH_2CH_2O$, $CF_2CF_2O$, —$CH_2C(CH_3)_2O$— or —$OCF_2CF_2O$—to form a cyclic bridge between adjacent atoms on the same ring;

$R^3$ is selected from the group $R^a$, $R^b$ and J;

$R^a$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $OR^{35}$, $C_2$–$C_6$ alkoxyalkyl, $C_2$–$C_6$ cyanoalkyl, $C_3$–$C_8$ alkoxycarbonylalkyl, $CO_2R^{15}$, $C(O)R^{15}$, $C(O)N(R^{15})R^{16}$, $C(S)N(R^{15})R^{16}$, $C(S)R^{15}$, $C(S)SR^{15}$, phenyl, phenyl substituted with $(R^{14})p$, benzyl and benzyl substituted with 1 to 3 substituents independently selected from W;

$R^b$ is selected from the group CN, $N_3$, $NO_2$, halogen, $N(R^{22})R^{23}$, $C(R^{33})$=N—O—$R^{34}$, $C_2$–$C_6$ epoxyalkyl optionally substituted with a group selected from $C_1$–$C_3$ alkyl, phenyl optionally substituted with W, $C(O)R^{24}$, $Si(R^{28})(R^{29})$ $R^{30}$, $SR^{27}$, $S(O)R^{27}$, $SO_2R^{27}$ and —$P(O)(OR^{27})_2$, $CO_2R^{24}$; or $R^b$ is $C_1$–$C_6$ alkyl substituted with a group selected from $C(O)N(R^{25})R^{26}$, $C(O)R^{25}$, $SR^{27}$, $S(O)R^{27}$, $SO_2R^{27}$, SCN, $C_1$–$C_2$ haloalkoxy, $Si(R^{28})(R^{29})R^{30}$, $N(R^{22})R^{23}$, $NO_2$, $OC(O)R^{25}$, $Si(R^{28})(R^{29})R^{30}$, —$P(O)(OR^{27})_2$ and J;

J is selected from the group consisting of saturated, partially saturated and aromatic 5- or 6-membered substituted or unsubstituted heterocyclic rings, bonded through carbon or nitrogen, containing 1–4 heteroatoms independently selected from the group consisting of 0–2 oxygen, 0–2 sulfur and 0–4 nitrogen and optionally containing one carbonyl wherein the substituent groups are selected from W;

$R^4$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ cyanoalkyl, phenyl optionally substituted with $(R^{14})_p$ and benzyl optionally substituted with 1 to 3 substituents independently selected from W;

$R^5$ is selected from the group H, $C_1$–$C_4$ alkyl, $C_1$–$C_4$ haloalkyl, $C_2$–$C_4$ alkenyl, $C_2$–$C_4$ haloalkenyl, $SR^{15}$, $S(O)R^{15}$, $S(O)_2R^{15}$, $C(O)R^{15}$, $CO_2R^{15}$, $C(O)N(R^{15})R^{17}$, $C(S)N(R^{15})R^{17}$, $C(S)R^{15}$, $C(S)OR^{15}$, $P(O)(OR^{15})_2$, $P(S)(OR^{15})_2$, $P(O)(R^{17})OR^{15}$, $P(O)(R^{15})(SR^{17})$, and optionally substituted phenyl and optionally substituted benzyl wherein the substituent(s) are selected from W;

$R^6$ is selected from the group $C_1$–$C_3$ alkyl, benzyl optionally substituted with $R^9$, $C_2$–$_{C4}$ alkenyl, $C_2$–$C_4$ alkynyl, $C_1$–$C_3$ haloalkyl, $C_2$–$C_4$ haloalkenyl, $C_3$–$C_6$ cycloalkyl and $C_1$–$C_3$ alkyl substituted with $OCH_3$, $OCH_2CH_3$, $NO_2$, CN, $CO_2CH_3$, $CO_2CH_2CH_3$, $SCH_3$ or $SCH_2CH_3$;

$R^7$ is selected from the group H, $C_1$–$C_4$ alkyl, $C_1$–$C_4$ haloalkyl, $C_2$–$C_4$ alkoxycarbonyl, optionally substituted phenyl and optionally substituted pyridinyl wherein the substituent(s) are selected from $R^9$; or $R^6$ and $R^7$ when attached to the same atom can be taken together to form —$(CH_2)_4$—, —$(CH_2)_5$— or —$CH_2CH_2OCH_2CH_2$— each of which is optionally substituted with 1 or 2 $CH_3$ groups;

$R^8$ is selected from the group H and $C_1$–$C_4$ alkyl; or $R^7$ and $R^8$ can be taken together to form —$(CH_2)_4$—, —$(CH_2)_5$— or —$CH_2CH_2OCH_2CH_2$— each of which is optionally substituted with 1 or 2 $CH_3$ groups;

$R^9$ is selected from the group halogen, CN, $C_1$–$C_3$ haloalkyl and $C_1$–$C_3$ haloalkoxy;

$R^{10}$ is $C_1$–$C_6$ alkyl;

$R^{11}$ is $C_1$–$C_4$ alkyl;

$R^{12}$ and $R^{13}$ are independently $C_1$–$C_4$ alkyl; or $R^{12}$ and $R^{13}$ when attached to the same atom, can be taken together as —$CH_2CH_2CH_2CH_2CH_2$— or —$CH_2CH_2OCH_2CH_2$—;

$R^{15}$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, optionally substituted phenyl and optionally substituted benzyl wherein the substituent(s) are 1 to 3 substituents independently selected from W; wherein $R^{15}$ is other than H when: (i) $R^1$, $R^2$, or $R^{14}$ is $S(O)R^{15}$, $SO_2R^{15}$, $OC(O)R^{15}$ or $OS(O)_2R^{15}$, (ii) $R^a$ is $C(S)R^{15}$ or $C(S)SR^{15}$, or (iii) $R^5$ is not $C(O)R^{15}$, $C(O)N(R^{15})R^{17}$ or $C(S)N(R^{15})R^{17}$;

$R^{16}$ is selected from the group H and $C_1$–$C_4$ alkyl; or $R^{15}$ and $R^{16}$, when attached to the same atom, can be taken together as —$(CH_2)_4$—, —$(CH_2)_5$—, or —$CH_2CH_2OCH_2CH_2$—;

$R^{17}$ is selected from the group H, $C_1$–$C_4$ alkyl, $C_2$–$C_4$ alkenyl and $C_2$–$C_4$ alkynyl;

$R^{18}$ is selected from the group H, $C_1$–$C_4$ alkyl, $C_1$–$C_4$ haloalkyl, $C_2$–$C_4$ alkylcarbonyl, $C_2$–$C_4$ haloalkylcarbonyl, $C_2$–$C_4$ alkoxycarbonyl, $C_2$–$C_4$ haloalkoxycarbonyl, $C_2$–$C_5$ alkylaminocarbonyl, $C_3$–$C_6$ cycloalkyl, $C_3$–$C_6$ halocycloalkyl, $C_4$–$C_7$ alkylcycloalkyl, $C_4$–$C_7$ haloalkylcycloalkyl, $C_1$–$C_4$ alkylsulfonyl, $C_1$–$C_4$ haloalkylsulfonyl and $SO_2Ph$ optionally substituted with Cl, or $CH_3$;

$R^{19}$, $R^{20}$ and $R^{21}$ are independently selected from the group H, $C_1$–$C_3$ alkyl, $CO_2R^{15,}$ phenyl and phenyl substituted by W;

$R^{22}$ is selected from the group H, $C((O)C_1$–$C_6$ alkyl, $CO_2C_1$–$C_6$ alkyl, optionally substituted $C_1$–$C_4$ alkyl, optionally substituted $C_2$–$C_4$ alkenyl, and optionally substituted $C_2$–$C_4$ alkynyl, the substituents selected from $C_1$–$C_2$ alkoxy, CN, $C(O)R^{31}$ and $C(O)_2R^{27}$;

$R^{23}$ is selected from the group H, $C_1$–$C_3$ alkyl, phenyl, phenyl substituted with W, benzyl and benzyl substituted with W;

$R^{24}$ is selected from the group H, $C_1$–$C_4$ alkyl $C_2$–$C_4$ alkenyl and $C_2$–$C_4$ alkynyl;

$R^{25}$ and $R^{26}$ are independently selected from the group H and $C_1$–$C_2$ alkyl;

$R^{27}$ is selected from the group $C_1$–$C_3$ alkyl, phenyl and phenyl substituted with W;

$R^{28}$ is $C_1$–$C_3$ alkyl;

$R^{29}$ is $C_1$–$C_3$ alkyl;

$R^{30}$ is selected from the group $C_1$–$C_3$ alkyl, phenyl and phenyl substituted with W;

$R^{31}$ is selected from the group H, $C_1$–$C_3$ alkyl, phenyl and phenyl substituted by W;

$R^{32}$ is selected from the group H, $CH_3$ and $CO_2CH_3$ $R^{33}$ is selected from the group H, Cl, $C_1$–$C_4$ alkyl, $C_1$–$C_2$ alkoxy, $C_1$–$C_2$ thioalkyl and CN;

$R^{34}$ is selected from the group H, $C_1$–$C_4$ alkyl, $C_2$–$C_3$ alkylcarbonyl and $C_2$–$C_3$ alkoxycarbonyl;

$R^{35}$ is selected from the group H, $C_1$–$C_4$ alkyl, $C_2$–$C_4$ alkenyl, $C_2$–$C_4$ alkynyl, $C_2$–$C_4$ alkylcarbonyl, $C_2$–$C_4$ alkoxycarbonyl, $C_2$–$C_4$ alkylaminocarbonyl, $C_2$–$C_4$ dialkylaminocarbonyl, and $C_1$–$C_4$ alkylsulfonyl;

V is selected from the group O, S, $N(R^5)$, $CH_2$ and $CH_2$ substituted with 1–2 $CH_3$;

W is selected from the group halogen, CN, $NO_2$, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, $C_1$–$C_2$ alkylsulfonyl and $C_1$–$C_2$ haloalkylsulfonyl;

Z is selected from the group $(CH_2)_q$, —$CH_2OCH_2$—, —$CH_2SCH_2$— and —$CH_2NHCH_2$—, where said groups can be optionally substituted with 1–2 $CH_3$;

m is 1 to 3;

n is 1 to 3;

p is 1 to 3;

q is 2 to 4;

u is 1 or 2;

provided that (i) when Q is Q—3, $R^3$ is other than CN, $N(R^{22})R^{23}$, $SR^{27}$, $S(O)R^{27}$ or $SO_2R^{27}$, (ii) when Q is Q—4, $R^3$ is other than CN or J, and (iii) when G is G—9, $R^3$ is other than $R^a$.

Exemplary values of J include

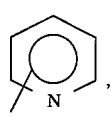  J-1

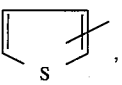  J-2

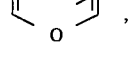  J-3

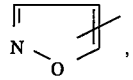  J-4

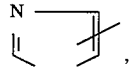  J-5

  J-6

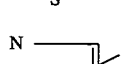  J-7

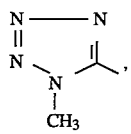  J-8

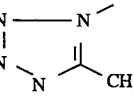  J-9

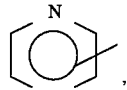  J-10

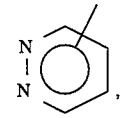  J-11

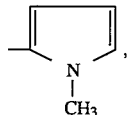  J-12

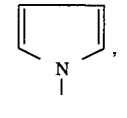  J-13

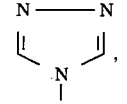  J-14

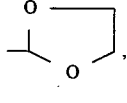  J-15

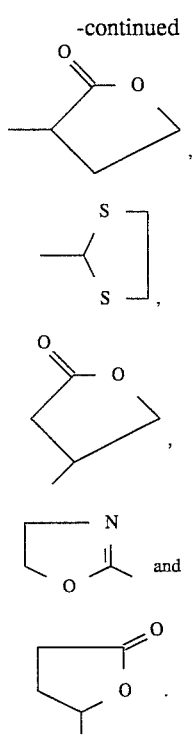

Preferred Compounds A are compounds of Formulae I and II wherein:

$R^1$ is selected from the group H, halogen, CN, SCN, $NO_2$, $OR^{15}$, $SR^{15}$, $SO_2R^{15}$, $CO_2R^{15}$, $C(O)R^{15}$, $C_1$–$C_6$ alkyl, $C_1$–$C_6$ haloalkyl, $C_2$–$C_6$ haloalkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, phenyl optionally substituted with 1 to 3 substituents independently selected from W, and benzyl optionally substituted with 1 to 3 substituents independently selected from W;

$R^2$ and $R^{14}$ are independently selected form the group H, halogen, CN, SCN, $NO_2$, $OR^{15}$, $SR^{15}$, $S(O)_2R^{15}$, $OC(O)R^{15}$, $OS(O)_2R^{15}$, $CO_2R^{15}$, $C(O)R^{15}$, $C(O)N(R^{15})R^{16}$, $SO_2N(R^{15})R^{16}$, $N(R^{15})R^{16}$, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, phenyl optionally substituted with 1 to 3 substituents independently selected from W, and benzyl optionally substituted with 1 to 3 substituents independently selected from W;

$R^3$ is selected from the group $R^a$, $R^b$ and J;

$R^a$ is selected form the group H, $C_1$–$C_4$ alkyl, $C_3$–$C_4$ alkoxycarbonylalkyl, $CO_2R^{15}$, $C(O)R^{15}$, phenyl and phenyl substituted by $(R^{14})_p$;

$R^b$ is selected from the group CN, $C(R^{33})$=$NOR^{34}$, $C_2$–$C_6$ epoxyalkyl and $SR^{27}$; or $R^b$ is $C_1$–$C_4$ alkyl substituted with a group selected from $C(O)R^{25}$, $SR^{27}$, $S(O)R^{27}$, $SO_2R^{27}$, $C_1$–$C_2$ haloalkoxy and $Si(R^{28})(R^{29})R^{30}$;

$R^4$ is selected from the group H, $C_1$–$C_3$ alkyl, $C_2$–$C_4$ alkenyl and $C_2$–$C_4$ alkynyl;

$R^{18}$ is H;

X is O;

$X^1$ is selected from the group Cl, $OR^6$, $SR^6$ and $N(CH_3)_2$;

$X^2$ is selected from the group $R^6$, $OR^6$ and $N(CH_3)_2$;

A is selected from the group O, $CH_2$, $OCH_2$, S, $CH_2CH_2$, $SCH_2$, $N(R^5)CH_2$ and $N(R^5)$;

$R^5$ is selected from the group H, $C_1$–$C_4$ alkyl, $S(O)_2R^{15}$, $CO_2R^{15}$ and $CONHR^{15}$;

$R^{15}$ is selected from the group $C_1$–$C_4$ alkyl, $C_1$–$C_2$ haloalkyl, $C_3$–$C_4$ alkenyl and propargyl;

$R^{16}$ is selected from H and $CH_3$;

$R^{27}$ is $C_1$–$C_3$ alkyl;

$R^{33}$ is selected from the group H and $CH_3$;

$R^{34}$ is selected from the group H and $C_1$–$C_3$ alkyl;

V is selected from the group O, $N(R^5)$ and $CH_2$;

W is selected from the group Cl, F, Br, CN, $CF_3$, $C_1$–$C_2$ alkyl, $C_1$–$C_2$ alkoxy, $OCF_2H$, $OCF_3$ and $NO_2$;

Y is selected from the group H, $CH_3$, $C(O)CH_3$ and $CO_2CH_3$;

Z is —$CH_2CH_2CH_2$— or —$CH_2CH_2$—;

m is 1 or 2;

n is 1 or 2; and p is 1.

Preferred Compounds B are Compounds A wherein G is selected from the group G-2, G-3, G-7 and G-9.

Preferred Compounds C are Compounds B wherein J is selected from the group J-1, J-2, J-8, J-9 and J-16.

Preferred Compounds D are Compounds C of Formula I wherein Q is Q-1 and A is selected from the group $CH_2$, $OCH_2$, $CH_2CH_2$, $SCH_2$ and $N(R^5)CH_2$.

Preferred Compounds E are Compounds C of Formula I wherein is Q-2 and A is selected from the group $CH_2$, $OCH_2$, $CH_2CH_2$, $SCH_2$ and $N(R^5)CH_2$.

Preferred Compounds F are Compounds C of Formula I wherein Q is Q-3 and A is selected from the group $CH_2$, $OCH_2$, $CH_2CH_2$, $SCH_2$ and $N(R^5)CH_2$.

Preferred Compounds G are Compounds C of Formula I wherein Q is Q-4 and A is selected from the group $CH_2$, $OCH_2$, $CH_2CH_2$, $SCH_2$ and $N(R^5)CH_2$.

In the above recitations, the term "alkyl", used either alone or in compound words such as "alkylthio" or "haloalkyl", denotes straight chain or branched alkyl, e.g., methyl, ethyl, n-propyl, isopropyl or the different butyl, pentyl, hexyl isomers.

Alkoxy denotes methoxy, ethoxy, n-propyloxy, isopropyloxy and the different butoxy, pentoxy or hexyloxy isomers.

Alkenyl denotes straight chain or branched alkenes, e.g., vinyl, 1-propenyl, 2-propenyl, 3-propenyl and the different butenyl, pentenyl and hexenyl isomers.

Alkynyl denotes straight chain or branched alkynes, e.g., ethynyl, 1-propynyl, 3-propynyl and the different butynyl, pentynyl and hexynyl isomers.

Alkylthio denotes methylthio, ethylthio and the different propylthio, butylthio, pentylthio and hexylthio isomers.

Alkylsulfinyl, alkylsulfonyl, alkylamino, etc., are defined analogously to the above examples.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$. The terms "halocycloalkyl", "Haloalkenyl" and "haloalkynyl" are defined analogously to the term "haloalkyl".

The total number of carbon atoms in a substituent group is indicated by the "$C_i$–$C_j$" prefix where i and j are numbers from 1 to 8. For example, $C_1$–$C_3$ alkylsulfonyl designates methylsulfonyl through propylsulfonyl; $C_2$ alkoxyalkoxy designates $OCH_2OCH_3$; $C_4$ alkoxyalkoxy designates the various isomers of an alkoxy group substituted with a second alkoxy group containing a total of 4 carbon atoms, examples including $OCH_2OCH_2CH_2CH_3$ and $OCH_2CH_2OCH_2CH_3$; $C_2$ cyanoalkyl designates $CH_2CN$ and $C_3$ cyanoalkyl designates $CH_2CH_2CN$ and $CH(CN)CH_3$; $C_2$ alkylcarbonyl would designates $C(O)CH_3$ and $C_4$ alkylcarbonyl includes $C(O)CH_2CH_2CH_3$ and $C(O)CH(CH_3)_2$; and as a final example, $C_3$ alkoxycarbonylalkyl designates $CH_2CO_2CH_3$ and $C_4$ alkoxycarbonylalkyl includes $CH_2CH_2CO_2CH_3$, $CH_2CO_2CH_2CH_3$ and $CH(CH_3)CO_2CH_3$.

DETAILS OF THE INVENTION

Compounds of Formula I where Q is Q-1

Preparation of certain pyrazoline compounds where Q is Q-1 and A is an alkylene bridge is reported in WO-88/07,994. Deprotonation of compounds of Formula I where $R^3$ is equal to H, with base and reaction with suitable electrophilic reagents yields compounds of Formula I, where $R^3$ is equal to E (Scheme 1).

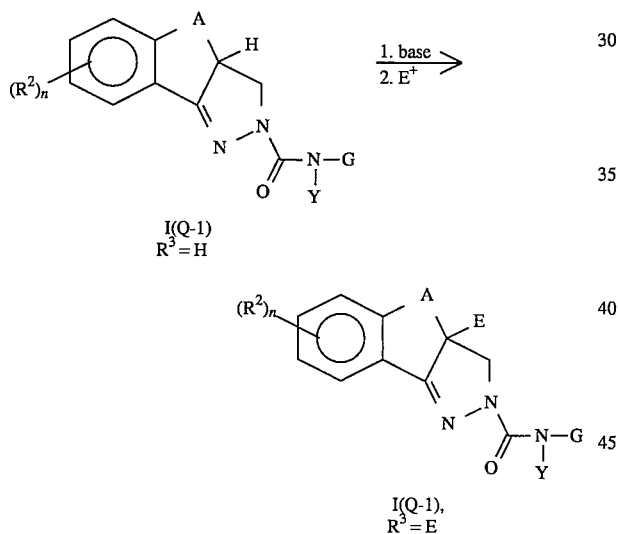

The electrophilic reagent can be chosen to give the preferred $R^3$ groups of this invention. For example, p-toluenesulfonyl cyanide can be used to prepare compounds of Formula I where $R^3$ is equal to cyano; see Collum et al. (*Tetrahedron Lett*, 22, 5011). Methyl chloroformate can be used to prepare compounds of Formula I where $R^3$ is equal to carbomethoxy. Dimethylformamide can be used to prepare compounds of Formula I where $R^3$ is formyl (HCO). Acid chlorides can be used to prepare compounds of Formula I where $R^3$ is acyl (C(O)alkyl).

The formyl and acyl derivatives can be further reacted with amine derivatives such as hydroxy- or alkoxy-amines to yield compounds of this invention as depicted in Scheme 2 (reaction a). The methyl ester derivative can be further reacted by hydrolysis to the acid, conversion of the acid to an acid chloride, reaction of the acid chloride with trimethylsilylazide, Curtius rearrangement of the acyl azide to an isocyanate, and finally reaction of the isocyanate with methanol to yield the methyl carbamate (Scheme 2, reaction b). The intermediate acid chloride can alternatively be reacted to provide various other ester derivatives (Scheme 2, reaction c).

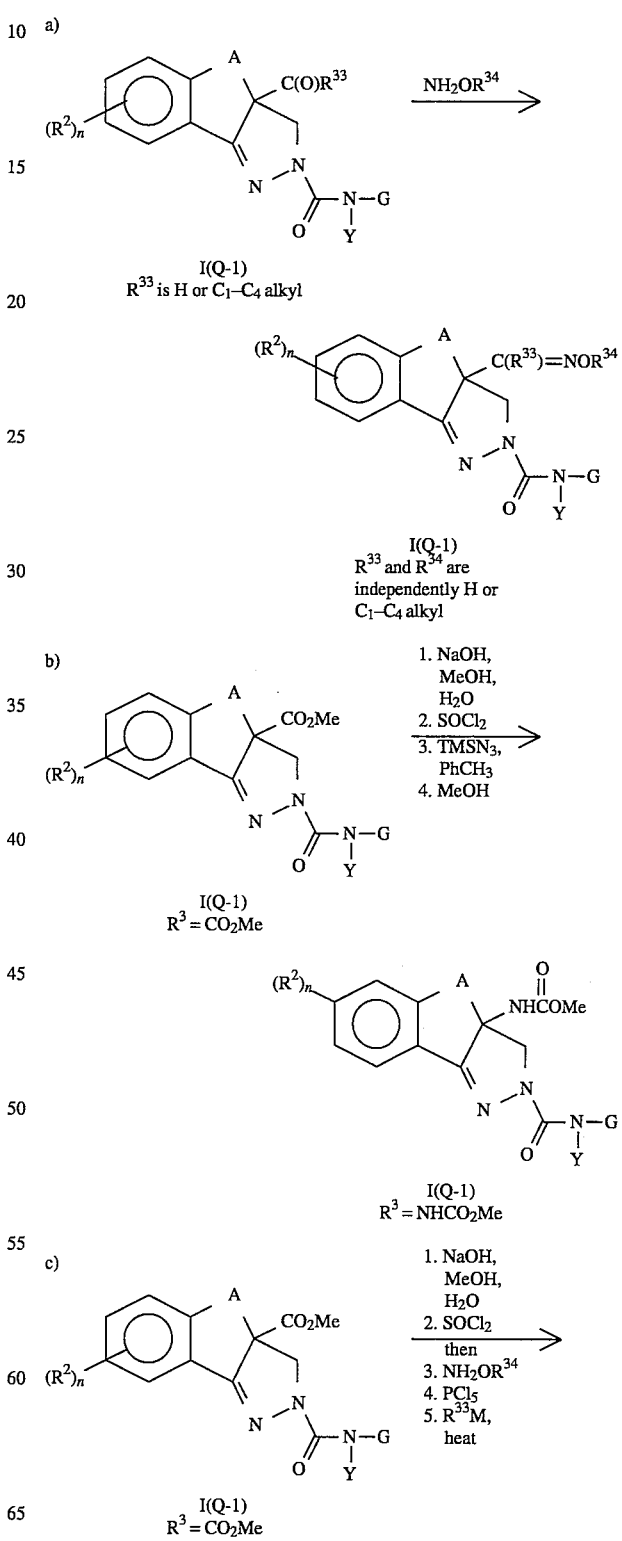

-continued
Scheme 2

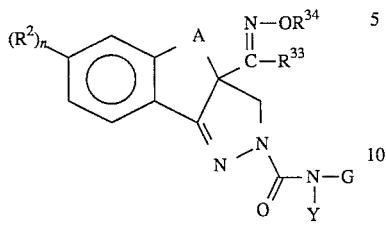

I(Q-1)
$R^{34}$ is $C_1$–$C_4$ alkyl
$R^{33}$ is $C_1$–$C_2$ alkoxy
or $C_1$–$C_2$ thioalkyl
M is Na or K Methods for performing the ester-to-methyl carbamate transformation are well known in the art; see Washburne et al. (*Syn. Commun.* 1972, 2, 227 and *J. Org. Chem.* 1973, 38, 2982). Related electrophiles for preparation of other preferred compounds are known to those skilled in the art. The procedures of Scheme 2 (reactions a and c) and modifications thereof are known in the art; see, for example, *J. Org. Chem.*, 1971, 36, 284 and WO 89/00991.

Compounds Of Formula I where Q is Q-1 and G is G-9 can be prepared by the reaction of aryl isocyanates of Formula III and tetrahydropyrazoles of Formula IV as shown in Scheme 3. Typical reactions involve the combination of equimolar amounts of III and IV in conventional organic solvents such as ether, tetrahydrofuran, dichloromethane, and toluene. The reaction can be run at temperatures between −20° C. and 80° C., with temperatures in the range of about 10° C. to 30° C. generally preferred.

Scheme 3

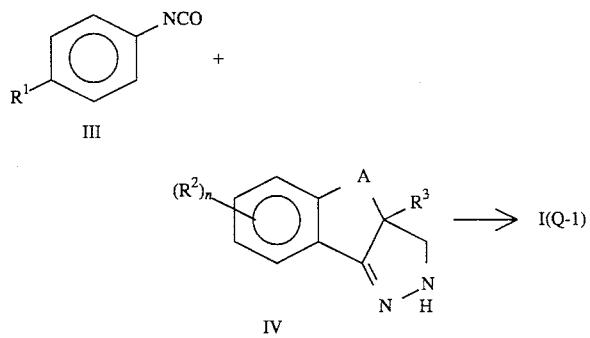

Alternative methods for preparing compounds of Formula I where Q is Q-1 and G is G-1 through G-10 are summarized in Schemes 4 and 5.

Scheme 4

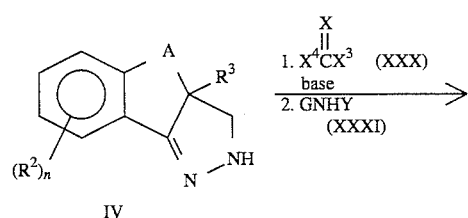

-continued
Scheme 4

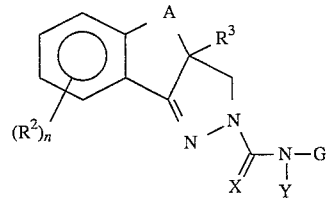

I
(Q = Q-1)

wherein:
$X^3$ and $X^4$ are groups such as halogen, imidazole, toluenesulfonate, phenoxide or alkoxide;
A, G, $R^2$, $R^3$, X and Y are as previously defined.

SCHEME 5

Step (i)

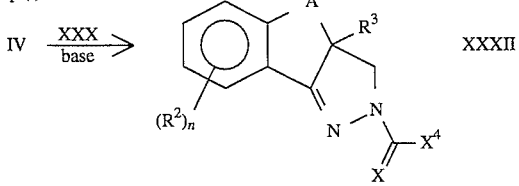

Step (ii)

XXXII $\xrightarrow[\text{base}]{\text{XXXI}}$ I (Q = Q-1)

wherein:
A, $R^2$, $R^3$, X and $X^4$ are as previously defined.

The reaction described in Scheme 4 is typically carried out in an inert solvent such as, but not limited to, dichloromethane, chloroform, or tetrahydrofuran. Approximately 200 to 500 mol percent of an organic base such as pyridine or triethylamine or an inorganic base such as potassium carbonate is mixed with the solution of equimolar amounts of IV and XXX in the solvent at a temperature between about 0° to 30° C. for a period of about one to twelve hours. An equimolar amount of XXXI is then added to the reaction mixture at a temperature of about 0° to 60° C. and the resulting mixture is stirred at that temperature for a period of about 2 and 20 hours. The product, I, can be isolated by removal of the solvent and silica gel chromatography of the residue. Suitable solvent mixtures for silica gel chromatography include, but are not limited to, ether-hexanes, ethyl acetate—hexanes and methylene chloride-ethanol-ammonium hydroxide.

The reaction described in Step (i) of Scheme 5 is typically carried out in an inert solvent such as dichloromethane, chloroform or tetrahydrofuran. Approximately 0 to 200 mol percent of a base such as, but not limited to, triethylamine or pyridine is mixed with the solution of equimolar amounts of IV and XXX in the solvent at a temperature between about 0° to 30° C. for a period of about one to twelve hours. Compound XXXII is isolated from the reaction mixture in crude form by removing the solvent, triturating the residue with a solvent such as ether, filtration and solvent removal of the filtrate.

The reaction described in Step (ii) of Scheme 5 is typically carried out in an inert solvent such as dichloromethane, chloroform or tetrahydrofuran. Approximately 100 to 300 mol percent of a base such as, but not limited to, triethylamine or pyridine is mixed with the solution of approximately equimolar Amounts of XXXI and XXXII at a temperature between 0° to 60° C. for a period of about 2 to 12 hours. The product, I, can be isolated by removal of the solvent and silica gel chromatography of the residue. Suitable solvent mixtures for silica gel chromatography include, but are not limited to, ether hexanes, ethyl acetate-hexanes and methylene chloride-ethanol-ammonium hydroxide.

Alternatively, 50 mol percent of trichloromethyl chloroformate (diphosgene) or 33 mol percent of bis-(trichloromethyl) carbonate (triphosgene) can be used in place of XXX using procedures analogous to those described in Schemes 4 and 5.

Alternatively, salts of XXXI (such as hydrohalides and the like) can be used in place of XXXI using procedures analogous to those described for Schemes 4 and 5.

Compounds of Formula IV can be prepared by acid hydrolysis of their phosphorylated derivatives of Formula V, as shown in Scheme 6.

SCHEME 6

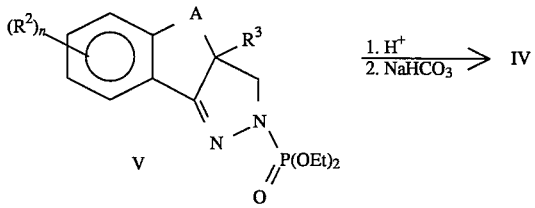

The reaction of Scheme 6 is generally carried out by contacting the substrate with two to three equivalents of a strong add such as HCl or p-toluene sulfonic acid, optionally containing some water, in a solvent such as ethanol or dioxane for 1 to 72 hours at 50° C. to 100° C. The initial product of the reaction is a salt of IV and can either be neutralized and extracted into an organic solvent for use in the reaction of Schemes 3, 4 and 5 or used directly in the presence of an additional two equivalents of a suitable organic or inorganic base.

Alternative methods for preparing Formula IV compounds can be found in U.S. Pat. No. 4,960,784, which methods are incorporated herein by reference.

The compounds of Formula V are produced by the cyclization reaction of an olefinic phosphorylhydrazone of Formula VI induced by the combination of mild base such as triethylamine and a mild halogenating agent such as N-bromosuccinlmide, as shown in Scheme 7.

SCHEME 7

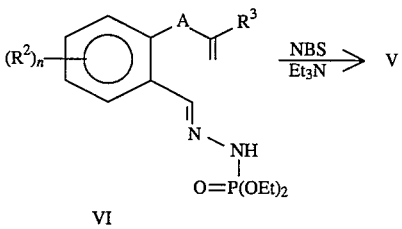

In the reaction of Scheme 7, the hydrazone of Formula VI is typically dissolved in an inert, anhydrous solvent in the presence of one of the base/haloimide components at −20° C. to 50° C. and the other component is added gradually. The product can be isolated by washing the reaction mixture with water, evaporating the solvent, and either recrystallizing or chromatographing to remove by-products.

The synthesis of compounds of Formula VI can be accomplished by condensing an aldehyde of Formula VII with diethyl phosphorohydrazidate VIII, as shown in Scheme 8.

SCHEME 8

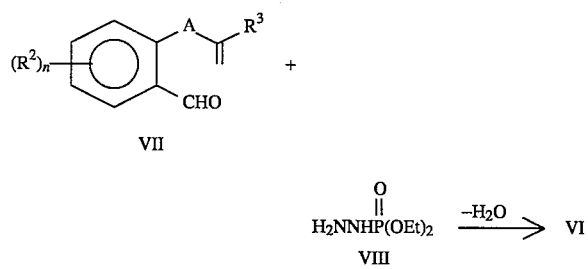

The reaction of Scheme 8 can be conducted by contacting aldehyde VII with slightly more than one equivalent of VIII in an inert solvent such as dichloromethane for about 0.1 to 16 hours, optionally in the presence of a catalytic (0.1 to 10%) amount of an acid such as acetic or p-toluenesulfonic, and optionally in the presence of an inorganic drying agent such as anhydrous magnesium sulfate. The product can be isolated by washing out excess VIII with water and concentrating the dried solution. It can be purified, if desired, by recrystallization or chromatography.

Compounds of Formula VII can be prepared by reacting an aniline, thiophenol or phenol of Formula IX with alkylating agents of Formula X, wherein L is a leaving-group, such as Cl, Br, I, $OSO_2CH_3$, or $OSO_2Ar$, as shown in Scheme 9.

SCHEME 9

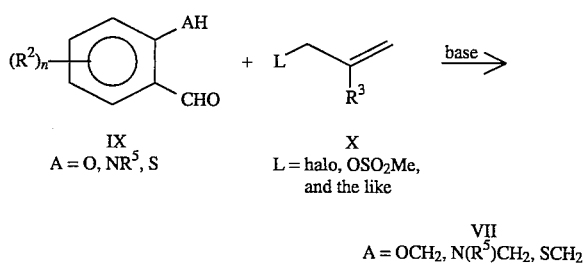

The reaction of Scheme 9 is typically carried out by combining equimolar quantities of IX and X in a suitable solvent for alkylation reactions, such as dimethylformamide (DMF) in the presence of slightly more than one equivalent of a suitable base, such as anhydrous potassium carbonate or sodium hydride and stirring vigorously at a temperature between 0° C. and 100° C. The product is generally isolated by diluting the mixture with water and filtering the precipitated product or extracting into a solvent such as ether. Recrystallization or chromatography affords the pure product.

Compounds of Formula IX will be recognized by those skilled in the art as being obtainable from substituted anilines, thiophenols or phenols by well-known methods. Compounds of Formula X are either known compounds or are readily available from olefins or allylic alcohols by know methods.

Compounds of Formula I where the preferred $R^3$ is a relatively stable group, for example substituted heterocycles, can be prepared from a compound of Formula X containing the desired $R^3$ group. Compounds of Formula I where the preferred $R^3$ is a reactive group, for example epoxide, must be prepared from a compound of Formula X containing a $R^3$ group that can be transformed into the desired $R^3$ group at the end of the synthesis. This strategy is depicted in Scheme 10.

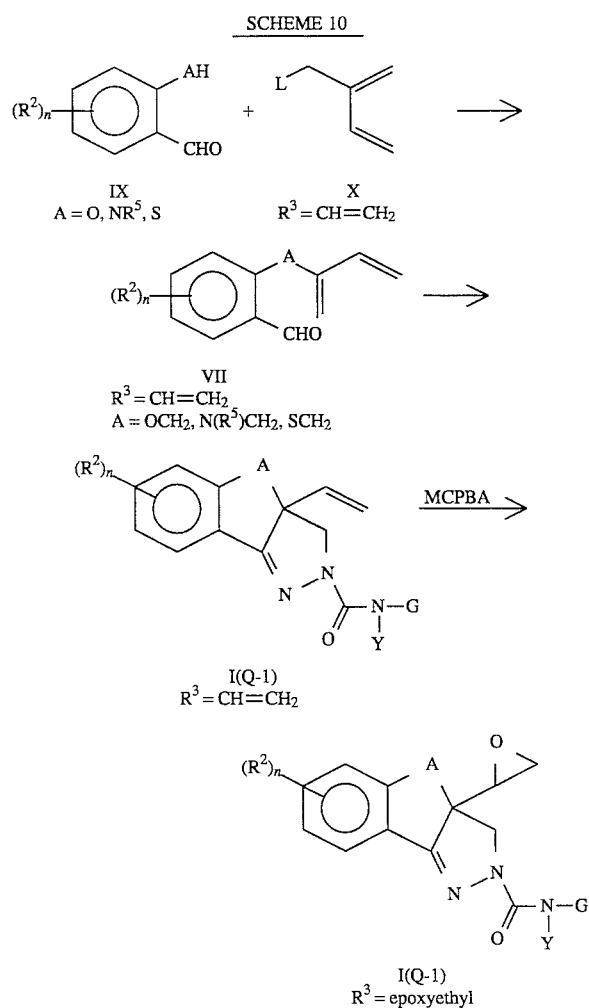

Compounds of Formula I where Q is Q-2

Compounds of Formula I, where Q is Q-2, can be obtained by the reaction of activated carbonyl or thiocarbonyl compounds of Formula XI with Formula XXXI compounds in the presence or absence of an acid acceptor or suitable condensing agent. Methods for performing this transformation are well known in the art; see, Zabicky, "The Chemistry of the Amides", Interscience, 1970.

One particularly useful method involves the chlorination of an acid derivative (XI, L=OH) with thionyl chloride or another chlorinating agent followed by treatment with XXXI in the presence of an acid acceptor such as an amine base, preferably triethylamine (Scheme 11). Suitable solvents for the chlorination reaction are inert to hydrogen chloride and include benzene, toluene, and dichloromethane. Preferred temperatures for this process are from 20° to 100° C. with temperatures between 20° and 80° C. being particularly preferred. The latter reaction can be carried out in many different inert solvents such as dialkylethers, chlorinated hydrocarbons, and aromatic hydrocarbons. These reactions are normally run at atmospheric pressure, but can also be carried out at elevated pressures.

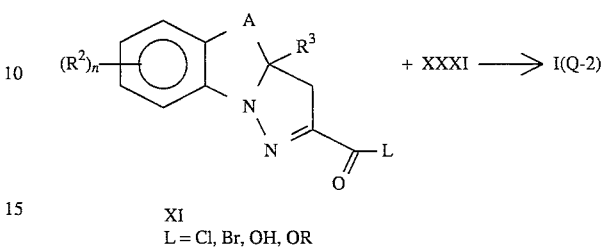

Esters of Formula XI (L=$C_1$–$C_6$ alkoxy) can be converted directly to compounds of Formula I (Q=Q-2) in several ways. In the presence of Lewis acids such as $AlMe_3$, anilines react readily with esters of Formula XI. The reaction is best carried out at room temperature to 120° C. Suitable solvents include dichloromethane, 1,2-dichloroethane, and toluene. The method described by Weinreb et al., *Organic Synthesis*, 59, 49, (1982), proceeds best with esters of lower alcohols such as methanol or ethanol.

Acids of Formula XI (L=OH) can be converted directly to compounds of Formula I by use of coupling agents known in the peptide art in conjuction with anilines. Coupling agents include dicyclohexylcarbodiimide (DCC), N-hydroxysuccinimide, 2-chloro-N-methylpyridinium iodide, carbonyl diimidazole, or other agents capable of activating an acid function or acting as a dehydrating agent. These and other methods are described in Gross et al., "The Peptides," 3 Vols., Academic Press, New York, 1979 to 1981.

Compounds of Formula I (Q=Q-2) and intermediates of Formula XI can be obtained by the intramolecular dipolar cycloaddition reaction of nitrile-imines, generated from substituted phenylhydrazones of Formula XIII (Scheme 12). The presence of an acid acceptor (generally an amine base, for example, triethylamine) is necessary for the formation of the nitrile-imine. Suitable solvents include but are not restricted to benzene, toluene, 1,2-dichloroethane, chloroform, and tetrahydrofuran. The reaction can be carried out at temperatures ranging from 20° to 120° C. with the relative reactivity of the alkene moiety governing the required temperature for a given example.

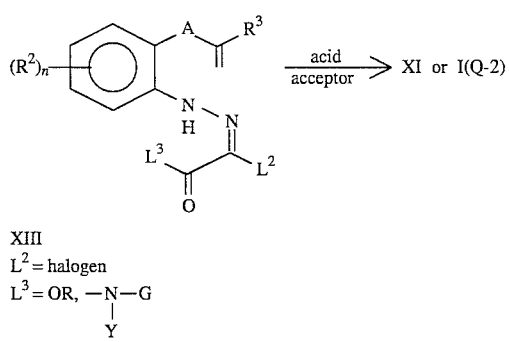

The required hydrazones of Formula XIII can be synthesized by the Japp-Klingemann reaction (Scheme 13). The coupling of diazonium salts with active methylene compounds is known. The more specific coupling of chloroacetoacetic acid derivatives of Formula XIV with diazotized anilines of Formula XV containing alkenyl substituents is described by Padwa et al. in *J. Org. Chem.*, 43, 1664 (1978) and *J. Org. Chem.*, 46, 1402 (1981). A similar process for this type of aniline is described by Garanti et al. in *J. Org. Chem.* 42, 1389 (1977), and *J. Chem. Soc. Perkin I*, 2245 (1981).

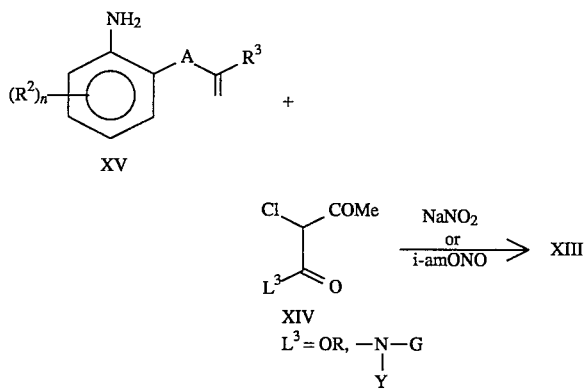

The anilines of Formula XV can be obtained by the reduction of aromatic nitro compounds of Formula XVI (Scheme 14). There are many methods known for this transformation. See, March, "Advanced Organic Chemistry", 1985, Wiley, page 1103–1104. A particularly suitable method involves the treatment of the nitro compound with tin (II) chloride in alcoholic solvents. Refer to Bellamy et al. *Tetrahedron Letters*, 1984, 839.

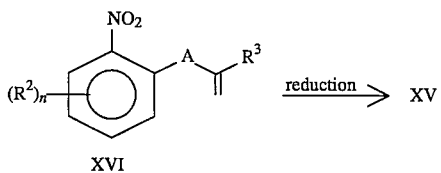

Nitro compounds of Formula XVI containing a heteroatom in the alkenyl chain can be obtained by alkylation reactions (Scheme 15). Treatment of a substituted phenol, thiophenol, or aniline of Formula XVII with an acid acceptor and an allyl or homoallyl halide or sulfonate of formula XVIII gives compounds of Formula XVI as products. Preferred acid acceptors for the process are inorganic bases such as potassium carbonate. Preferred solvents include dimethylformamide, dimethylsulfoxide, methylethyl ketone, and ethanol. The reaction is generally carried out at room temperature, but higher temperatures may be necessary in some cases. Alternative methods for these nitro compounds of Formula XVI have been described by Oae et al. in *Bull. Chem. Jap.*, 54, 2374 (1981).

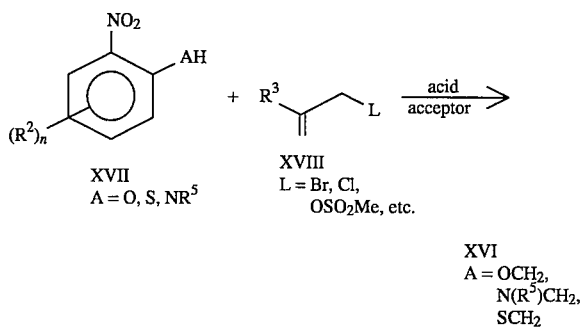

Compounds of Formula XVII and compounds of Formula XVIII having the preferred $R^3$ groups of this invention are either known compounds or can be prepared by conventional methods.

Compounds of Formula I where Q is Q-3

The compounds of Formula I, where Q is Q-3 and G is G-9, can be prepared by the reaction of hydrazones of Formula XIX with an aryl isocyanate of Formula III (Scheme 16). Typical reactions involve combination of equimolar amounts of XIX and III in a suitable solvent at temperatures generally in the range of −10° to 100° C. Although the reaction can be run neat, a solvent is generally preferred. Suitable solvents typically have sufficient polarity to effect solution of the Formula XIX hydrazone and include, but are not limited to, ethers such as diethyl ether, tetrahydrofuran and dioxane; halogenated hydrocarbons such as methylene chloride, chloroform and carbon tetrachloride;

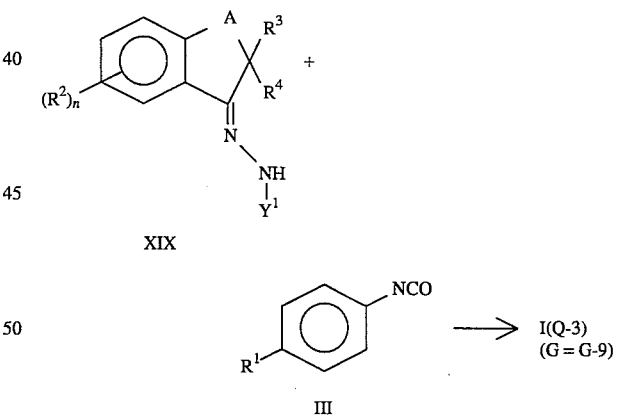

aromatic hydrocarbons such as benzene, toluene and xylene; esters such as ethyl acetate and polar aprotic solvents such as dimethylformamide and dimethylacetamide.

The hydrazones of Formula XIX can be obtained by processes known in the art involving condensation of a ketone of Formula XX with either hydrazine or a substituted hydrazine of Formula XXI (Scheme 17). This reaction is typically conducted with equimolar amounts of XX and XXI although greater than stoichiometric amounts of hydrazine can be used. Suitable solvents include the alcohols such as methanol, ethanol, propanol, butanol and the like at temperatures in the range of 0° to 150° C., with the reflux temperature of the solvent generally being a convenient reaction temperature. Acid catalysis can also be useful, particularly for some of the more sterically hindered Formula XX compounds. Typical acid catalysts include sulfuric, hydrochloric and p-toluenesulfonic acid.

SCHEME 17

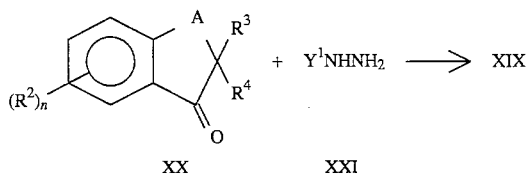

An alternate process useful for the preparation of compounds of Formula I involves condensation of a semicarbazide of Formula XXII with a ketone of Formula XX (Scheme 18). Preferred conditions for this reaction include an acid catalyst such as hydrochloric, sulfuric or p-toluene sulfonic acid. Reaction temperatures can range from 0° to 150° C. with the reflux temperature of the solvent used generally preferred. Suitable solvents include, but are not limited to, ethers such as tetrahydrofuran and dioxane; aromatic hydrocarbons such as benzene and toluene; and especially preferred are alcohols such as methanol, ethanol and isopropanol.

SCHEME 18

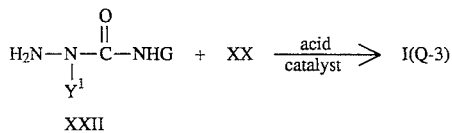

Semicarbazide of Formula XXII can be prepared using procedures described by Scheme 19. The first step (Step (i)) of Scheme 19) involves the reaction of equimolar amounts of an amine XXXI (Y is H) with XXX in a suitable solvent at a temperature between about 0° to 100° C. for a period of about 1 to 36 hours. In some cases it is desirable to use 0 to 200 mol percent of a base such as, but not limited to, triethylamine or pyridine. Suitable solvents include, but are not limited to, dichloromethane, chloroform or tetrahydrofuran. The product, XXXIII, is typically isolated by evaporation of the solvents and used directly in step ii of Scheme 19.

In step ii of Scheme 19, XXXIII is mixed with 1 to 5 equivalents of a hydrazine XXI in the presence of 0 to 3 equivalents of a base in a suitable solvent at a temperature ranging from 0° C. to the boiling point of the solvent. Suitable bases include both inorganic bases as well as organic amines such as pyridine and triethylamine. Suitable solvents include, but are not limited to, alcohols such as methanol, ethanol and isopropanol, acetonitrile, chloroform and tetrahydrofuran. Reactions of step ii of Scheme 19 are typically run for a period of 6 to 72 hours, and the product XXII is usually isolated by chromatography on silica gel using a mixture of methylene chloride, ethanol and aqueous ammonium hydroxide as the eluant.

SCHEME 19

Step (i)

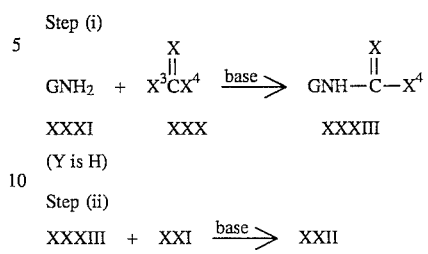

(Y is H)

Step (ii)

XXXIII + XXI $\xrightarrow{\text{base}}$ XXII

Alternatively, semicarbazide of Formula XXII can be prepared by reactions of hydrazines XXI with isocyanates III using procedures that are well-known to those skilled in the art.

Compounds of Formula I where Y and $Y^1$ are other than hydrogen can generally be prepared from the corresponding compounds where Y and $Y^1$ are hydrogen by reaction with electrophilic reagents such as alkyl halides, acyl halides, alkyl chloroformates and sulfenylhalides. The use of a base is generally preferred in these reactions but is dependent upon the specific nature of the reactants. For example, when the electrophilic reagent is selected from an alkyl halide, acyl halide or alkyl chloroformate, then metal hydrides such as sodium hydride or potassium hydride in solvents such as tetrahydrofuran or dimethylformamide are preferred. When sulfenyl halides are used then amine bases such as triethylamine in solvents such as diethyl ether or tetrahydrofuran are generally preferred. Of course, many of the compounds where $Y^1$ is other than H can also be prepared by use of the appropriate hydrazine XXI in Scheme 17. For example, methyl hydrazine and methyl carbazate will produce compounds where $Y^1$ is methyl and carbomethoxy, respectively.

The starting ketones of Formula XX are known or can be obtained by processes analogous to known ones. Those skilled in the art will recognize the Formula XX compounds to include substituted indanones, tetralones, chromanones, thiochromanones, benzofuran-3-ones, thiobenzofuran-3-ones, isochromanones, isothiochromanones and others.

Compounds of Formula I where Q is Q-4

Compounds of Formula I where Q is Q-4 can be prepared by the methods reported in WO-88/900,910. Scheme 20 depicts a particularly useful method discussed in WO 88/900,910.

SCHEME 20

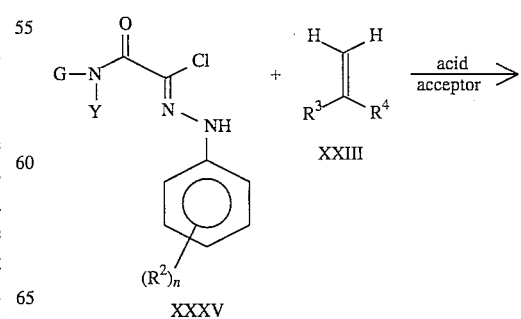

-continued
SCHEME 20

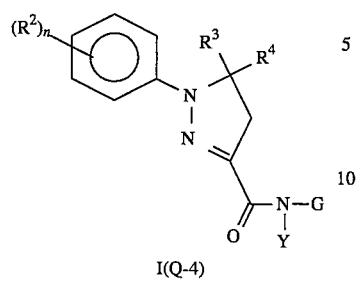

I(Q-4)

Hydrazones of Formula XXXV can be prepared analogously to Formula XIII compounds as described in Scheme 13. Alkene XXIII can be prepared with $R^3$ being equal to one of the preferred groups of this invention. Compounds of Formula XXIII are either known compounds or readily available by methods known to those skilled in the art.

Compounds of Formula I where Q is Q-5 through Q-9

Compounds of Formula I (Q-5) wherein $R^{18}$ is equal to H and G is G-9 can be prepared by the reaction of aryl isocyanates of Formula III with substituted pyrazolidines of Formula XXIV as illustrated in Scheme 21. Typical reactions involve the combination of equimolar mounts of III and XXIV in conventional organic solvents including ethyl acetate, ether, tetrahydrofuran, methylene chloride, chloroform, benzene and toluene but not restricted to these. The reaction can be conducted at temperatures ranging from –20° C. to 100° C. with temperatures in the range of –10° C. to 30° C. generally preferred.

SCHEME 21

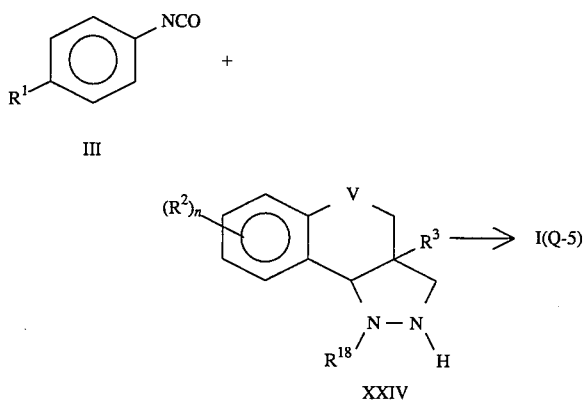

Alternatively, compounds of Formula I (Q-5) where $R^{18}$ is H and G is G-1 through G-10 can be prepared from compounds of Formula XXIV using procedures analogous to those already described for the syntheses of compounds of Formula I (Q-1) in Schemes 4 and 5 and, for the sake of brevity, will not be described further.

Compound of Formula XXIV can be prepared by the reaction of hydrazine dihydrochloride or hydrazine sulfate with compounds of Formula XXV as illustrated in Scheme 22. Modification of the procedure described in *Bull. Chem. Soc,. Jap.*, 1982, 55, 2450, and *J. Org. Chem.*, 1987, 52, 2277, can be applied to the synthesis of compounds of the Formula XXIV. Typical reactions involve the addition of an excess of equivalents of hydrazine dihydrochloride or hydrazine sulfate, ranging from 1.1 to 20 equivalents with 5 to 15 equivalents being preferred, to one equivalent of a compound of Formula XXV in an alcohol/water solvent mixture ranging from 1 to 99% alcohol with 90% to 95% alcohol being preferred. Typical alcoholic solvents include methanol, ethanol, n-propanol, n-butanol, tert-butanol and the like. The reaction can be conducted at temperatures ranging from –20° C. to 140° C. with temperatures in the range of 20° C. to 80° C. being preferred. The reaction is usually complete within 24 hours.

SCHEME 22

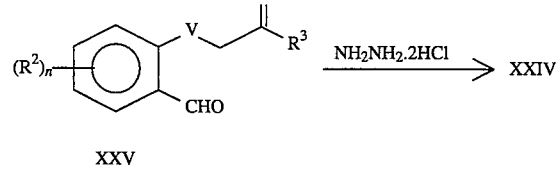

Substituted benzaldehydes of Formula XXV can be prepared by known methods or obvious modifications thereof by one skilled in the art.

Compounds of Formula I (Q-5) where $R^{18}$ is not equal to H can be prepared by the reaction of Formula I (Q-5) where $R^{18}$ is equal to H with a variety of electrophiles. For example, these electrophiles include, but are not limited to, alkyl halides, alkyl and aryl isocyanates, acyl halides, sulfonyl halides and alkyl chlorocarbonates. Reactions to prepare Formula I (Q-5) compounds where $R^{18}$ is not equal to H can be conducted through standard procedures known to those skilled in the art. For example, the reaction of Formula I (Q-5) compounds where $R^{18}$ is equal to H with methyl isocyanate (Scheme 23) can be conducted by reaction of equal molar amounts of the reactants in an inert solvent such as, but not limited to, ether, tetrahydrofuran, dimethoxyethane, ethyl acetate, methylene chloride and chloroform, in the presence of an acid scavenger such as tertiary alkylamines, substituted pyridines, alkali metals, and the like.

SCHEME 23

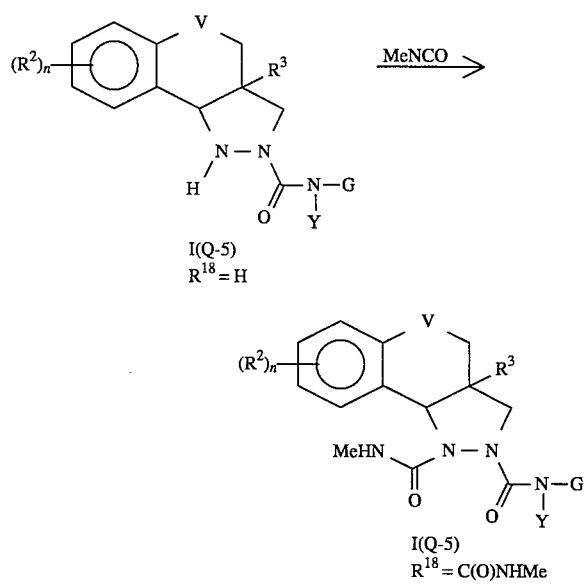

Compounds of Formula I (Q-6) can be prepared by the reaction of tri- and tetravalent metal species such as titanium, silicon, tin and the like in combination with a reducing agent such as sodium, lithium, or zinc borohydride, lithium aluminum hydride and the like with compounds of Formula I where Q is equal to Q-2 as illustrated in Scheme 24. Literature precedent for analogous reactions can be found in *J. Org. Chem.,* 1987, 54, 3750, and *Synthesis,* 1980, 695. Typical reactions involve the addition of 1 equivalent of a compound of Formula I (Q-2) to a solution of 1.1 to 4 equivalents of titanium tetrachloride, with 1.5 to 2.5 equivalents being preferred, and 2.1 to 6 equivalents of sodium borohydride with 3.5–4.5 equivalents being preferred.

Conventional organic solvents such as ether, tetrahydrofuran, dimethoxyethane, methylene chloride and chloroform can be used with 1,2-dimethoxyethane being preferred. The reaction can be conducted at temperatures ranging from −70° C. to 50° C. with —10° C to 30° C. being preferred. The reaction time can be 0.1 hour to 48 hours with 2 to 4 hours being preferred.

SCHEME 24

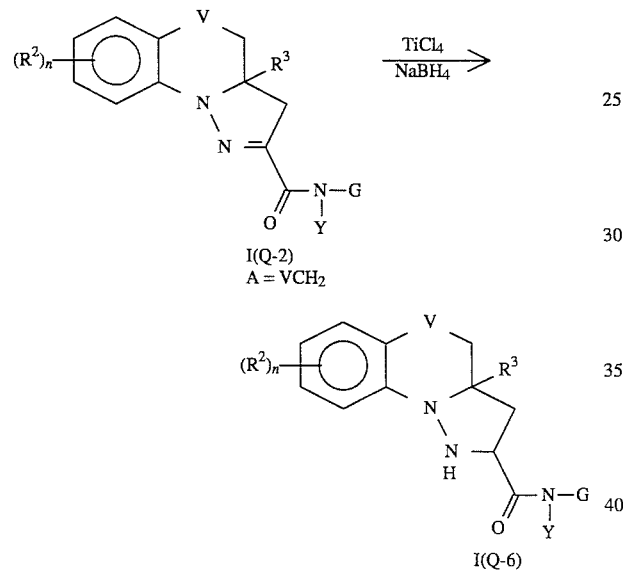

I(Q-2)
A = VCH₂

I(Q-6)

Formula I (Q-6) compounds where $R^{18}$ is not equal to H can be prepared in the same fashion as described for Formula I (Q-5) compounds where $R^{18}$ is not equal to H.

Compounds of Formula I (Q-7) can be prepared by a titanium tetrachloride/sodium borohydride reduction of Formula I (Q-3) analogs in a similar fashion as described for Formula I (Q-6) compounds. Scheme 25 illustrates the methodology utilized.

SCHEME 25

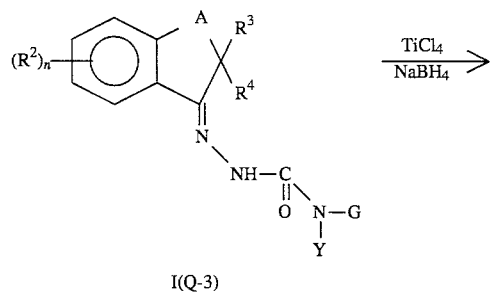

I(Q-3)

-continued
SCHEME 25

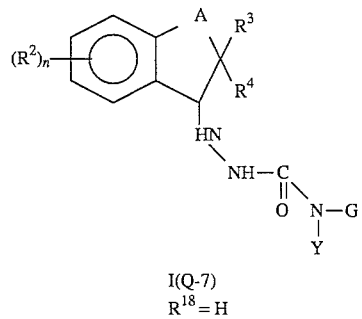

I(Q-7)
$R^{18} = H$

The compounds represented by Formula I (Q-8) can be prepared by a titanium tetrachloride/sodium borohydride reduction of Formula XXVI analogs in a similar fashion as described for Formula I (Q-6) compounds. Scheme 26 illustrates this methodology.

SCHEME 26

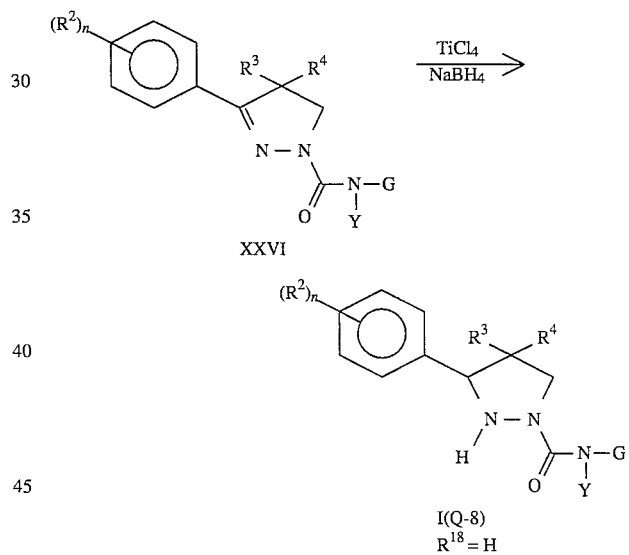

XXVI

I(Q-8)
$R^{18} = H$

The preparation of the compounds represented by Formula XXVI is described in U.S. Pat. Nos. 4,070,365, and 4,633,341.

For example, the 3-phenyl-dihydropyrazoline intermediate is prepared using conventional procedures and further reacted with an appropriately substituted phenyl isocyanate.

The compounds represented by Formula I (Q-9) can be prepared by a titanium tetrachloride/sodium borohydride reduction of Formula I (Q-4) analogs in a similar fashion as described for Formula I (Q-6) compounds. Scheme 27 illustrates this methodology.

SCHEME 27

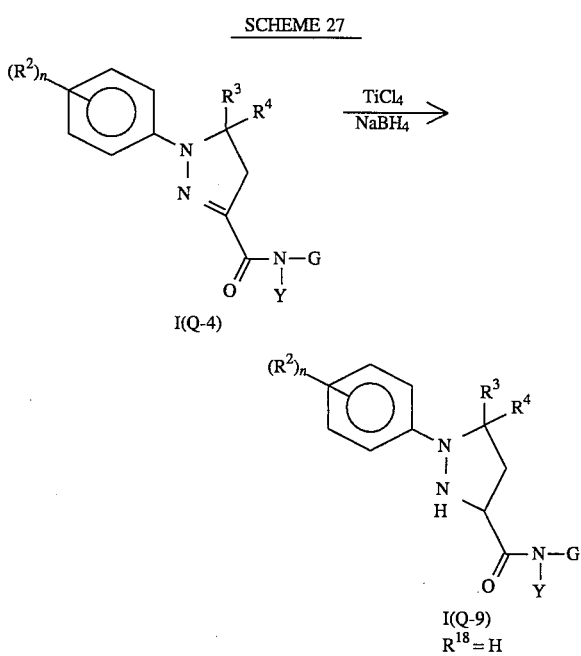

Compounds of Formula I where Q is Q-10

The preparation of compounds of Formula I where Q is Q-10 is similar to that for compounds where Q is equal to Q-1. Cyclic alkylating agents of Formula XXVII are used in place of standard allylic halides for the alkylation of phenols or anilines as depicted in Scheme 28 (see Scheme 9 for reference).

SCHEME 28

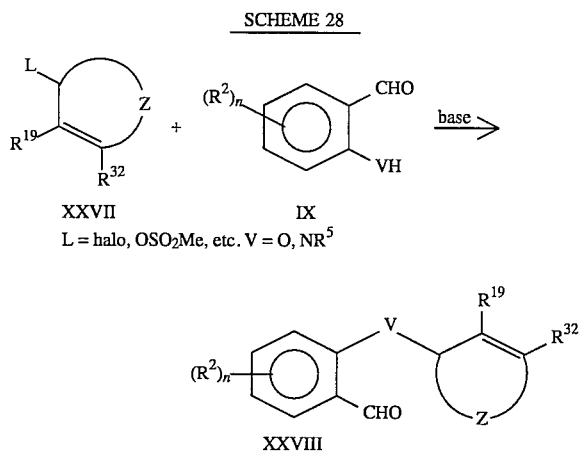

L = halo, OSO₂Me, etc. V = O, NR⁵

Compounds of Formula XXVIII are carried through the identical reaction sequence in Schemes 6 through 8 to give the desired tetracyclic pyrazoles XXXIV (Scheme 29).

SCHEME 29

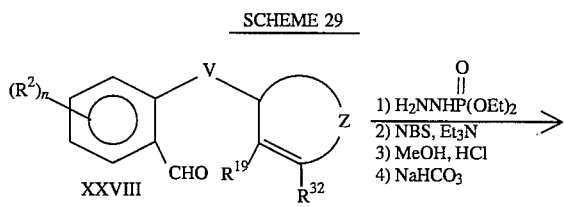

-continued
SCHEME 29

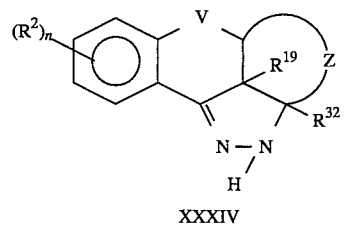

The tetracyclic pyrazoles XXXIV can then be converted to compounds of Formula I where Q is Q-10 and G is G-9 by treatment with acyl isocyanates using procedures completely analogous to those described in Scheme 3.

Compounds of Formula I where Q is Q-10 and G is G-1 through G-10 can be prepared from Formula XXXIV using procedures analogous to those described for Schemes 4 and 5.

Compounds of Formula I where Q is Q-11

Compounds of Formula I where Q is Q-11 can be prepared using the same procedure described for compounds where Q is equal to Q-3. The tricyclic ketone starting material can be prepared according to literature procedures (see Marchant, *J. Chem. Soc.* 1957, 3325).

Compounds of Formula II where Q is Q-1 through Q-11

Compounds of Formula II can be prepared by the reaction of a Formula I compound with an appropriate halogenating agent such as phosphorous trichloride, phosphorous pentachloride, phosphorous tribromide, phosphorous pentabromide, thionyl chloride, sulfuryl chloride, triphenyl phosphine and carbon tetrachloride (Wolkoff, *Can. J. Chem.* 1975, 53, 1333) and the like (see Fieser and Fieser, Reagents for Organic Synthesis, Vol. I, 1967) as illustrated in Scheme 30. Typical reactions involve the combination of Formula I compounds with an excess of the halogenating agent ranging from 1.1 to 10 equivalents, with 2 to 4 equivalents being preferred. The reaction can be conducted in the absence of a solvent or in the presence of a conventional organic solvent such as benzene, toluene, xylene, chloroform, methylene chloride, hexane and the like. The reaction temperature can range from −10° C. to 200° C. with 35° C. to 100° C. being preferred. The reaction is generally complete after 24 hours.

SCHEME 30

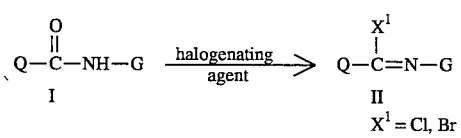

X¹ = Cl, Br

Alternatively, compounds of Formula H when X¹ is equal to R⁶—S, can be prepared by the reaction of compounds of the Formula I with an electrophile of the Formula XXIX in the presence of a suitable base, as illustrated in Scheme 31. Typical reactions involve the combination of equimolar amounts of Formula I compounds and the appropriate electrophile of Formula XXIX. A base such as an alkali metal, tertiary amine or metal hydride can be used.

SCHEME 31

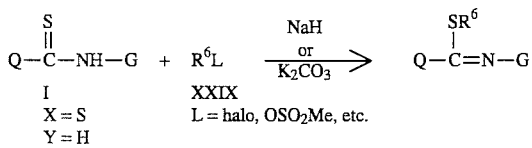

X = S
Y = H
XXIX
L = halo, OSO₂Me, etc.

The following Examples further illustrate the invention.

EXAMPLE 1

Step A: ((2-(3-chlorophenyl)ethyl)methanesulfonate

To a 0° C. solution of 30.0 g of 3-chlorophenethyl alcohol and 15.3 mL of methane sulfonyl chloride in 150 mL of THF was added, dropwise, a solution of 28.0 mL of triethylamine in 50 mL, of THF. The reaction was warmed to room temperature, stirred overnight, and then filtered. The filtrate was partitioned between aqueous sodium bicarbonate and ether. The organic extracts were then dried over magnesium sulfate, filtered and concentrated under reduced pressure to afford 45.93 g of a clear, colorless oil. $^1$H NMR was consistent with the structure for the named compound.

Step B: 3-chlorobenzenebutanoic acid

To a mixture of 8.0–60% sodium hydride in 300 mL, of THF, under $N_2$, Was added dropwise a solution of 31.0 mL of diethyl malonate in 50 mL of THF. Upon complete addition of the diethyl malonate, a pale yellow homogeneous solution was obtained. To this was added a solution of 45.93 g of the sulfonate from Step A and the mixture was then heated at reflux overnight. The reaction was then cooled to room temperature, poured into 400 mL of 1N HCl, and extracted with ether. The ether extracts were dried over magnesium sulfate, filtered and concentrated under reduced pressure to afford 68.9 g of a yellow oil. The crude oil was dissolved in 400 mL of methanol, 100 mL of $H_2O$ and 40 mL, of 50% aqueous NaOH. The reaction was stirred overnight and the methanol was then removed at reduced pressure. The crude residue was partitioned between $H_2O$ and ether, the aqueous extracts were acidified with concentrated HCl and then extracted several times with ether. The ether extracts were dried over magnesium sulfate, filtered and concentrated to afford 51.7 g of a yellow oil. The crude residue was dissolved in 200 mL, of toluene and heated at reflux for 4 days under $N_2$ to effect decarboxylation. After this time, toluene was removed by concentration at reduced pressure to afford 35.72 g of a yellow oil. $^1$H NMR analysis of the crude product was consistent with 3-chlorobenzenebutanoic acid of purity estimated to be 80%. The crude product was used without further purification directly in the next step.

Step C: 6-chloro-3,4-dihydro-1(2H)-naphthalenone

A mixture of 35.72 g of the product from Step B and 50 mL of thionyl chloride was heated at reflux for 2 hours and then stirred at room temperature for 18 h. After this time, thionyl chloride was removed at reduced pressure and the product was dissolved in carbon tetrachloride and concentrated at reduced pressure. The residue was dissolved in 150 mL of dichloroethane cooled to 0° C. and 28 g of aluminum chloride was added portionwise over about 1 hr in approximately 3 g portions. After stirring for 3 h, the reaction was poured over a mixture of ice/1N HCl and extracted three times with methylene chloride. The organic extracts were dried over magnesium sulfate and concentrated to approximately 30 g of a brown oil. Chromatography on silica gel with 10% ethyl acetate/hexane afforded 17.83 g of 6-chloro-3,4-dihydro-1(2H)-naphthalenone as a brown oil. $^1$H NMR was consistent with the structure.

Step D: 7-chloro-3,3a,4,5-tetrahydro-N-[4-(trifluoromethyl)phenyl]-2H-benz[g]-indazole-2-carboxamide A mixture of 3.4 g (0.03 mole) of 6-chloro-3,4-dihydro-1(2H)-naphthalenone (Step C), 2.5 g of dimethylamine hydrochloride, 1.0 g of paraformaldehyde, 0.7 mL, of concentrated HCl and 15 mL, of ethanol was combined and heated at reflux for 18 h. The reaction was then concentrated at reduced pressure and partitioned between $H_2O$ and ether. The aqueous extracts were made basic with 1N NaOH and then extracted three times with ether. The ether extracts were dried over magnesium sulfate and concentrated to 4.64 g of a yellow oil. This compound was dissolved in 25 mL of ethanol and 1.5 mL of hydrazine hydrate was added followed by 5 to 6 drops of 50% sodium hydroxide. The reaction was then heated at reflux, under $N_2$, for 2 to 3 h after which time it was cooled and most of the ethanol was removed by concentration at reduced pressure. The crude residue was partitioned between saturated aqueous sodium bicarbonate and methylene chloride. The methylene chloride extracts were dried over magnesium sulfate and filtered. The methylene chloride extracts were then combined with 3.5 g of 4-trifluoromethylphenyl isocyanate and stirred under $N_2$ overnight. The reaction was then concentrated and the crude residue triturated with ether to afford 3.35 g of the product as a white powder, mp 196°–199° C. $^1$H NMR (CDCl$_3$) δ1.9 (m, 1H), 2.2 (m, 1H), 3.0 (m, 2H), 3.5 (in, 2H), 4.43 (m, 1H), 7.24 (m, 2H), 7.55 (d, 2H), 7.67 (d, 2H), 7.92 (d, 1H), 8.20(s, 1H).

Step E: 7-chloro-3a-cyano-3a,4-dihydro-N-[4-(trifluoromethyl)phenyl][1]benzopyrano[4.3-c]pyrazole-2(3H)-carboxamide To a solution of diisopropylamine (0.42 mL, 3.0 mmoles) in 10 mL of THF was added, n-butyllithium (1.9 mL of 1.6M, 3.0 mmole) at −78° C. under $N_2$. After 15 min, a solution of the product of Step D (0.5 g, 1.3 mmole) in 3 mL of THF was added dropwise and the dark red solution that formed was stirred at −78° C. for an additional 15 min. Then, p-toluene-sulfonyl cyanide (0.31 g, 1.7 mmole) in 2 mL of THF was added dropwise to the reaction mixture which decolorized near the end of the addition. Saturated aqueous NH$_4$Cl was added and the reaction was allowed to warm to room temperature. The aqueous phase was extracted with ethyl acetate and the combined organic phases were dried (MgSO$_4$) and concentrated (vacuum). The resulting solid was triturated with ether to afford the title compound (0.36 g, 66% yield) as a white solid, mp 227°–229° C. $^1$H NMR (CDCl$_3$): δ8.10 (s, 1H), 7.91 (d, 1H), 7.62 (ABq, 4H), 7.30 (m, 2H), 4.79 (d, 1H), 3.81 (d, 1H), 3.41 (m, 1H), 3.04 (m, 1H), 2.68 (m, 1H), 2.15 (td, 1H).

EXAMPLE 2

Step A: 2-bromoethyl-1,3-butadiene

Phosphorous tribromide (5.13 mL, 0.054 mol) was added over 10 min to a solution of 11.3 g (0.13 mol) of 2-hydroxymethyl1,3-butadiene (R. Silverstein, et al., *J. Org. chem.*, 1974, 39, 1957) and 270 mL of diethyl ether at 0° C. The resulting solution was warmed to 24° C. and stirred at that temperature for 10 h and then cooled to 0° C. and poured into 500 mL, of ice-water. The aqueous layer was separated and extracted with two 100 mL, portions of ether and the combined organic layers were washed with 200 mL, of saturated sodium bicarbonate solution, dried (MgSO$_4$) and concentrated in vacuo at 24° C. to give 10.5 g of a yellow oil that is used immediately without further purification. 90 MHz ¹H NMR (CDCl₃) δ4.15 (s, 2H), 5.2–5.6 (m, 4H), 6.40 (dd, 1H).

Step B: 4-Chloro-2-hydroxybenzaldehyde

Modification of a procedure described by G. Casiraghi et al., (*J. Chem. Soc., Perkin Transac. I.*, 1978, 318), was utilized in the preparation of substituted salicylaldehydes. To a mixture of 26 g of 3-chlorophenol dissolved in 200 mL, of toluene at 10° C. was added dropwise 100 mL, of a 2M solution of ethylmagnesium chloride in diethyl ether. The ether was distilled off and the reaction mixture was cooled to room temperature and 26.0 g of 1,3-dimethyl-3,4,5,6-tetrahydro-2(1H)-pyrimidinone (DMPU) was added followed by 15.0 g of paraformaldehyde. The reaction mixture was heated at 70° C. for 18 h, cooled to 10° C. and a solution of 20 mL of concentrated HCl in 100 g of ice was added followed by 200 mL of hexane. The organic phase was separated and washed twice with 100 mL of water, once with 100 mL of brine, dried over anhydrous MgSO₄, filtered and concentrated under vacuum to afford a viscous oil. This was taken up in 150 mL of ethanol and a solution of 15.0 g of copper (II) acetate dissolved in 150 mL of H₂O was added dropwise. The resulting precipitate was filtered, washed with water and then with ether and added to a solution of 200 mL of ether and 20 mL of concentrated H₂SO₄ in 100 g of ice. The mixture was stirred until all solids were dissolved, 100 mL of hexane was added, and the organics were washed with 100 mL of H₂O, then 100 mL of brine, dried over anhydrous MgSO₄, filtered and concentrated under vacuum to afford 15.0 g of a yellow solid, mp 47°–48° C. ¹H NMR (CDCl₃) δ6.98 (d, 1H), 7.01 (s, 1H), 7.50 (d, 1H), 9.85 (s, 1H), 11.18 (s, 1H). IR (Nujol) 3300–2800, 1670 cm⁻¹.

Step C: 4-chloro-2-[(2-methylene-3-butenyl)oxy]benzaldehyde

To a solution of 4.1 g (0.026 mol) of 4-chloro-2-hydroxybenzaldehyde and 27 mL of DMF was added 5 g (0.034 mol) of 2-bromomethyl-1,3-butadiene and 7.2 g (0.052 mol) of potassium carbonate. The resulting mixture was heated at 70° C. for 4 h and then cooled to room temperature and poured into a mixture of 100 mL of water and 100 mL of methylene chloride. The aqueous layer was extracted with two 100 mL portions of methylene chloride and the combined organic layers were washed twice with 100 mL of water, twice with 100 mL of saturated sodium bicarbonate solution, dried over magnesium sulfate and concentrated to give 4.9 g of an oil. Purification by flash chromatography using 250 g of silica gel and eluting with 10:1 hexanes-EtOAc gave 2.6 g of the desired product. 200 MHz ¹H NMR (CDCl₃): δ4.82 (s, 2H), 5.18–5.42 (m, 4H), 6.45 (dd, 1H), 7.01 (s, 1H), 7.05 (d, 1H), 7.79 (d, 1H), 10.48 (s, 1H).

Step D: Diethyl[[4-chloro-2[(2-methylene-3-butenyl)oxy]phenyl]methylene]phosphorohydrazidate Diethyl phosphorohydrazidate (2.6 g, 0.015 mol) was added to a solution of 2.6 (0.012 mol) of the product of Step C, 0.8 mL of glacial acetic add and 24 mL of ether at 0° C. The resulting solution was stirred at room temperature for 15 h and then was partitioned between methylene chloride and 1M HCl. The aqueous layer was extracted with two portions of methylene chloride and the combined organics were washed twice with 1M HCl, twice with saturated sodium bicarbonate solution, dried over anhydrous magnesium sulfate, filtered and concentrated to give 2.9 g of a yellow solid melting at 112°–118° C. 200 MHz ¹H NMR(CDCl₃): δ1.37 (t, 6H), 4.1–4.3 (m, 4H), 4.72 (s, 2H), 5.2– 5.4 (m, 4H), 6.45 (dd, 1H), 6.75–7.0 (m, 3H), 7.81 (d, 1H), 8.05 (s, 1H).

Step E: Diethyl (7-chloro-3a-ethenyl-2,3,3a,4-tetrahydro[1]benzopyrano[4.3-c]-pyrazol-2-yl)phosphonate N-Chlorosuccinimide (1.0 g, 0.007 mol) was added to a mixture of 2.7 g (0.007 mol) of the product from Step D, 0.75 g of 3A molecular sieves and 120 mL of methylene chloride. The resulting mixture was cooled to 0° C. and was treated with a solution of 1.3 mL of triethylamine and 60 mL of methylene chloride. The resulting mixture was stirred at room temperature for 4 h and then decanted into 100 mL of water. The aqueous layer was extracted with two 50 mL portions of methylene chloride and the combined organic layers were washed with water and saturated sodium bicarbonate solution, dried over anhydrous magnesium sulfate and concentrated to give 2.9 g of a brown oil. Flash chromatography on silica gel using 1:3 hexanes-EtOAc afforded 1.0 g of a light yellow oil. 200 MHz ¹H NMR (CDCl₃): δ1.36 (t, 6H), 3.55 (dd, 1H), 3.9 (d, 1H), 4.1–14.3 (m, 5H), 4.60 (d, 1H), 5.15–5.3 (m, 2H), 5.90–6.05 (m, 1H), 6.9–7.0 (m, 2H), 7.78 (d, 1H).

Step F: 7-Chloro-3a-ethenyl-2,3,3a,4-tetrahydro-N-[4-(trifluoromethyl)phenyl][1]benzopyrano[4,3-c]pyrazole-2-carboxamide A solution of 1.0 g (0.003 mol) of the product from Step E, 16 mL of methanol and 0.5 mL of concentrated hydrochloric acid was heated at reflux for 12 h and then was cooled to room temperature and concentrated. Trituration with ether gave 0.8 g of a tacky orange solid that was dissolved in 2 mL of water and treated with 0.6 g of sodium carbonate, 15 mL of methylene chloride, and 0.4 mL (0.003 mol) of p-trifluorotolylisocyanate. After stirring 12 h at room temperature, the reaction mixture was poured into water and the aqueous layer was extracted twice with methylene chloride. The combined organic layers were washed with water, dried over anhydrous magnesium sulfate, filtered and concentrated to give 0.9 g of a yellow solid melting at 157°– 161° C. 200 MHz. ¹H NMR (CDCl₃): δ3.68 (d, 1H), 4.2–4.3 (overlapping doublets, 2H), 4.65 (d, 1H), 5.2–5.35 (m, 3 lines, 2H), 6.01 (dd, 1H), 6.95–7.05 (m, 2H), 7.62 (apparent q, 4H), 7.75 (d, 1H), 8.18 (br s, 1H).

Step G: 7-Chloro-2,3,3a,4-tetrahydro-3a-oxiranyl-N-[4-(trifluoromethyl)phenyl][1]benzopyrano[4,3c]pyrazole-2-carboxamide The compound, m-chloroperbenzoic acid (0.7 g of 50% by weight material, 0.002 mol), was added to a solution of 0.3 g (0.0007 mol) of the product from Step F and 0.7 mL of chloroform. The resulting mixture was stirred at room temperature for 24 h and then was partitioned between 25 mL of methylene chloride and 25 mL of saturated sodium bicarbonate solution. The aqueous layer was extracted with two 15 mL portions of methylene chloride and the combined organic layers were washed with saturated sodium bicarbonate solution and then twice with saturated sodium thiosulfate solution, dried over anhydrous magnesium sulfate and concentrated. Flash chromatography on silica gel using 5:2 hexane-EtOAc gave 0.06 g of a solid melting at 187°–190° C. 200 MHz ¹H NMR (CDCl₃): δ2.65 (m, 1H), 2.75 (m, 1H), 3.35 (m, 1H), 3.50 (d, 1H), 4.06 (d, 1H) 4.26 (d, 1H), 4.75 (d, 1H), 7.0–7.1 (m, 2H), 7.60 (apparent q, 4H), 7.75 (d, 1H), 8.1 (brs, 1H).

Further elution with 1:1 hexane-EtOAc gave 0.02 g of the diastereomer as a solid melting at 79°–81° C. 200 MHz ¹H NMR (CDCl₃): δ2.78 (m, 2H), 3.22 (m, 1H), 3.61 (d, 1H), 4.20–4.28 (overlapping doublets, 2H) 4.63 (d, 1H), 7.0–7.1 (m, 2H), 7.62 (apparent q, 4H), 7.75 (d, 1H), 8.1 (brs, 1H).

EXAMPLE 3

Step A: 2-chloro-5-(1-methylethenyl)thiophene

A solution of 80 mL of 3M methyl magnesium bromide in ether was added to a solution of 32 g of 2-acetyl-5-chlorothiophene in 400 mL of ether at 0° to 10° C. After being stirred for 1 hour at 25° C., the reaction mixture was poured onto saturated aq $NH_4Cl$, washed with brine, dried ($MgSO_4$), and concentrated. The crude carbinol was dissolved in 400 mL of 1-chlorobutane, 0.5 g of potassium hydrogen sulfate was added, and the mixture was heated at reflux with a water separator until the distillate was clear. The reaction mixture was washed with aq. $NaHCO_3$, dried ($MgSO_4$), and concentrated after first adding 0.1 g of 4-t-butyl catechol. Distillation at 90° at aspirator pressure afforded the title compound as a yellow oil. $^1$H NMR ($CDCl_3$): $\delta 2.08$ (s, 3H), 4.95 (s, 1H), 5.25 (s, 1H), 6.77 (s, 2H).

Step B: 2-[[2-(5-chloro-2-thienyl)-2-propenyl]-oxy-[-4-(trifluoromethyl)benzaldehyde.

A solution containing 10 g of the product from Step A, 10 g of N-chlorosuccinimide, 0.8 g of diphenyl diselenide, and 0.5 mL of pyridine in 100 mL of dichloromethane was allowed to stir at 25° C. for 20 hours. The mixture was washed with water, brine, dried ($MgSO_4$), concentrated, and chromatographed on silica gel with hexanes to provide 6.9 g of an oil which consisted of an approximately 1:1 mixture of vinylic and allylic chlorides by analysis by NMR. The allylic chloride had signals at $\delta$ ($CDCl_3$) 4.34 (s, 2), 5.32 (s, 1), 5.46 (s, 1), and 6.78 (s, 2).

To a solution of 6.8 g of this mixture in 15 mL of DMF was added 3.0 g of 4-trifluoromethyl salicylaldehyde, 3.0 g of potassium carbonate (anh.), and 0.2 g of sodium iodide, and the mixture was stored for 20 hours at 25° C. After adding 100 mL of water, the product was extracted with ethyl acetate, washed with aq NaOH, brine, dried ($MgSO_4$), and concentrated. The residue was chromatographed (10% EtOAc in hexane/silica gel) to provide 1.9 g of the title compound as a yellow solid, $^1$H NMR ($CDCl_3$): $\delta 4.98$ (s, 2H), 5.39 (s, 1H), 5.61 (s, 1H), 6.87 (ABq, 2H), 7.3 (m, 2H), 7.98 (d, 1H), 10.5 (s, 1H).

Step C: diethyl [3a-(5-chloro-2-thienyl)-2,3,3a,4-tetrahydro-7-(trifluoromethyl)-[1]benzopyrano[4,3-c]pyrazol-2-yl]phosphonate A solution of 2.5 g of the product from Step B and 1.5 g of diethyl phosphorohydrazidate in 20 mL of ethanol containing 2 drops of glacial acetic acid was kept for 1 hour at 25°, concentrated and extracted with ether, washing with water and brine, and drying with $MgSO_4$. The dried and concentrated product(3 g) was redissolved in 200 mL of dichloromethane, cooled to 0° C., then, 1.2 g of N-bromosuccinimide and 0.6 g of triethylamine was added and the mixture was stirred for 15 minutes at 0°. The mixture was allowed to warm to room temperature, washed with aq. $NaHCO_{3,}$ 1 N HCl and brine, dried ($MgSO_4$), concentrated and chromatographed (EtOAc/silica gel) to afford 0.9 g of the product as a gum. 1H NMR ($CDCl_3$) $\delta 1.37$ (m, 6H), 8.8 (d of d, 1H), 4.2 (m, 5H), 4.4 (d, 1H), 4.93 (d, 1H), 6.8 (ABq, 2H), 7.2 (m, 2H), 7.95 (1H).

Step D: 3a-(5-chloro-2-thienyl)-3a,4-dihydro-7-(trifluoromethyl)-N-[4-(trifluoromethyl )phenyl][1 ]benzopyrano[4,3-cl-pyrazole-2-(3H)-carboxamide To a solution of 0.9 g of the product from Step C in 10 mL of ethanol was added 0.5 mL of chlorotrimethylsilane and the mixture was heated at reflux for 20 hours. After concentration and trituration there was obtained 0.4 g of the HCl salt of the dephosphonylated product as a solid. $^1$H NMR ($Me_2SO-d_6$): $\delta 3.6$ (ABq; 2H), 4.5 (d, 1H), 5.0 (d, 1H), 6.6 (broad s), 6.9 (ABq, 2H), 7.3 (m, 2H), 7.83 (d, 1H).

A mixture of 0.3 g of this pyrazole product, 20 mL of $CH_2Cl_2$, 1 mL of saturated aq $NaHCO_3$, and 0.15 g of 4-trifluoromethylphenyl isocyanate was stirred at 25° C. for 10 minutes. The organic layer was dried ($MgSO_4$), concentrated, and triturated with $Et_2O$/hexane to provide 0.3 g of the title compound, mp 184°–187° . $^1$H NMR ($CDCl_3$): $\delta 3.96$ (d, 1H), 4.45 (d, 2H), 5.00 (d, 1H), 6.8 (ABq, 2H), 7.3 (m, 2H), 7.65 (ABq, 4H), 8.0 (d, 1H), 8.2 (brs, 1H).

EXAMPLE 4

Step A: 2-[(2-cyclohexen-1-)oxy]-4-(trifluoromethyl)benzaldehyde

To a solution of 3.6 g (0.026 moles) of $K_2CO_3$ in 75 mL of DMF was added 5.0 g (0.026 moles) of 4-trifluoromethyl-2-hydroxybenzaldehyde and 3.5 g (0.032 moles) of 3-bromo cyclohex-1-ene. The reaction mixture was heated at 70° C. for 5h, cooled to room temperature, poured into ice cold 5% HCl (200 mL), extracted with ethyl acetate (3×75 mL), washed organic phase with 1 N NaOH (2×50 mL), and with brine (100 mL), dried over anhydrous magnesium sulfate, filtered and concentrated in vacuo to afford 4.3 g of an oil. $^1$H NMR ($CDCl_3$): $\delta 1.4$–2.2 (m, 6H), 4.98 (m, 1H), 5.7–6.1 (m, 2H), 7.21 (d, 1H), 7.25 (s, 1H), 7.92 (d, 1H), 10.5 (1H).

Step B: Diethyl[[2-[2-cyclohexen-1-yl)oxy]-4-(trifluoromethyl)phenyl]methylene]phosphorohydrazidate To 4.3 g (0.019 mol) of the product obtained from Step A was added 50 mL of ether and 3.94 g (0.023 moles) of diethyl phosphorylhydrazidate. The reaction mixture was stirred at room temperature for 1 h, added 100 mL of ethyl acetate and extracted with brine (100 mL), dried over anhydrous magnesium sulfate, filtered and concentrated under vacuum to afford 6.6 g of an oil. $^1$H NMR ($CDCl_3$): $\delta 1.36$ (t, 6H), 1.6–2.2 (m, 6H), 4.18 (m, 4H), 4.84 (m, 1H), 5.88–6.04 (m, 2H), 7.0–7.25 (m, 3H), 7.99 (d, 1H), 8.12 (s, 1H). IR (neat) 3100,1030 $cm^{-1}$.

Step C: 2a,3,4,5,5a,10c-Hexahydro-8-(trifluoromethyl)-N-[4-(trifluoromethyl)phenyl]-2H-[1]benzopyrano[4,3,2-cd]-indazole-2-carboxamide To 6.6 g (0.018 moles) of the product obtained from Step B was added 2.8 g (0.021 moles) of N-chlorosuccinimide and 150 mL of methylene chloride. 2.7 g (0.027 moles) of triethylamine was dissolved in 50 mL methylene chloride and added dropwise over 1 h while maintaining the reaction temperature at room temperature. The reaction mixture was extracted with 5% HCl (150 mL) and water (150 mL), dried over anhydrous magnesium sulfate, filtered and concentrated under vacuo to afford 6.6 g of a viscous oil which was dissolved in 60 mL of methanol and 5.8 mL of concentrated HCl. The reaction mixture was heated at reflux for 2 h, cooled and concentrated under vacuum, triturated with ether and the solid was filtered to afford 3.6 g of a yellow solid. Then, 1.8 g (0.0063 moles) of this solid was dissolved in a solution of 50 mL of ethyl acetates and 50 mL of water and 0.870 g (0.0063 moles) of $K_2CO_3$ and 1.2 g (0.0063 moles) of $\alpha,\alpha,\alpha$-trifluoro-p-tolyl isocyanate was added. The reaction mixture was stirred for 0.5 h, extracted with ethyl acetate (3×75 mL), washed with brine (100 mL) dried over anhydrous magnesium sulfate, filtered and concentrated under vacuum to afford a yellow solid. The solid was chromatographed on silica gel using 25% THF/75% hexane to afford 0.970 g of a white solid, m.p. 194°–195° C. $^1$H NMR (CDCl$_3$): δ1.05 (m, 1H), 1.35 (m, 2H), 1.65 (m, 1H), 2.15 (m, 1H), 2.41 (m, 1H), 3.65 (t, 1H), 4.78 (t, 1H), 4.80 (t, 1H), 7.23 (s, 1H), 7.24 (d, 1H), 7.62 (ABq, 4H), 7.99 (d, 1H), 8.19 (s, 1H), I.R. (nujol) 3390, 1691cm$^{-1}$.

EXAMPLE 5

2-(2,3,3A.8A-Tetrahydrocyclopent-((A))inden-8(1H)-ylidene-N-((4-(trifluoromethyl)phenyl))hydrazinecarboxamide The compound, 1:2:3:3a:8:8:a-hexahydrocyclopent[a]inden-8-one, (J. Chem. Soc. 3325 (1957)) (3.0 g) was treated with hydrazine hydrate (1.5 mL) and ethanol (20 mL). The mixture was refluxed for 3.5 h and concentrated to dryness. The residue was dissolved in methylene chloride (30 mL) and washed with water. The dried organic layer was concentrated. One third of the residue was dissolved in Et$_2$O (10 mL) and treated with p-trifluoromethylphenyl isocyanate (0.8 mL). An exothermic reaction ensued and a white precipitate was formed. After 1 h, the mixture was filtered and washed with ethyl ether to give the product (1.3 g) mp 214°–215° C. $^1$H NMR (CDCl$_3$): δ8.5 (NH), 8.3 (NH), 7.7–7.2 (Ar, M), 3.8 and 3.4 (M, CH$_2$) 2.1–1.2 (CH$_2$X$_3$).

EXAMPLE 6

Step A 2-Nitro-4-(trifluoromethyl)benzonitrile

A mixture of 45.0 g (0.20 mol) of 1-chloro-2-nitro-4-(trifluoromethyl)benzene, 39.4 g (0.44 mol) cuprous cyanide, 6.4 g (0.040 mol) bromine, 3.2 (0.040 mol) of pyridine, and 200 mL of dimethylformamide was heated at reflux for 4 hours. Alter cooling the mixture to 20° C., 200 mL of water, 75 g of ferric chloride and 60 mL of concentrated hydrochloric acid were added. The mixture was extracted with three 500 mL portions of toluene. The combined toluene extracts were washed with water, dried over anhydrous magnesium sulfate, and the toluene was evaporated. The residue (33 g) crystallized on standing.

Recrystallization from a mixture of chlorobutane and cyclohexane yielded a colorless solid melting at 43°–45° C. The IR (neat) spectra displays a strong band at 4.5 m.

Step B 2-Methoxy-4-(trifluoromethyl)benzonitrile

Twenty-five percent sodium methoxide in methanol (24.3 g, 11 mol) was added dropwise to a stirred mixture of 19 g (0.091 mol) 2-nitro-4-(trifluoromethyl)benzonitrile and 100 mL of methanol at 20°–30° C. After 1 hour at 25° C., 100 mL of water was added. The solids were collected on a filter and washed with water. The solids were dried to yield 12.5 g of product melting at 59°–61° C. $^1$H NMR (CDCl$_3$) δ4.00 (s, 3H), 7.2–7.7 (3H).

Step C 2-Methoxy-4-(trifluoromethyl)benzaldehyde

Diisobutylaluminum hydride (1.5M in toluene, 35 mL, 0.05 mol) was added over a 1 hour period to a mixture of 10.4 g (0.05 mol) 2-methoxy-4-(trifluoromethyl)benzonitrile and 50 mL toluene at −10° C. The mixture was agitated for 3 hours at 20°–25° C. and then poured into a mixture of 15 mL of concentrated hydrochloric acid and 50 mL of water at 0°–5° C. The mixture was extracted with three 50 mL portions of toluene. The combined extracts were washed with water, dried over anhydrous magnesium sulfate, filtered, and evaporated. An oil (10.3 g) was obtained which, according to glc analysis, consisted of about 90% of the aldehyde, 4% of unreacted nitrile and 6% of the benzylamine. The infrared spectrum exhibited a strong band at 5.9μ and only a very weak band at 4.5μ. Recrystallization from cyclohexane yielded colorless crystals melting at 54°–55° C.

$^1$H NMR (CDCl$_3$) δ4.00 (s, 3H), 7.22 (s, 1H), 7.30 (d, 1H), 7.92 (d, 1H), 10.49 (s, 1H).

Step D 2-Hydroxy-4-(trifluoromethyl)benzaldehyde

A mixture of 10.0 g (0.042 mol) 2-methoxy-4-(trifluoromethyl)benzaldehyde, 5.3 g (0.126 mol) lithium chloride, and 50 mL of dimethylformamide was heated at 155° C. for 3 hours. The reaction mass was cooled, diluted with 100 mL of water, acidified with hydrochloric acid, and then extracted three times with 100 mL of ether. The ether extracts were washed with water, dried over anhydrous magnesium sulfate, and evaporated to provide 6.8 g of the product as an oil.

$^1$H NMR (CDCl$_3$) δ7.01–7.88 (m, 4H), 11.16 (s, 1H).

Step E Methyl 2-[[2-formyl-5-(trifluoromethyl)phenoxy]methyl]-2-propenoate

A mixture of 19.0 g (0.10 mol) 2-hydroxy-4-(trifluoromethyl)benzaldehyde, 13.8 g potassium carbonate, 19.6 g (0.11 mol) methyl(2-bromomethyl)-2-propenoate and 75 mL of dimethylformamide was heated at 50° C. for 1 hour. After cooling to 20° C., 100 mL of water was added. The solids were collected on a filter, washed with water, and dried to yield 22.4 g of a colorless solid. The product was recrystallized from cyclohexane to yield a colorless solid melting at 77°–79° C.

$^1$H NMR (CDCl$_3$) δ3.84 (s, 3H), 4.92 (t, 2H), 6.06 (q, 1H), 6.50 (d, 1H), 7.26 (s, 1H), 7.32 (d, 1H), 7.96 (d, 1H), 10.53 (s, 1H).

Step F Methyl 2-[[2-[[(diethoxyphosphinyl)hydrazonolmethyl]-5-(trifluoromethyl)phenoxy]methyl]-2-propenoate To a mixture of 14.4 g (0.050 mol) of the product of Step E and 50 mL of diethylether, 13.2 g (0.052 mol, assay 66%) of diethyl phosphorohydrazidate was added at 25° C. After agitating for 2 hours, the solids were collected on a falter and washed with 25 mL of ether, then with water. The solids were dried to yield 18.4 g of a colorless solid melting at 143°–144° C.

Step G Methyl 2-(diethoxyphosphinyl)-2,3,3a,4-tetrahydro-7-(trifluoromethyl)[1]benzopyrano[4,3-c]pyrazole-3a-carboxylate To a mixture of 21.9 g (0.050 mol) of the product of Step F, 7.4 g (0.055 mol) of N-chlorosuccinimide and 750 mL of methylene chloride were added, and the mixture was heated to reflux. A mixture of 7.5 g (0.07 mol) triethylamine and 50 mL of methylene chloride was added over a 4 hour period. The reaction mass was refluxed for an additional 1 hour. After cooling to 25° C., the methylene chloride solution was washed three times with 150 mL of water. The methylene chloride solution was dried with magnesium sulfate, filtered, and the solvent was evaporated. An oil remained (24 g) which solidified upon standing. The solid was recrystallized from a mixture of cyclohexane and ethyl acetate to yield a colorless solid melting at 85°–86° C.

Step H Methyl 2,3,3a,4-tetrahydro-7-(trifluoromethyl)[1]benzopyrano[4,3-c]pyrazole-3a-carboxylate,hydrochloride A mixture of the product of Step G (38 g, 0.087 mol) 200 mL of methanol, and 18 g (0.50 mol) hydrogen chloride was heated at reflux (66° C.) for 2½ hours. The solution was concentrated, toluene (50 mL) was added to the residue and, the mixture concentrated again. Another 50 mL toluene was added and evaporated a second time. After adding 100 mL of toluene, the slurry was chilled, and then filtered. The solid was washed with toluene, then hexanes to yield 26 g of a pale yellow product, m.p. 175°–176° C., dec. Recrystallization from a mixture of tetrahydrofuran and methanol gave a colorless solid, m.p. 185°–186° C., dec.

Step I Methyl 2-[[(6-chloro-3-pyridinyl)amino]carbonyl]-2,3-dihydro-7-(trifluoromethyl)[1]benzopyrano[4,3-c]pyrazole-3a(4H)-carboxylate To a solution of 0.15 g (0.0005 mol) of bis(trichloromethyl)carbonate, 20 mL of methylene chloride and 0.39 mL (0.0048 mol) of pyridine was added 0.5 g (0.0015 mol) of the product from Step H at 0° C. The resulting mixture was stirred at 0° C. for 2 hours and then 0.21 g (0.0016 mol) of 5-amino-2-chloro pyridine was added. The resulting mixture was stirred at room temperature for 12 hours and then 10 mL of ethanol followed by 3 g of silica gel were added and the solvent was removed. Flash chromatography of the residue on silica gel using 2:1 hexanes-EtOAc gave 0.28 g of an off-white solid that melted at 236°–238° C. $^1$H NMR (CDCl$_3$, 200 MHz) δ3.77 (s, 3H), 3.85 (d, 1H), 4.24 (d, 1H), 4.53 (d, 1H), 5.07 (d, 1H), 7.20–7.35 (m, 3H), 7.98 (d, 1H), 8.02 (s, 1H), 8.12 (dd, 1H), 8.42 (d, 1H).

EXAMPLE 7

Methyl 2,3-dihydro-7-(trifluoromethyl)-2-[[[5-(trifluoromethyl)-2-pyridinyl]amino]carbonyl][1]benzopyrano[4,3-c]pyrazole-3a (4H)-carboxylate Application of the procedure described in Step I of Example 6, increasing the amounts of reagents by a factor of 1.3 and substitution of 2-amino-5-trifluoromethyl pyridine afforded 0.14 g of s white solid, mp 194°–195° C.

$^1$H NMR (CDCl$_3$, 200 MHz) δ3.77 (s, 3H), 3.83 (d, 1H), 4.25 (d, 1H), 4.55 (d, 1H), 5.08 (d, 1H), 7.22 (s, 1H), 7.33 (d, 1H), 7.91 (d, 1H), 7.99 (d, 1H) 8.28 (d, 1H), 8.55 (s, 1H), 8.85 (s, 1H).

EXAMPLE 8

Methyl 2-[[(5-chloro-2-pyridinyl)amino]carbonyl]-2,3-dihydro-7-(trifluoromethyl)[1]benzopyrano[4,3-c]pyrazole-3a(4H)-carboxylate Application of the procedure described in Step I of Example 6, increasing the mounts of reagents by a factor of 1.5 and substitution of 2-amino-5-chloropyridine gave 0.42 g of a white solid, mp 196°–198° C.

$^1$H NMR (CDCl$_3$, 200 MHz) δ3.76 (s, 3H), 3.82 (d, 1H), 4.23 (d, 1H), 4.55 (d, 1H), 5.05 (d, 1H), 7.21 (s, 1H), 7.32 (d, 1H), 7.68 (dd, 1H), 7.98 (d, 1H), 8.13 (d, 1H), 8.25 (d, J<1Hz, 1H), 8.65 (s, 1H),

EXAMPLE 9

Methyl 2-[[(5-bromo-2-pyridinyl)amino]carbonyl]-2,3-dihydro-7-(trifluoromethyl)[1]benzopyrano[4,3-c]-pyrazole-3a(4H)-carboxylate Application of the procedure described in Step I of Example 6, increasing the amounts of reagents by a factor of 1.5 and substitution of 2-amino-5-bromopyridine gave 0.40 g of a white solid, mp 179°–181° C. $^1$H NMR (CDCl$_3$, 200 MHz) δ3.76 (s, 3H), 3.82 (d, 1H), 4.22 (d, 1H), 4.52 (d, 1H), 5.05 (d, 1H), 7.22 (s, 1H), 7.30 (d, 1H), 7.80 (dd, 1H), 7.98 (d, 1H), 8.05 (d, 1H), 8.25 (d, J<1 Hz, 1H), 8.65 (brs, 1H).

EXAMPLE 10

1-(4-Chlorophenyl)-N-(6-chloro-3-pyridinyl)-5-(4-fluorophenyl)-4,5-dihydro-1H-pyrazole-3-carboxamide A solution of 0.9 g of 1-(4-chlorophenyl)-5-(4-fluorophenyl)-4,5-dihydro-1H-pyrazole-3-carbonyl chloride in 10 mL of THF was added to a solution of 0.4 g of 5-amino-2-chloropyridine, 2.0 mL Of triethylamine and 10 mL of THF. The resulting suspension was stirred at room temperature for 2 hours. The solvent was evaporated and the residue was triturated with 10 mL of methanol to afford 0.66 g of the title compound, mp 191°–193° C.

$^1$H NMR (CDCl$_3$, 200 MHz) δ3.15 (dd, 1H), 3.8 (dd, 1H), 5.4 (dd, 1H), 8.7– 7.0 (m, 12H).

EXAMPLE 11

Step A: 1-[1-(bromomethyl)ethenyl]-4-chlorobenzene

A mixture of 31.0 g (0.20 mol) of 4-chloro-α-methylstyrene, 38.0 g (0.21 mol) of N-bromosuccinimide, 3.9 g (0.02 mol) of p-toluenesulfonic acid monohydrate and 610 mL of THF was heated at reflux for 3 h and then concentrated at room temperature. The residue was partitioned between 400 mL of hexanes and 200 mL of H$_2$O, the organic phase was washed twice with 100 mL H$_2$O and dried (MgSO$_4$). Removal of solvent gave 47.8 g of a yellow oil that was used without further purification. $^1$H NMR (CDCl$_3$, 200 MHz) δ4.33 (s, 2H), 5.50 (d, 2H), 7.2–7.5 (m, 5H).

Step B: 4-chloro-2-[[2-(4-chlorophenyl)-2-propenyl]oxy]benzaldehyde

A mixture of 19.2 g (0.083 mol) of the product from Step A, 10.0 g (0.064 mol) of 4-chlorosalicylaldehyde, 17.6 g (0.13 mol) of potassium carbonate and 64 mL of DMF was stirred at RT for 72 h. Resulting mixture treated with 125 mL of H$_2$O and filtered. Solids were washed with several portions of H$_2$O and dried in a vacuum oven at 40° C. to give 21.0 g of a brown solid. $^1$H NMR (CDCl$_3$, 200 MHz) δ4.99 (s, 2H), 5.51 (s, 1H), 5.65 (s, 1H), 7.04–7.07 (m, 2H), 7.25–7.45 (m, 4H), 7.77 (d, 1H), 10.28 (s, 1H).

Step C: diethyl 7-chloro-3a-(4-chlorophenyl)-3a,4-dihydro[1]benzopyrano[4.3-c]pyrazol-2(3H)-yl-phosphonate A mixture of 11.3 g (0.04 mol) of the product from Step B and 73 mL of ether was treated successively with 2.4 mL of glacial acetic acid and 8.0 g (0.05 mol) of diethyl phosphorohydrazidate at 0° C. Resulting mixture was stirred at room temperature for 2.5 h and then filtered to give 7.8 g of a white solid.

A solution of 11.8 g (0.026 mol) of the product from the above procedure and 645 mL of methylene chloride was treated successively with 3.5 g (0.026 mol) of N-chlorosuccinimide and 4.5 mL (0.032 mol) of triethylamine at 0° C. The resulting mixture was allowed to stir at room temperature for 72 h and was then treated with 300 mL H$_2$O. The aqueous layer was extracted with 100 mL methylene chloride and the combined organic layers were washed with 200 mL of 1N HCl, 200 mL of H$_2$O, dried (MgSO$_4$) and concentrated to give 11.3 g of a tacky yellow solid.

$^1$H NMR (CDCl$_3$, 200 MHz) δ1.34 (t, 6H), 3.77 (dd, 1H), 3.93 (d, 1H), 4.0–4.3 (m, 4H), 4.38 (d, 1H), 5.00 (d, 1H), 6.82 (d, 1H), 6.97 (dd, 1H), 7.25 (ABq, 4H), 7.83 (d, 1H).

Step D: 7-chloro-3a-(4-chlorophenyl)-N-(6-chloro-3-pyridinyl)-3a,4-dihydro[1]benzopyrano[4.3-c]pyrazole-2(3H)-carboxamide Concentrated hydrochloric acid (37%, 4.9 mL) was added to a solution of 11.2 g (0.025 mol) of the product from Step C and methanol (148 mL) at room temperature. The resulting solution was heated at reflux for 7 h, cooled to room temperature and concentrated. The resulting brown residue was triturated with Et$_2$O and filtered to give 7.9 g of a light brown solid.

The product from the above procedure (7.9 g) was dissolved in a mixture of 60 mL of chloroform and 20 mL of saturated sodium bicarbonate. The organic layer was dried over anhydrous K$_2$CO$_3$ and filtered. The filtrate was treated with 23 mL of a solution of phosgene in toluene (1.93 M, 0.044 mol) at 0° C. The resulting mixture was stirred at room temperature for 1 hr and then concentrated to give 8.4 g of a brown semisolid that was used without further purification.

A mixture of 1.5 g of the product from the above procedure and 15 mL of CH$_2$Cl$_2$ was treated successively with 1.4 mL of N,N-diisopropyl ethylamine and 0.50 g (0.004 mol) of 5-amino-2-chloropyridine at room temperature. The resulting mixture was stirred for 12 h and then 10 mL of acetone and 4 g of silica gel were added and the mixture was concentrated. The residue was chromatographed on 100 g of silica gel eluting with 2:1 hexanes-EtOAc to give 0.84 g of a pale yellow solid melting at >250° C.

$^1$H NMR (200 MHz, CDCl$_3$) δ3.92 (d, 1H), 4.23 (d, 1H), 4.42 (d, 1H), 5.08 (d, 1H), 6.90 (d, 1H), 7.05 (d, 1H), 7.19–7.35 (m, 5H), 7.82 (d, 1H), 8.08–8.18 (m, 2H), 8.41 (d, 1H).

By the general procedures described herein, or obvious modifications thereof, the compounds of Tables 1 through 14 can be prepared.

In Tables 1–14 the following notations have been used.

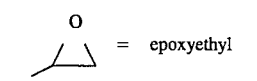 = epoxyethyl

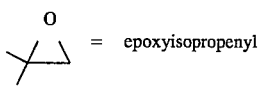 = epoxyisopropenyl

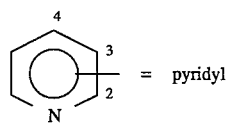 = pyridyl

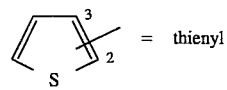 = thienyl

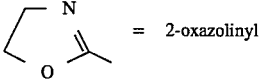 = 2-oxazolinyl

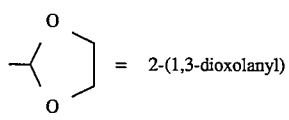 = 2-(1,3-dioxolanyl)

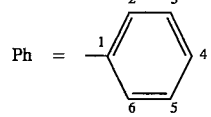

Ph =

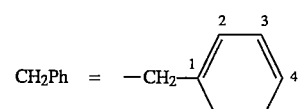

CH$_2$Ph = —CH$_2$—

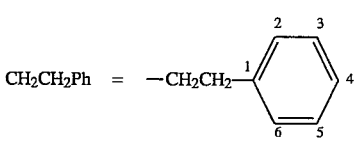

CH$_2$CH$_2$Ph = —CH$_2$CH$_2$—

Et = —CH$_2$CH$_3$ n-Pr = —CH$_2$CH$_2$CH$_3$ i-Pr = —CH(CH$_3$)$_2$

Me = CH$_3$

Ac = 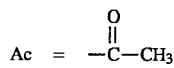

Key for Table 1

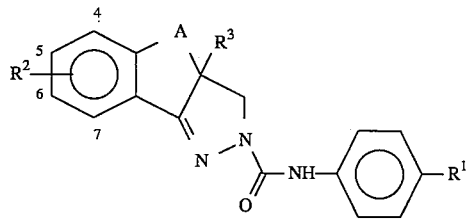

| Group | R$^1$ |
|---|---|
| a | CF$_3$ |
| b | OCF$_3$ |
| c | Cl |
| d | Br |

Compounds of Table 1 wherein A, R$^2$, and R$^3$ are as set out therein can be prepared having the recited values of Groups a through d. That is, for each value of A, R$^2$, and R3 in Table 1, R$^1$ can be CF$_3$, OCF$_3$, Cl or Br. All of said compounds are specifically included within the scope of this invention.

TABLE 1

This Table contains a large number of compounds of Formula I in a format adopted to avoid mechanical reproduction of substituent values that do not vary. For example, the first table entry (where A is CH$_2$CH$_2$, R$^2$ is 4-F and R$^3$ is CN) actually specifies 4 separate and distinct compounds because the key for Table 1 identifies additional substituent values of R$^1$, namely Group a through d for each Table 1 entry.

| A is CH$_2$CH$_2$; R$^2$ is 4-F R$^3$ | A is CH$_2$CH$_2$; R$^2$ is 5-F R$^3$ | A is CH$_2$CH$_2$; R$^2$ is 5-Cl R$^3$ |
|---|---|---|

TABLE 1-continued

This Table contains a large number of compounds of Formula I in a format adopted to avoid mechanical reproduction of substituent values that do not vary. For example, the first table entry (where A is $CH_2CH_2$, $R^2$ is 4-F and $R^3$ is CN) actually specifies 4 separate and distinct compounds because the key for Table 1 identifies additional substituent values of $R^1$, namely Group a through d for each Table 1 entry.

| | | |
|---|---|---|
| CN | CN | CN |
| $NO_2$ | $NO_2$ | $NO_2$ |
| $N_3$ | $N_3$ | $N_3$ |
| Br | Br | Br |
| $NMe_2$ | $NMe_2$ | $NMe_2$ |
| $NHCO_2Me$ | $NHCO_2Me$ | $NHCO_2Me$ |
| epoxyethyl | epoxyethyl | epoxyethyl |
| epoxyisopropenyl | epoxyisopropenyl | epoxyisopropenyl |
| $SiMe_3$ | $SiMe_3$ | $SiMe_3$ |
| SMe | SMe | SMe |
| S(O)Me | S(O)ME | S(O)ME |
| $SO_2Me$ | $SO_2Me$ | $SO_2Me$ |
| $P(O)(OMe)_2$ | $P(O)(OMe)_2$ | $P(O)(OMe)_2$ |
| $CH_2C(O)NMe_2$ | $CH_2C(O)NMe_2$ | $CH_2C(O)NMe_2$ |
| $CH_2SMe$ | $CH_2SMe$ | $CH_2SMe$ |
| $CH_2OCH_2CF_3$ | $CH_2OCH_2CF_3$ | $CH_2OCH_2CF_3$ |
| $CH_2SiMe_3$ | $CH_2SiMe_3$ | $CH_2SiMe_3$ |
| $CH_2NMe_2$ | $CH_2NMe_2$ | $CH_2NMe_2$ |
| $CH_2$-2-pyridyl | $CH_2$-2-pyridyl | $CH_2$-2-pyridyl |
| 2-pyridyl | 2-pyridyl | 2-pyridyl |
| $C(H)=NOCH_3$ | $C(H)=NOCH_3$ | $C(H)=NOCH_3$ |
| 3-pyridyl | 3-pyridyl | 3-pyridyl |
| 2-thienyl | 2-thienyl | 2-thienyl |
| 3-thienyl | 3-thienyl | 3-thienyl |
| 2-oxazolinyl | 2-oxazolinyl | 2-oxazolinyl |
| 2-(1,3-dioxolanyl) | 2-(1,3-dioxolanyl) | 2-(1,3-dioxolanyl) |

| A is $CH_2CH_2$; $R^2$ is 5-$CF_3$ $R^3$ | A is $CH_2CH_2$; $R^2$ is 4-F $R^3$ | A is $OCH_2$; $R^2$ is 5-F $R^3$ |
|---|---|---|
| CN | CN | CN |
| $NO_2$ | $NO_2$ | $NO_2$ |
| $N_3$ | $N_3$ | $N_3$ |
| Br | Br | Br |
| $NMe_2$ | $NMe_2$ | $NMe_2$ |
| $NHCO_2Me$ | $NHCO_2Me$ | $NHCO_2Me$ |
| epoxyethyl | epoxyethyl | epoxyethyl |
| epoxyisopropenyl | epoxyisopropenyl | epoxyisopropenyl |
| $SiMe_3$ | $SiMe_3$ | $SiMe_3$ |
| SMe | SMe | SMe |
| S(O)Me | S(O)Me | S(O)Me |
| $SO_2Me$ | $SO_2Me$ | $SO_2Me$ |
| $P(O)(OMe)_2$ | $P(O)(OMe)_2$ | $P(O)(OMe)_2$ |
| $CH_2C(O)NMe_2$ | $CH_2C(O)NMe_2$ | $CH_2C(O)NMe_2$ |
| $CH_2SMe$ | $CH_2SMe$ | $CH_2SMe$ |
| $CH_2OCH_2CF_3$ | $CH_2OCH_2CF_3$ | $CH_2OCH_2CF_3$ |
| $CH_2SiMe_3$ | $CH_2SiMe_3$ | $CH_2SiMe_3$ |
| $CH_2NMe_2$ | $CH_2NMe_2$ | $CH_2NMe_2$ |
| $CH_2$-2-pyridyl | $CH_2$-2-pyridyl | $CH_2$-2-pyridyl |
| 2-pyridyl | 2-pyridyl | 2-pyridyl |
| 3-pyridyl | 3-pyridyl | 3-pyridyl |
| 2-thienyl | 2-thienyl | 2-thienyl |
| 3-thienyl | 3-thienyl | 3-thienyl |
| 2-oxazolinyl | 2-oxazolinyl | 2-oxazolinyl |
| 2-(1,3-dioxolanyl) | 2-(1,3-dioxolanyl) | 2-(1,3-dioxolanyl) |

| A is $OCH_2$; $R^2$ is 5-Cl; $R^3$ | A is $OCH_2$; $R^2$ is 5-$CF_3$; $R^3$ | A is $NHCH_2$; $R^2$ is 4-F $R^3$ |
|---|---|---|
| CN | CN | CN |
| $NO_2$ | $NO_2$ | $NO_2$ |
| $N_3$ | $N_3$ | $NO_2$ |
| Br | Br | $NMe_3$ |
| $NMe_2$ | $NMe_2$ | $NHCO_2Me$ |
| $NHCO_2Me$ | $NHCO_2Me$ | epoxyethyl |
| epoxyethyl | epoxyethyl | $SiMe_3$ |
| epoxyisopropenyl | epoxyisopropenyl | SMe |
| | | $P(O)(OMe)_2$ |
| $SiMe_3$ | $SiMe_3$ | $CH_2SMe$ |
| SMe | SMe | $CH_2OCH_2CF_3$ |
| S(O)Me | S(O)ME | $CH_2SiMe_3$ |
| $SO_2Me$ | $SO_2Me$ | 2-pyridyl |
| $P(O)(OMe)_2$ | $P(O)(OMe)_2$ | 2-thienyl |
| $CH_2C(O)NMe_2$ | $CH_2C(O)NMe_2$ | |
| $CH_2SMe$ | $CH_2SMe$ | |

| A is $OCH_2$; $R^2$ is 5-Cl; $R^3$ | A is $OCH_2$; $R^2$ is 5-$CF_3$; $R^3$ | A is $NHCH_2$; $R^2$ is 5-F $R^3$ |
|---|---|---|
| $CH_2OCH_2CF_3$ | $CH_2OCH_2CF_3$ | CN |
| $CH_2SiMe_3$ | $CH_2SiMe_3$ | $NO_2$ |
| $CH_2NMe_2$ | $CH_2NMe_2$ | $NMe_2$ |
| $CH_2$-2-pyridyl | $CH_2$-2-pyridyl | $NHCO_2Me$ |
| 2-pyridyl | 2-pyridyl | epoxyethyl |
| 3-pyridyl | 3-pyridyl | $SiMe_3$ |
| 2-thienyl | 2-thienyl | SMe |
| 3-thienyl | 3-thienyl | $P(O)(OMe)_2$ |
| 2-oxazolinyl | 2-oxazolinyl | $CH_2SMe$ |
| 2-(1,3-dioxolanyl) | 2-(1,3-dioxolanyl) | $CH_2OCH_2CF_3$ |
| $C(H)=NOCH_3$ | $C(SCH_3)=N(OCH_3)$ | $CH_2SiMe_3$ |
| $C(CH_3)=NOCH_3$ | $C(H)=NOCH_3$ | 2-pyridyl |
| $C(Cl)=NOCH_3$ | $C(H)=NOCH_2CH_3$ | 2-thienyl |
| $C(CN)=NOCH_3$ | $C(CH_3)=NOCH_3$ | |
| $C(OCH_3)=NOCH_3$ | $C(H)=NOH$ | |

| A is $NHCH_2$; $R^2$ is 5-Cl $R^3$ | A is $N(Me)CH_2$; $R^2$ is 4-F $R^3$ | A is $N(Me)CH_2$; $R^2$ is 5-Cl $R^3$ |
|---|---|---|
| CN | CN | CN |
| $NO_2$ | $NO_2$ | $NO_2$ |
| $NMe_2$ | $NMe_2$ | $NMe_2$ |
| $NHCO_2Me$ | $NHCO_2Me$ | $NHCO_2Me$ |
| epoxyethyl | epoxyethyl | epoxyethyl |
| $SiMe_3$ | $SiMe_3$ | $SiMe_3$ |
| SMe | SMe | SMe |
| $P(O)(OMe)_2$ | $P(O)(OMe)_2$ | $P(O)(OMe)_2$ |
| $CH_2SMe$ | $CH_2SMe$ | $CH_2SMe$ |
| $CH_2OCH_2CF_3$ | $CH_2OCH_2CF_3$ | $CH_2OCH_2CF_3$ |
| $CH_2SiMe_3$ | $CH_2SiMe_3$ | $CH_2SiMe_3$ |
| 2-pyridyl | 2-pyridyl | 2-pyridyl |
| 2-thienyl | 2-thienyl | 2-thienyl |

| A is $NHCH_2$; $R^2$ is 5-$CF_3$ $R^3$ | A is $N(Me)CH_2$; $R^2$ is 5-F $R^3$ | A is $N(Me)CH_2$; $R^2$ is 5-$CF_3$ $R^3$ |
|---|---|---|
| CN | CN | CN |
| $NO_2$ | $NO_2$ | $NO_2$ |
| $NMe_2$ | $NMe_2$ | $NMe_2$ |
| $NHCO_2Me$ | $NHCO_2Me$ | $NHCO_2Me$ |
| epoxyethyl | epoxyethyl | epoxyethyl |
| $SiMe_3$ | $SiMe_3$ | $SiMe_3$ |
| SMe | SMe | SMe |
| $P(O)(OMe)_2$ | $P(O)(OMe)_2$ | $P(O)(OMe)_2$ |
| $CH_2SMe$ | $CH_2SMe$ | $CH_2SMe$ |
| $CH_2OCH_2CF_3$ | $CH_2OCH_2CF_3$ | $CH_2OCH_2CF_3$ |
| $CH_2SiMe_3$ | $CH_2SiMe_3$ | $CH_2SiMe_3$ |
| 2-pyridyl | 2-pyridyl | 2-pyridyl |
| 2-thienyl | 2-thienyl | 2-thienyl |
| $C(H)=NOCH_3$ | $C(CH_3)=NOCH_3$ | $C(OCH_3)=NOCH_3$ |

KEY FOR TABLE 2

[Structure: benzene ring with positions 4,5,6,7 labeled, substituents $R^2$ on ring, A-$R^3$ group, and C(=O)-NH-phenyl-$R^1$ chain with N=N linkage]

| Group | $R^1$ |
|---|---|
| a | $CF_3$ |
| b | $OCF_3$ |

Compounds of Table 2 wherein A, $R^2$, and $R^3$ are as set out therein can be prepared having the recited values of Groups a through b. That is, for each value of A, $R^2$ and $R^3$, $R^1$ can be $CF_3$ or $OCF_3$. All of said compounds are specifically included within the scope of this invention.

TABLE 2

This Table contains a large number of compounds of Formula I in a format adopted to avoid mechanical reproduction of substituent values that do not vary. For example, the first table entry (where A is $CH_2CH_2$, $R^2$ is 5-F and $R^3$ is CN) actually specifies 2 separate and distinct compounds because the key for Table 2 identifies additional substituent values of $R^1$, namely Groups a and b for each Table 2 entry.

| A is $CH_2CH_2$; $R^2$ is 5-F; $R^3$ | A is $CH_2CH_2$; $R^2$ 5-$CF_3$; $R^3$ | A is $OCH_2$; $R^2$ is 5-F; $R^3$ |
|---|---|---|
| CN | CN | CN |
| $NO_2$ | $NO_2$ | $NO_2$ |
| $N_3$ | $N_3$ | $N_3$ |
| Br | Br | Br |
| $NMe_2$ | $NMe_2$ | $NMe_2$ |
| $NHCO_2Me$ | $NHCO_2Me$ | $NHCO_2Me$ |
| epoxyethyl | epoxyethyl | epoxyethyl |
| epoxyisopropenyl | epoxyisopropenyl | epoxyisopropenyl |
| $SiMe_3$ | $SiMe_3$ | $SiMe_3$ |
| SMe | SMe | SMe |
| S(O)Me | S(O)Me | S(O)ME |
| $SO_2Me$ | $SO_2Me$ | $SO_2Me$ |
| $P(O)(OMe)_2$ | $P(O)(OMe)_2$ | $P(O)(OMe)_2$ |
| $CH_2C(O)NMe_2$ | $CH_2C(O)NMe_2$ | $CH_2C(O)NMe_2$ |
| $CH_2SMe$ | $CH_2SMe$ | $CH_2SMe$ |
| $CH_2OCH_2CF_3$ | $CH_2OCH_2CF_3$ | $CH_2OCH_2CF_3$ |
| $CH_2SiMe_3$ | $CH_2SiMe_3$ | $CH_2SiMe_3$ |
| $CH_2NMe_2$ | $CH_2NMe_2$ | $CH_2NMe_2$ |
| $CH_2$-2-pyridyl | $CH_2$-2-pyridyl | $CH_2$-2-pyridyl |
| 2-pyridyl | 2-pyridyl | 2-pyridyl |
| 3-pyridyl | 3-pyridyl | 3-pyridyl |
| 2-thienyl | 2-thienyl | 2-thienyl |
| 3-thienyl | 3-thienyl | 3-thienyl |
| 2-oxazolinyl | 2-oxazolinyl | 2-oxazolinyl |
| 2-(1,3-dioxolanyl) | 2-(1,3-dioxolanyl) | 2-(1,3-dioxolanyl) |

| A is $OCH_2$; $R^2$ is 5-$CF_3$; $R^3$ | A is $NHCH_2$; $R^2$ is 5-F; $R^3$ | A is N(Me)$CH_2$; $R^2$ is 5-F; $R^3$ |
|---|---|---|
| CN | CN | CN |
| $NO_2$ | $NO_2$ | $NO_2$ |
| $N_3$ | $NMe_2$ | $NMe_2$ |
| Br | $NHCO_2Me$ | $NHCO_2Me$ |
| $NMe_2$ | epoxyethyl | epoxyethyl |
| $NHCO_2Me$ | $SiMe_3$ | $SiMe_3$ |
| epoxyethyl | SMe | SMe |

TABLE 2-continued

This Table contains a large number of compounds of Formula I in a format adopted to avoid mechanical reproduction of substituent values that do not vary. For example, the first table entry (where A is $CH_2CH_2$, $R^2$ is 5-F and $R^3$ is CN) actually specifies 2 separate and distinct compounds because the key for Table 2 identifies additional substituent values of $R^1$, namely Groups a and b for each Table 2 entry.

| | | |
|---|---|---|
| epoxyisopropenyl | $P(O)(OMe)_2$ | $P(O)(OMe)_2$ |
| $SiMe_3$ | $CH_2SMe$ | $CH_2SMe$ |
| SMe | $CH_2OCH_2CF_3$ | $CH_2OCH_2CF_3$ |
| S(O)Me | $CH_2SiMe_3$ | $CH_2SiMe_3$ |
| $SO_2Me$ | 2-pyridyl | 2-pyridyl |
| $P(O)(OMe)_2$ | 2-thienyl | 2-thienyl |
| $CH_2C(O)NMe_2$ | | |
| $CH_2SMe$ | | |
| $CH_2OCH_2CF_3$ | | |
| $CH_2SiMe_3$ | | |
| $CH_2NMe_2$ | | |
| $CH_2$-2-pyridyl | | |
| 2-pyridyl | | |
| 3-pyridyl | | |
| 2-thienyl | | |
| 3-thienyl | | |
| 2-oxazolinyl | | |
| 2-(1,3-dioxolanyl) | | |

| A is $NHCH_2$; $R^2$ is 5-$CF_3$; $R^3$ | A is N(Me)$CH_2$; $R^2$ is 5-$CF_3$; $R^3$ |
|---|---|
| CN | CN |
| $NO_2$ | $NO_2$ |
| $NMe_2$ | $NMe_2$ |
| $NHCO_2Me$ | $NHCO_2Me$ |
| epoxyethyl | epoxyethyl |
| $SiMe_3$ | $SiMe_3$ |
| SMe | SMe |
| $P(O)(OMe)_2$ | $P(O)(OMe)_2$ |
| $CH_2SMe$ | $CH_2SMe$ |
| $CH_2OCH_2CF_3$ | $CH_2OCH_2CF_3$ |
| $CH_2SiMe_3$ | $CH_2SiMe_3$ |
| 2-pyridyl | 2-pyridyl |
| 2-thienyl | 2-thienyl |

KEY FOR TABLE 3

[Structure: benzene ring with positions 4,5,6,7 labeled, substituent $R^2$, A-$R^3$ and $R^4$ groups, with N-NH-C(=O)-NH-phenyl-$R^1$ chain]

| Group | $R^1$ | A |
|---|---|---|
| a | $CF_3$ | $CH_2$ |
| b | $OCF_3$ | $CH_2$ |
| c | $CF_3$ | O |
| d | $OCF_3$ | O |

Compounds of Table 3 wherein $R^2$, $R^3$ and $R^4$ are as set out therein can be prepared having the recited values of groups a through d. That is, for each value of $R^2$, $R^3$ and $R^4$ in the Table, $R^1$ and A can have the value verified in each of the Groups a through d above. All of said compounds are specifically included within the scope of this invention.

TABLE 3

This Table contains a large number of compounds of Formula I in a format adopted to avoid mechanical reproduction of substituent values that do not vary. For example, the first table entry (where $R^2$ is 5-F, $R^4$ is H and $R^3$ is $NO_2$) actually specifies 4 separate and distinct compounds because the key for Table 3 identifies additional substituent values of $R^1$ and A, namely Groups a and d for each Table 3 entry.

| $R^2$ is 5-F; $R^4$ is H; $R^3$ | $R^2$ is 5-Cl; $R^4$ is H; $R^3$ | $R^2$ is 5-F; $R^4$ is Me; $R^3$ |
|---|---|---|
| $NO_2$ | $NO_2$ | $NO_2$ |
| $N_3$ | $N_3$ | $NHCO_2Me$ |
| Br | Br | epoxyethyl |
| $NHCO_2Me$ | $NHCO_2Me$ | $SiMe_3$ |
| epoxyethyl | epoxyethyl | $P(O)(OMe)_2$ |
| epoxyisopropenyl | epoxyisopropenyl | $CH_2SMe$ |
| $SiMe_3$ | $SiMe_3$ | $CH_2OCH_2CF_3$ |
| $P(O)(OMe)_2$ | $P(O)(OMe)_2$ | $CH_2SiMe_3$ |
| $CH_2C(O)NMe_2$ | $CH_2C(O)NMe_2$ | 2-pyridyl |
| $CH_2SMe$ | $CH_2SMe$ | 2-thienyl |
| $CH_2OCH_2CF_3$ | $CH_2OCH_2CF_3$ | |
| $CH_2SiMe_3$ | $CH_2SiMe_3$ | $R^2$ is 5-Cl; |
| $CH_2NMe_2$ | $CH_2NMe_2$ | $R^4$ is Me; |
| $CH_2$-2-pyridyl | $CH_2$-2-pyridyl | |
| 2-pyridyl | 2-pyridyl | $R^3$ |
| 3-pyridyl | 3-pyridyl | $NO_2$ |
| 2-thienyl | 2-thienyl | $NHCO_2Me$ |
| 3-thienyl | 3-thienyl | epoxyethyl |
| 2-oxazolinyl | 2-oxazolinyl | $SiMe_3$ |
| 2-(1,3-dioxolanyl) | 2-(1,3-dioxolanyl) | $P(O)(OMe)_2$ |
| $C(H)=NOCH_3$ | $C(H)=NOCH_3$ | $CH_2SMe$ |
| $R^2$ is 5-F; $R^4$ is H; $R^3$ | $R^2$ is 5-Cl; $R^4$ is H; $R^3$ | $R^2$ is 5-F; $R^4$ is Me; $R^3$ |
| $CH_2OCH_2CF_3$ | $CH_2OCH_2CF_3$ | $CH_2OCH_2CF_3$ |
| $CH_2SiMe_3$ | $CH_2SiMe_3$ | $CH_2SiMe_3$ |
| 2-pyridyl | 2-pyridyl | 2-pyridyl |
| 2-thienyl | 2-thienyl | 2-thienyl |
| $R^2$ is 5-F; $R^4$ is Ph; $R^3$ | $R^2$ is 5-F; $R^4$ is 4-F-Ph; $R^3$ | |
| $NO_2$ | $NO_2$ | |
| $NHCO_2Me$ | $NHCO_2Me$ | |
| epoxyethyl | epoxyethyl | |
| $SiMe_3$ | $SiMe_3$ | |
| $P(O)(OMe)_2$ | $P(O)(OMe)_2$ | |
| $CH_2SMe$ | $CH_2SMe$ | |
| $CH_2OCH_2CF_3$ | $CH_2OCH_2CF_3$ | |
| $CH_2SiMe_3$ | $CH_2SiMe_3$ | |
| 2-pyridyl | 2-pyridyl | |
| 2-thienyl | 2-thienyl | |
| $R^2$ is 5-Cl; $R^4$ is Ph; $R^3$ | $R^2$ is 5-Cl; $R^4$ is 4-F-Ph; $R^3$ | |
| $NO_2$ | $NO_2$ | |
| $NHCO_2Me$ | $NHCO_2Me$ | |
| epoxyethyl | epoxyethyl | |
| $SiMe_3$ | $SiMe_3$ | |
| $P(O)(OMe)_2$ | $P(O)(OMe)_2$ | |
| $CH_2SMe$ | $CH_2SMe$ | |
| $CH_2OCH_2CF_3$ | $CH_2OCH_2CF_3$ | |
| $CH_2SiMe_3$ | $CH_2SiMe_3$ | |
| 2-pyridyl | 2-pyridyl | |
| 2-thienyl | 2-thienyl | |

KEY FOR TABLE 4

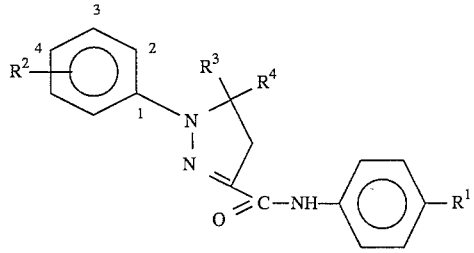

| Group | $R^1$ | $R^2$ |
|---|---|---|
| a | $CF_3$ | 4-Cl |
| b | $OCF_3$ | 4-Cl |
| c | $CF_3$ | 4-F |
| d | $OCF_3$ | 4-F |

Compounds of Table 4 wherein $R^3$ and $R^4$ are as set out therein can be prepared having the recited values of Groups a through d. That is, for each value of $R^3$ and $R^4$ in the Table, $R^1$ and $R^2$ can have the specific values recited in each of Groups a through d above. All of said compounds are compounds of this invention.

TABLE 4

This Table contains a large number of compounds of Formula I in a format adopted to avoid mechanical reproduction of substituent values that do not vary. For example, the first table entry (where $R^4$ is H and $R^3$ is $NO_2$) actually specifies 4 separate and distinct compounds because the key for Table 4 identifies additional substituent values of $R^1$ and $R^2$, namely Groups a through d for each Table 4 entry.

| $R^4$ is H; $R^3$ | $R^4$ is Ph; $R^3$ |
|---|---|
| $NO_2$ | $NO_2$ |
| $N_3$ | $NMe_2$ |
| Br | $NHCO_2Me$ |
| $NMe_2$ | epoxyethyl |
| $NHCO_2Me$ | $SiMe_3$ |
| epoxyethyl | SMe |
| epoxyisopropenyl | $P(O)(OMe)_2$ |
| $SiMe_3$ | $CH_2SMe$ |
| SMe | $CH_2OCH_2CF_3$ |
| S(O)Me | $CH_2SiMe_3$ |
| $SO_2Me$ | $C(H)=NOCH_3$ |
| $P(O)(OMe)_2$ | |
| $CH_2C(O)NMe_2$ | |
| $CH_2SMe$ | |
| $CH_2OCH_2CF_3$ | |
| $CH_2SiMe_3$ | |
| $CH_2NMe_2$ | |
| $R^4$ is Me; $R^3$ | $R^4$ is 4-F-Ph; $R^3$ |
| $NO_2$ | $NO_2$ |
| $NMe_2$ | $NMe_2$ |
| $NHCO_2Me$ | $NHCO_2Me$ |
| epoxyethyl | epoxyethyl |
| $SiMe_3$ | $SiMe_3$ |
| SMe | SMe |
| $P(O)(OMe)_2$ | $P(O)(OMe)_2$ |
| $CH_2SMe$ | $CH_2SMe$ |
| $CH_2OCH_2CF_3$ | $CH_2OCH_2CF_3$ |
| $CH_2SiMe_3$ | $CH_2SiMe_3$ |

KEY FOR TABLE 5

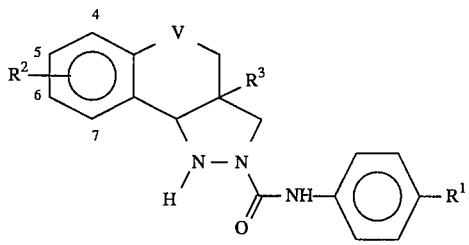

| Group | R¹   | V   |
|-------|------|-----|
| a     | CF₃  | CH₂ |
| b     | OCF₃ | CH₂ |
| c     | CF₃  | O   |
| d     | OCF₃ | O   |

Compounds of Table 5 wherein $R^2$ and $R^3$ are as set out therein can be prepared having the recited values of Groups a through d. That is, for each value of $R^2$ and $R^3$ in the Table, $R^1$ and V can have the values recited in each of the Groups a through d above. All of said compounds are of this invention.

TABLE 5

This Table contains a large number of compounds of Formula I in a format adopted to avoid mechanical reproduction of substituent values that do not vary. For example, the first table entry (where $R^2$ is 5-F and $R^3$ is CN) actually specifies 4 separate and distinct compounds because the key for Table 5 identifies additional substituent values of $R^1$ and V, namely Groups a through d for each Table 5 entry.

| $R^2$ is 5-F; $R^3$ | $R^2$ is Cl; $R^3$ |
|---------------------|--------------------|
| CN                  | CN                 |
| NO₂                 | NO₂                |
| NMe₂                | NMe₂               |
| NHCO₂Me             | NHCO₂Me            |
| epoxyethyl          | epoxyethyl         |
| SiMe₃               | SiMe₃              |
| SMe                 | SMe                |
| P(O)(OMe)₂          | P(O)(OMe)₂         |
| CH₂SMe              | CH₂SMe             |
| CH₂OCH₂CF₃          | CH₂OCH₂CF₃         |
| CH₂SiMe₃            | CH₂SiMe₃           |
| 2-pyridyl           | 2-pyridyl          |
| 2-thienyl           | 2-thienyl          |

KEY FOR TABLE 6

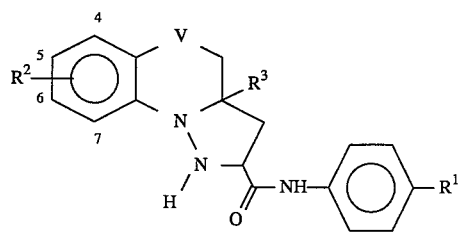

| Group | R¹   | V   |
|-------|------|-----|
| a     | CF₃  | CH₂ |
| b     | OCF₃ | CH₂ |
| c     | CF₃  | O   |
| d     | OCF₃ | O   |

Compounds of Table 6 wherein $R^2$ and $R^3$ are as set out therein can be prepared having the recited values of Groups a through d. That is, for each value of $R^2$ and $R^3$ in the table, $R^1$ and V can have the values recited in Groups a through d above. All of said compounds are of this invention.

TABLE 6

This Table contains a large number of compounds of Formula I in a format adopted to avoid mechanical reproduction of substituent values that do not vary. For example, the first table entry (where $R^2$ is 5-F and $R^3$ is CN) actually specifies 4 separate and distinct compounds because the key for Table 6 identifies additional substituent values of $R^1$ and V, namely Groups a through d for each Table 6 entry.

| $R^2$ is 5-F; $R^3$ | $R^2$ is 5-Cl; $R^3$ |
|---------------------|----------------------|
| CN                  | CN                   |
| NO₂                 | NO₂                  |
| NMe₂                | NMe₂                 |
| NHCO₂Me             | NHCO₂Me              |
| epoxyethyl          | epoxyethyl           |
| SiMe₃               | SiMe₃                |
| SMe                 | SMe                  |
| P(O)(OMe)₂          | P(O)(OMe)₂           |
| CH₂SMe              | CH₂SMe               |
| CH₂OCH₂CF₃          | CH₂OCH₂CF₃           |
| CH₂SiMe₃            | CH₂SiMe₃             |
| 2-pyridyl           | 2-pyridyl            |
| 2-thienyl           | 2-thienyl            |

KEY FOR TABLE 7

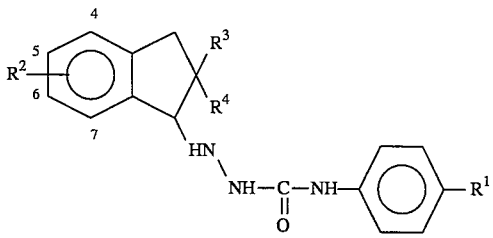

| Group | R¹   | A   |
|-------|------|-----|
| a     | CF₃  | CH₂ |
| b     | OCF₃ | CH₂ |

KEY FOR TABLE 7

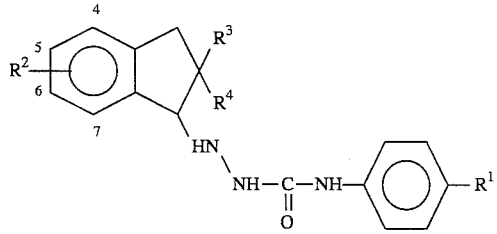

| Group | R¹ | A |
|---|---|---|
| c | CF₃ | O |
| d | OCF₃ | O |

Compounds of Table 7 wherein $R^2$, $R^3$ and $R^4$ are as set out therein can be prepared having the recited values of Groups a through d. That is, for each value of $R^2$, $R^3$ and $R^4$ in the Table, $R^1$ and A can have the values recited in each of the Groups a through d above. All of said compounds are within the scope of this invention.

TABLE 7

This Table contains a large number of compounds of Formula I in a format adopted to avoid mechanical reproduction of substituent values that do not vary. For example, the first table entry (where $R^2$ is 5-F, $R^4$ is H and $R^3$ is CN) actually specifies 4 separate and distinct compounds because the key for Table 7 identifies additional substituent values of $R^1$ and A, namely Groups a through d for each Table 7 entry.

| $R^2$ is 5-F;<br>$R^4$ is H;<br>$R^3$ | $R^2$ is 5-F;<br>$R^4$ is Me;<br>$R^3$ | $R^2$ is 5-F;<br>$R^4$ is Ph;<br>$R^3$ |
|---|---|---|
| CN | CN | CN |
| NO₂ | NO₂ | NO₂ |
| NMe₂ | NMe₂ | NMe₂ |
| NHCO₂Me | NHCO₂Me | NHCO₂Me |
| epoxyethyl | epoxyethyl | epoxyethyl |
| SiMe₃ | SiMe₃ | SiMe₃ |
| SMe | SMe | SMe |
| P(O)(OMe)₂ | P(O)(OMe)₂ | P(O)(OMe)₂ |
| CH₂SMe | CH₂SMe | CH₂SMe |
| CH₂OCH₂CF₃ | CH₂OCH₂CF₃ | CH₂OCH₂CF₃ |
| CH₂SiMe₃ | CH₂SiMe₃ | CH₂SiMe₃ |
| 2-pyridyl | 2-pyridyl | 2-pyridyl |
| 2-thienyl | 2-thienyl | 2-thienyl |

| $R^2$ is 5-F;<br>$R^4$ is 4-F-Ph;<br>$R^3$ | $R^2$ is 5-Cl;<br>$R^4$ is Me;<br>$R^3$ | $R^2$ is 5-Cl;<br>$R^4$ is 4-F-Ph;<br>$R^3$ |
|---|---|---|
| CN | CN | CN |
| NO₂ | NO₂ | NO₂ |
| NMe₂ | NMe₂ | NMe₂ |
| NHCO₂Me | NHCO₂Me | NHCO₂Me |
| epoxyethyl | epoxyethyl | epoxyethyl |

| $R^2$ is 5-F;<br>$R^4$ is 4-F-Ph;<br>$R^3$ | $R^2$ is 5-Cl;<br>$R^4$ is Me;<br>$R^3$ | $R^2$ is 5-Cl;<br>$R^4$ is 4-F-Ph;<br>$R^3$ |
|---|---|---|
| SiMe₃ | SiMe₃ | SiMe₃ |
| SMe | SMe | SMe |
| P(O)(OMe)₂ | P(O)(OMe)₂ | P(O)(OMe)₂ |
| CH₂SMe | CH₂SMe | CH₂SMe |
| CH₂OCH₂CF₃ | CH₂OCH₂CF₃ | CH₂OCH₂CF₃ |
| CH₂SiMe₃ | CH₂SiMe₃ | CH₂SiMe₃ |
| 2-pyridyl | 2-pyridyl | 2-pyridyl |

TABLE 7-continued

This Table contains a large number of compounds of Formula I in a format adopted to avoid mechanical reproduction of substituent values that do not vary. For example, the first table entry (where $R^2$ is 5-F, $R^4$ is H and $R^3$ is CN) actually specifies 4 separate and distinct compounds because the key for Table 7 identifies additional substituent values of $R^1$ and A, namely Groups a through d for each Table 7 entry.

| 2-thienyl | 2-thienyl | 2-thienyl |
|---|---|---|
| $R^2$ is 5-Cl;<br>$R^4$ is H;<br>$R^3$ | $R^2$ is 5-Cl;<br>$R^4$ is Ph;<br>$R^3$ | |
| CN | CN | |
| NO₂ | NO₂ | |
| NMe₂ | NMe₂ | |
| NHCO₂Me | NHCO₂Me | |
| epoxyethyl | epoxyethyl | |
| SiMe₃ | SiMe₃ | |
| SMe | SMe | |
| P(O)(OMe)₂ | P(O)(OMe)₂ | |
| CH₂SMe | CH₂SMe | |
| CH₂OCH₂CF₃ | CH₂OCH₂CF₃ | |
| CH₂SiMe₃ | CH₂SiMe₃ | |
| 2-pyridyl | 2-pyridyl | |
| 2-thienyl | 2-thienyl | |

KEY FOR TABLE 8

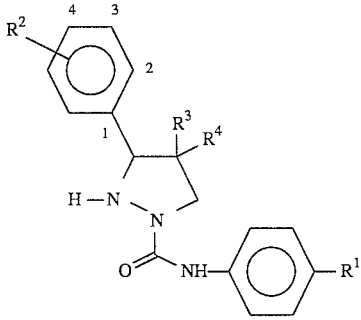

| Group | R¹ | R² |
|---|---|---|
| a | CF₃ | 4-Cl |
| b | OCF₃ | 4-Cl |
| c | CF₃ | 4-F |
| d | OCF₃ | 4-F |

Compounds of Table 8 wherein $R^3$ and $R^4$ are as set out therein can be prepared having the recited values of Groups a through d. That is, for each value of $R^3$ and $R^4$ in the Table, $R^1$ and $R^2$ can have the values recited in Groups a through d above. All of said compounds are of this invention.

TABLE 8

This Table contains a large number of compounds of Formula I in a format adopted to avoid mechanical reproduction of substituent values that do not vary. For example, the first table entry (where $R^4$ is 4-F and $R^3$ is CN) actually specifies 4 separate and distinct compounds because the key for Table 8 identifies additional substituent values of $R^1$ and $R^2$, namely Groups a through d for each Table 8 entry.

| $R^4$ is H;<br>$R^3$ | $R^4$ is Ph;<br>$R^3$ |
|---|---|

TABLE 8-continued

This Table contains a large number of compounds of Formula I in a format adopted to avoid mechanical reproduction of substituent values that do not vary. For example, the first table entry (where $R^4$ is 4-F and $R^3$ is CN) actually specifies 4 separate and distinct compounds because the key for Table 8 identifies additional substituent values of $R^1$ and $R^2$, namely Groups a through d for each Table 8 entry.

| CN | CN |
|---|---|
| $NO_2$ | $NO_2$ |
| $NMe_2$ | $NMe_2$ |
| $NHCO_2Me$ | $NHCO_2Me$ |
| epoxyethyl | epoxyethyl |
| $SiMe_3$ | $SiMe_3$ |
| SMe | SMe |
| $P(O)(OMe)_2$ | $P(O)(OMe)_2$ |
| $CH_2SMe$ | $CH_2SMe$ |
| $CH_2OCH_2CF_3$ | $CH_2OCH_2CF_3$ |
| $CH_2SiMe_3$ | $CH_2SiMe_3$ |
| 2-pyridyl | 2-pyridyl |
| 2-thienyl | 2-thienyl |

| $R^4$ is Me; $R^3$ | $R^4$ is 4-F-Ph; $R^3$ |
|---|---|
| CN | CN |
| $NO_2$ | $NO_2$ |
| $NMe_2$ | $NMe_2$ |
| $NHCO_2Me$ | $NHCO_2Me$ |
| epoxyethyl | epoxyethyl |
| $SiMe_3$ | $SiMe_3$ |
| SMe | SMe |
| $P(O)(OMe)_2$ | $P(O)(OMe)_2$ |
| $CH_2SMe$ | $CH_2SMe$ |
| $CH_2OCH_2CF_3$ | $CH_2OCH_2CF_3$ |
| $CH_2SiMe_3$ | $CH_2SiMe_3$ |
| 2-pyridyl | 2-pyridyl |
| 2-thienyl | 2-thienyl |

KEY FOR TABLE 9

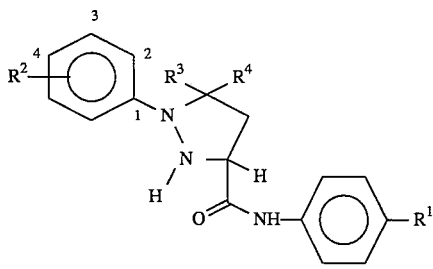

| Group | $R^1$ | $R^2$ |
|---|---|---|
| a | $CF_3$ | 4-Cl |
| b | $OCF_3$ | 4-Cl |
| c | $CF_3$ | 4-F |
| d | $OCF_3$ | 4-F |

Compounds of Table 9 wherein $R^3$ and $R^4$ are as set out therein can be prepared having the recited values of Groups a through d. That is, for each value of $R^3$ and $R^4$ in the Table, $R^1$ and $R^2$ can have the values recited in Groups a through d above. All of said compounds are of this invention.

TABLE 9

This Table contains a large number of compounds of Formula I in a format adopted to avoid mechanical reproduction of substituent values that do not vary. For example, the first table entry (where $R^4$ is H and $R^3$ is CN) actually specifies 4 separate and distinct compounds because the key for Table 9 identifies additional substituent values of $R^1$ and $R^2$, namely Groups a through d for each Table 9 entry.

| $R^4$ is H; $R^3$ | $R^4$ is Ph; $R^3$ |
|---|---|
| CN | CN |
| $NO_2$ | $NO_2$ |
| $NMe_2$ | $NMe_2$ |
| $NHCO_2Me$ | $NHCO_2Me$ |
| epoxyethyl | epoxyethyl |
| $SiMe_3$ | $SiMe_3$ |
| SMe | SMe |
| $P(O)(OMe)_2$ | $P(O)(OMe)_2$ |
| $CH_2SMe$ | $CH_2SMe$ |
| $CH_2OCH_2CF_3$ | $CH_2OCH_2CF_3$ |
| $CH_2SiMe_3$ | $CH_2SiMe_3$ |
| 2-pyridyl | 2-pyridyl |
| 2-thienyl | 2-thienyl |

| $R^4$ is Me; $R^3$ | $R^4$ is 4-F-Ph; $R^3$ |
|---|---|
| CN | CN |
| $NO_2$ | $NO_2$ |
| $NMe_2$ | $NMe_2$ |
| $NHCO_2Me$ | $NHCO_2Me$ |
| epoxyethyl | epoxyethyl |
| $SiMe_3$ | $SiMe_3$ |
| SMe | SMe |
| $P(O)(OMe)_2$ | $P(O)(OMe)_2$ |
| $CH_2SMe$ | $CH_2SMe$ |
| $CH_2OCH_2CF_3$ | $CH_2OCH_2CF_3$ |
| $CH_2SiMe_3$ | $CH_2SiMe_3$ |
| 2-pyridyl | 2-pyridyl |
| 2-thienyl | 2-thienyl |

KEY FOR TABLE 10

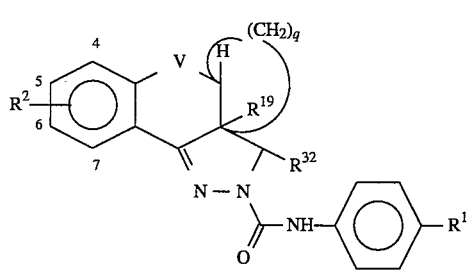

| Group | $R^1$ | V |
|---|---|---|
| a | $CF_3$ | $CH_2$ |
| b | $OCF_3$ | $CH_2$ |
| c | Cl | $CH_2$ |
| d | Br | $CH_2$ |
| e | $CF_3$ | O |
| f | $OCF_3$ | O |
| g | Cl | O |
| h | Br | O |
| i | $CF_3$ | NH |
| j | $OCF_3$ | NH |
| k | $CF_3$ | NMe |
| l | $OCF_3$ | NMe |

Compounds of Table 10 wherein $R^2$, $R^{19}$, $R^{32}$ and q are as set out therein can be prepared having the recited values of Groups a through 1. That is, for each value of $R^2$, $R^{19}$, $R^{32}$ and q in the Table, $R^1$ and V can have the values recited in Groups a through 1 above. Each compound having the recited values for, $R^1$, V, $R^2$, $R^{19}$, $R^{32}$ and q is included within the scope of this invention by the specific designation of its structure.

TABLE 10

This Table contains a large number of compounds of Formula I in a format adopted to avoid mechanical reproduction of substituent values that do not vary. For example, the first table entry (where $R^2$ is 4-F, q is 2 and $R^{19}$ and $R^{32}$ are H) actually specifies 12 separate and distinct compounds because the key for Table 10 identifies additional substituent values of $R^1$ and V, namely Groups a through 1 for each Table 10 entry.

| $R^2$ is 4-F q is 2; | | $R^2$ is 5-CF$_3$ q is 2; | |
|---|---|---|---|
| $R^{19}$ | $R^{32}$ | $R^{19}$ | $R^{32}$ |
| H | H | H | H |
| H | Me | H | Me |
| H | CO$_2$Me | H | CO$_2$Me |
| Me | H | Me | H |
| iPr | H | iPr | H |
| Ph | H | Ph | H |
| CO$_2$Me | H | CO$_2$Me | H |

| $R^2$ is 5-F q is 2; | | $R^2$ is 4-F q is 3; | |
|---|---|---|---|
| $R^{19}$ | $R^{32}$ | $R^{19}$ | $R^{32}$ |
| H | H | H | H |
| H | Me | H | Me |
| H | CO$_2$Me | H | CO$_2$Me |
| Me | H | ME | H |
| iPr | H | iPr | H |
| Ph | H | Ph | H |
| CO$_2$Me | H | CO$_2$Me | H |

| $R^2$ is 5-Cl q is 2; | | $R^2$ is 5-F q is 3; | |
|---|---|---|---|
| $R^{19}$ | $R^{32}$ | $R^{19}$ | $R^{32}$ |
| H | H | H | H |
| H | Me | H | Me |
| H | CO$_2$Me | H | CO$_2$Me |
| Me | H | Me | H |
| iPr | H | iPr | H |
| Ph | H | Ph | H |
| CO$_2$Me | H | CO$_2$Me | H |

| $R^2$ is 5-Cl q is 3; | | $R^2$ is 5-F q is 4; | |
|---|---|---|---|
| $R^{19}$ | $R^{32}$ | $R^{19}$ | $R^{32}$ |
| H | H | H | H |
| H | Me | H | Me |
| H | CO$_2$Me | H | CO$_2$Me |
| Me | H | Me | H |
| iPr | H | iPr | H |
| Ph | H | Ph | H |
| CO$_2$Me | H | CO$_2$Me | H |

| $R^2$ is 5-CF$_3$ q is 3; | | $R^2$ is 5-Cl q is 4; | |
|---|---|---|---|
| $R^{19}$ | $R^{32}$ | $R^{19}$ | $R^{32}$ |
| H | H | H | H |
| H | Me | H | Me |
| H | CO$_2$Me | H | CO$_2$Me |

TABLE 10-continued

This Table contains a large number of compounds of Formula I in a format adopted to avoid mechanical reproduction of substituent values that do not vary. For example, the first table entry (where $R^2$ is 4-F, q is 2 and $R^{19}$ and $R^{32}$ are H) actually specifies 12 separate and distinct compounds because the key for Table 10 identifies additional substituent values of $R^1$ and V, namely Groups a through 1 for each Table 10 entry.

| Me | H | Me | H |
|---|---|---|---|
| iPr | H | iPr | H |
| Ph | H | Ph | H |
| CO$_2$Me | H | CO$_2$Me | H |

| $R^2$ is 4-Fl q is 4; | | $R^2$ is CF$_3$ q is 4; | |
|---|---|---|---|
| $R^{19}$ | $R^{32}$ | $R^{19}$ | $R^{32}$ |
| H | H | H | H |
| H | Me | H | Me |
| H | CO$_2$Me | H | CO$_2$Me |
| Me | H | Me | H |
| iPr | H | iPr | H |
| Ph | H | Ph | H |
| CO$_2$Me | H | CO$_2$Me | H |

KEY FOR TABLE 11

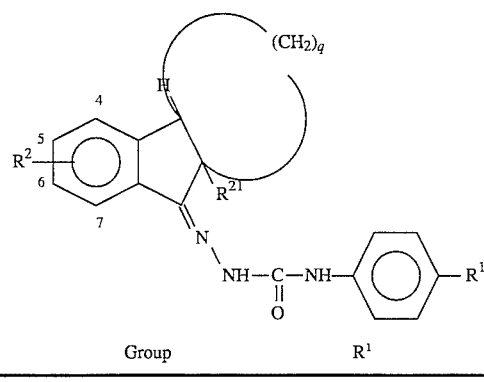

| Group | $R^1$ |
|---|---|
| a | CF$_3$ |
| b | OCF$_3$ |
| c | Cl |
| d | Br |

Compounds of Table 11 wherein $R^2$, $R^{21}$ and q are as set out therein can be prepared having the recited values of Groups a through d. That is, for each value of $R^2$, $R^{21}$, and q in the Table, $R^1$ can have the values recited in Groups a through d above. All of said compounds are of this invention.

TABLE 11

This Table contains a large number of compounds of Formula I in a format adopted to avoid mechanical reproduction of substituent values that do not vary. For example, the first table entry (where $R^2$ is 4-F, q is 3 and $R^{21}$ is H) actually specifies 4 separate and distinct compounds because the key for Table 11 identifies additional substituent values of $R^1$, namely Groups a through d for each Table 11 entry.

| $R^2$ is 4-F; q is 3; $R^{21}$ | $R^2$ is 5-Cl; q is 3; $R^{21}$ | $R^2$ is 4-F; q is 4; $R^{21}$ |
|---|---|---|

TABLE 11-continued

This Table contains a large number of compounds of Formula I in a format adopted to avoid mechanical reproduction of substituent values that do not vary. For example, the first table entry (where $R^2$ is 4-F, q is 3 and $R^{21}$ is H) actually specifies 4 separate and distinct compounds because the key for Table 11 identifies additional substituent values of $R^1$, namely Groups a through d for each Table 11 entry.

| | | |
|---|---|---|
| H | H | H |
| Me | Me | Me |
| iPr | iPr | iPr |
| Ph | Ph | Ph |
| 4-F-Ph | 4-F-Ph | 4-F-Ph |
| $R^2$ is 5-F; q is 3; $R^{21}$ | $R^2$ is 5-$CF_3$; q is 3; $R^{21}$ | $R^2$ is 5-F; q is 4; $R^{21}$ |
| H | H | H |
| Me | Me | Me |
| iPr | iPr | iPr |
| Ph | Ph | Ph |
| 4-F-Ph | 4-F-Ph | 4-F-Ph |
| $R^2$ is 5-Cl; q is 4; $R^{21}$ | $R^2$ is 4-F; q is 5; $R^{21}$ | $R^2$ is 5-Cl; q is 5; $R^{21}$ |
| H | H | H |
| Me | Me | Me |
| iPr | iPr | iPr |
| Ph | Ph | Ph |
| 4-F-Ph | 4-F-Ph | 4-F-Ph |
| $R^2$ is 5-$CF_3$; q is 4; $R^{21}$ | $R^2$ is 5-F; q is 5; $R^{21}$ | $R^2$ is 5-$CF_3$; q is 5; $R^{21}$ |
| H | H | H |
| Me | Me | Me |
| iPr | iPr | iPr |
| Ph | Ph | Ph |
| 4-F-Ph | 4-F-Ph | 4-F-Ph |

KEY FOR TABLE 12

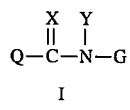

$$Q-\underset{I}{\overset{\overset{X}{\|}}{C}}-\underset{}{\overset{\overset{Y}{|}}{N}}-G$$

| Table | Group | Q |
|---|---|---|
| 12(a) | a | Q-1 (A = $CH_2$, X = O) |
| 12(a) | b | Q-1 (A = $CH_2CH_2$, X = O) |
| 12(a) | c | Q-1 (A = O, X = O) |
| 12(a) | d | Q-1 (A = $OCH_2$, X = O) |
| 12(a) | e | Q-1 (A = S, X = O) |
| 12(a) | f | Q-1 (A = $SCH_2$, X = O) |
| 12(a) | g | Q-1 (A = NH, X = O) |
| 12(a) | h | Q-1 (A = $NHCH_2$, X = O) |
| 12(a) | i | Q-1 (A = N(Me)$CH_2$, X = O) |
| 12(a) | j | Q-1 (A = NMe, X = O) |
| 12(a) | k | Q-1 (A = $NCH_2Ph$, X = O) |
| 12(a) | l | Q-1 (A = N($CH_2Ph$)$CH_2$, X = O) |
| 12(a) | m | Q-1 (A = $OCH_2$, X = S) |
| 12(a) | n | Q-1 (A = $CH_2CH_2$, X = S) |
| 12(a) | o | Q-2 (A = $CH_2$, X = O) |
| 12(a) | p | Q-2 (A = $CH_2CH_2$, X = O) |
| 12(a) | q | Q-2 (A = O, X = O) |
| 12(a) | r | Q-2 (A = $OCH_2$, X = O) |
| 12(a) | s | Q-2 (A = S, X = O) |
| 12(a) | t | Q-2 (A = $SCH_2$, X = O) |
| 12(a) | u | Q-2 (A = NH, X = O) |
| 12(a) | v | Q-2 (A = $NHCH_2$, X = O) |
| 12(a) | w | Q-2 (A = N(Me)$CH_2$, X = O) |
| 12(a) | x | Q-2 (A = NMe, X = O) |
| 12(a) | y | Q-2 (A = $NHC_2Ph$, X = O) |
| 12(a) | z | Q-2 (A = N($CH_2Ph$)$CH_2$, X = O) |
| 12(a) | aa | Q-2 (A = $OCH_2$, X = S) |
| 12(a) | ab | Q-2 (A = $CH_2CH_2$, X = S) |
| 12(a) | ac | Q-2 (A = CHMe, X = O) |
| 12(a) | ad | Q-2 (A = CH(Me)$CH_2$, X = O) |
| 12(a) | ae | Q-2 (A = $CH_2CHCl$, X = O) |
| 12(a) | af | Q-1 (A = CHMe, X = O) |
| 12(a) | ag | Q-1 (A = CH(Me)$CH_2$, X = O) |
| 12(a) | ah | Q-1 (A = $CH_2CHMe$, X = O) |
| 12(a) | ai | Q-1 (A = $CH_2CHCl$, X = O) |
| 12(a) | aj | Q-2 (A = $CH_2CHMe$, X = O) |
| 12(a) | ak | Q-3 (A = $CH_2$, $R^4$ = H, X = O, $Y^1$ = H) |
| 12(a) | al | Q-3 (A = $CH_2CH_2$, $R^4$ = H, X = O, $Y^1$ = H) |
| 12(a) | am | Q-3 (A = CHMe, $R^4$ = H, X = O, $Y^1$ = H) |
| 12(a) | an | Q-3 (A = $CH_2CHMe$, $R^4$ = H, X = O, $Y^1$ = H) |
| 12(a) | ao | Q-3 (A = CH(Me)$CH_3$, $R^4$ = H, X = O, $Y^1$ = H) |
| 12(a) | ap | Q-3 (A = O, $R^4$ = H, X = O, $Y^1$ = H) |
| 12(a) | aq | Q-3 (A = $OCH_2$, $R^4$ = H, X = O, $Y^1$ = H) |
| 12(a) | ar | Q-3 (A = S, $R^4$ = H, X = O, $Y^1$ = H) |
| 12(a) | as | Q-3 (A = $SCH_2$, $R^4$ = H, X = O, $Y^1$ = H) |
| 12(a) | at | Q-3 (A = NH, $R^4$ = H, X = O, $Y^1$ = H) |
| 12(a) | au | Q-3 (A = NMe, $R^4$ = H, X = O, $Y^1$ = H) |
| 12(a) | av | Q-3 (A = $NHCH_2$, $R^4$ = H, X = O, $Y^1$ = H) |
| 12(a) | aw | Q-3 (A = N(Me)$CH_2$, $R^4$ = H, X = O, $Y^1$ = H) |
| 12(a) | ax | Q-3 (A = $NCH_2Ph$, $R^4$ = H, X = O, $Y^1$ = H) |
| 12(a) | ay | Q-3 (A = N($CH_2Ph$)$CH_2$, $R^4$ = H, X = O, $Y^1$ = H) |
| 12(a) | az | Q-3 (A = $CH_2$, $R^4$ = Me, X = O, $Y^1$ = H) |
| 12(a) | ba | Q-3 (A = O, $R^4$ = Me, X = O, $Y^1$ = H) |
| 12(a) | bb | Q-3 (A = O, $R^4$ = H, X = S, $Y^1$ = H) |
| 12(a) | bc | Q-3 (A = $CH_2$, $R^4$ = H, X = S, $Y^1$ = H) |
| 12(a) | bd | Q-3 (A = O, $R^4$ = H, X = O, $Y^1$ = Me) |
| 12(a) | be | Q-3 (A = $CH_2$, $R^4$ = H, X = O, $Y^1$ = Me) |
| 12(a) | bf | Q-3 (A = O, $R^4$ ,Me, X = O, $Y^1$ = Me) |
| 12(a) | bg | Q-3 (A = $CH_2$, $R^4$ = Me, X = O, $Y^1$ = Me) |
| 12(a) | bh | Q-4 ($R^4$ = H, X = O) |
| 12(a) | bi | Q-4 ($R^4$ = H, X = S) |
| 12(a) | bj | Q-4 ($R^4$ = Me, X = O) |
| 12(a) | bk | Q-4 ($R^4$ = Et, X = O) |
| 12(a) | bl | Q-5 ($R^{18}$ = H, V = $CH_2$, X = O) |
| 12(a) | bm | Q-5 ($R^{18}$ = H, V = O, X = O) |
| 12(a) | bx | Q-5 ($R^{18}$ = $CO_2Me$, V = NMe, X = O) |
| 12(a) | by | Q-5 ($R^{18}$ = $SO_2Me$, V = $CH_2$, X = O) |
| 12(a) | bz | Q-5 ($R^{18}$ = $SO_2Me$, V = O, X = O) |
| 12(a) | ca | Q-5 ($R^{18}$ = $SO_2Me$, V = NMe, X = O) |
| 12(a) | cb | Q-5 ($R^{18}$ = Me, V = $CH_2$, X = O) |
| 12(a) | cc | Q-5 ($R^{18}$ = Me, V = O, X = O) |
| 12(a) | cd | Q-5 ($R^{18}$ = Me, V = NMe, X = O) |
| 12(a) | ce | Q-6 ($R^{18}$ = H, V = $CH_2$, X = O) |
| 12(a) | cf | Q-6 ($R^{18}$ = H, V = O, X = O) |
| 12(a) | cg | Q-6 ($R^{18}$ = H, V = NH, X = O) |
| 12(a) | ch | Q-6 ($R^{18}$ = H, V = NMe, X = O) |
| 12(a) | ci | Q-6 ($R^{18}$ = H, V = $NCH_2Ph$, X = O) |
| 12(a) | cj | Q-6 ($R^{18}$ = H, V = S, X = O) |
| 12(a) | ck | Q-6 ($R^{18}$ = H, V = $CHCH_3$, X = O) |
| 12(a) | cl | Q-6 ($R^{18}$ = COMe, V = $CH_2$, X = O) |
| 12(a) | cm | Q-6 ($R^{18}$ = COMe, V = O, X = O) |
| 12(a) | cn | Q-6 ($R^{18}$ = COMe, V = NMe, X = O) |
| 12(a) | co | Q-6 ($R^{18}$ = $CO_2Me$, V = $CH_2$, X = O) |
| 12(a) | cp | Q-6 ($R^{18}$ = $CO_2Me$, V = O, X = O) |
| 12(a) | cq | Q-6 ($R^{18}$ = $CO_2Me$, V = NMe, X = O) |

KEY FOR TABLE 12

$$Q-\overset{\overset{X}{\|}}{C}-\overset{\overset{Y}{|}}{N}-G$$

I

| Table | Group | Q |
|---|---|---|
| 12(a) | cr | Q-6 ($R^{18}$ = $CO_2$Me, V = S, X = O) |
| 12(a) | cs | Q-5 ($R^{18}$ = COMe, V = S, X = O) |
| 12(a) | ct | Q-5 ($R^{18}$ = $CO_2$Me, V = S, X = O) |
| 12(a) | cu | Q-5 ($R^{18}$ = $SO_2$Me, V = S, X = O) |
| 12(a) | cv | Q-5 ($R^{18}$ = Me, V = S, X = O) |
| 12(a) | cw | Q-6 ($R^{18}$ = COMe, V = S, X = O) |
| 12(a) | cx | Q-6 ($R^{18}$ = $SO_2$Me, V = $CH_2$, X = O) |
| 12(a) | cy | Q-6 ($R^{18}$ = $SO_2$Me, V = O, X = O) |
| 12(a) | cz | Q-6 ($R^{18}$ = $SO_2$Me, V = NMe, X = O) |
| 12(a) | da | Q-6 ($R^{18}$ = $SO_2$Me, V = S, X = O) |
| 12(a) | db | Q-6 ($R^{18}$ = Me, V = $CH_2$, X = O) |
| 12(a) | dc | Q-6 ($R^{18}$ = Me, V = O, X = O) |
| 12(a) | dd | Q-6 ($R^{18}$ = Me, V = NMe, X = O) |
| 12(a) | de | Q-6 ($R^{18}$ = Me, V = S, X = O) |
| 12(a) | df | Q-7 (A = $CH_2$, $R^4$ = H, $R^{18}$ = H, X = O) |
| 12(a) | dg | Q-7 (A = O, $R^4$ = H, $R^{18}$ = H, X = O) |
| 12(a) | dh | Q-7 (A = $CHCH_3$, $R^4$ = H, $R^{18}$ = H, X = O) |
| 12(a) | di | Q-7 (A = $CH_2CH_2$, $R^4$ = H, $R^{18}$ = H, X = O) |
| 12(a) | dj | Q-7 (A = $OCH_2$, $R^4$ = H, $R^{18}$ = H, X = O) |
| 12(a) | dk | Q-7 (A = CH(Me)$CH_2$, $R^4$ = H, $R^{18}$ = H, X = O) |
| 12(a) | dl | Q-7 (A = $CH_2$CH(Me), $R^4$ = H, $R^{18}$ = H, X = O) |
| 12(a) | dm | Q-7 (A = S, $R^4$ = H, $R^{18}$ = H, X = O) |
| 12(a) | dn | Q-7 (A = $SCH_2$, $R^4$ = H, $R^{18}$ = H, X = O) |
| 12(a) | do | Q-7 (A = NH, $R^4$ = H, $R^{18}$ = H, X = O) |
| 12(a) | dp | Q-7 (A = NMe, $R^4$ = H, $R^{18}$ = H, X = O) |
| 12(a) | dq | Q-7 (A = $NHCH_2$, $R^4$ = H, $R^{18}$ = H, X = O) |
| 12(a) | dr | Q-7 (A = N(Me)$CH_2$, $R^4$ = H, $R^{18}$ = H, X = O) |
| 12(a) | ds | Q-7 (A = $NCH_2$Ph, $R^4$ = H, $R^{18}$ = H, X = O) |
| 12(a) | dt | Q-7 (A = N($CH_2$Ph)$CH_2$, $R^4$ = H, $R^{18}$ = H, X = O) |
| 12(a) | du | Q-7 (A = $CH_2$, $R^4$ = Me, $R^{18}$ = H, X = O) |
| 12(a) | dv | Q-7 (A = O, $R^4$ = Me, $R^{18}$ = H, X = O) |
| 12(a) | dw | Q-7 (A = $CH_2$, $R^4$ = Me, $R^{18}$ = Me, X = O) |
| 12(a) | dx | Q-7 (A = O, $R^4$ = Me, $R^{18}$ = Me, X = O) |
| 12(a) | dy | Q-7 (A = $CH_2$, $R^4$ = Me, $R^{18}$ = COMe, X = O) |
| 12(a) | dz | Q-7 (A = O, $R^4$ = Me, $R^{18}$ = COMe, X = O) |
| 12(a) | ea | Q-7 (A = $CH_2$, $R^4$ = Me, $R^{18}$ = $CO_2$Me, X = O) |
| 12(a) | eb | Q-7 (A = O, $R^4$ = Me, $R^{18}$ = $CO_2$Me, X = O) |
| 12(a) | ec | Q-7 (A = $CH_2$, $R^4$ = Me, $R^{18}$ = $SO_2$Me, X = O) |
| 12(a) | ed | Q-7 (A = O, $R^4$ = Me, $R^{18}$ = $SO_2$Me, X = O) |
| 12(a) | ee | Q-8 ($R^4$ = H, $R^{18}$ = H, X = O) |
| 12(a) | ef | Q-8 ($R^4$ = H, $R^{18}$ = H, X = S) |
| 12(a) | eg | Q-8 ($R^4$ = Me, $R^{18}$ = H, X = O) |
| 12(a) | eh | Q-8 ($R^4$ = Et, $R^{18}$ = H, X = O) |
| 12(a) | ei | Q-8 ($R^4$ = H, $R^{18}$ = Me, X = O) |
| 12(a) | ej | Q-8 ($R^4$ = H, $R^{18}$ = COMe, X = O) |
| 12(a) | ek | Q-8 ($R^4$ = H, $R^{18}$ = $CO_2$Me, X = O) |
| 12(a) | el | Q-8 ($R^4$ = H, $R^{18}$ = $SO_2$Me, X = O) |
| 12(a) | em | Q-8 ($R^4$ = Me, $R^{18}$ = Me, X = O) |
| 12(a) | en | Q-8 ($R^4$ = Me, $R^{18}$ = COMe, X = O) |
| 12(a) | eo | Q-8 ($R^4$ = Me, $R^{18}$ = $CO_2$Me, X = O) |
| 12(a) | ep | Q-8 ($R^4$ = Me, $R^{18}$ = $SO_2$Me, X = O) |
| 12(a) | eq | Q-8 ($R^4$ = Et, $R^{18}$ = Me, X = O) |
| 12(a) | er | Q-8 ($R^4$ = Et, $R^{18}$ = COMe, X = O) |
| 12(a) | es | Q-8 ($R^4$ = Et, $R^{18}$ = $CO_2$Me, X = O) |
| 12(a) | et | Q-8 ($R^4$ = Et, $R^{18}$ = $SO_2$Me, X = O) |
| 12(a) | eu | Q-9 ($R^4$ = H, $R^{18}$ = H, X = O) |
| 12(a) | ev | Q-9 ($R^4$ = H, $R^{18}$ = H, X = S) |
| 12(a) | ew | Q-9 ($R^4$ = Me, $R^{18}$ = H, X = O) |
| 12(a) | ex | Q-9 ($R^4$ = Et, $R^{18}$ = H, X = O) |
| 12(a) | ey | Q-9 ($R^4$ = H, $R^{18}$ = Me, X = O) |
| 12(a) | ez | Q-9 ($R^4$ = H, $R^{18}$ = COMe, X = O) |
| 12(a) | fb | Q-9 ($R^4$ = H, $R^{18}$ = $SO_2$Me, X = O) |
| 12(a) | fc | Q-9 ($R^4$ = Me, $R^{18}$ = Me, X = O) |
| 12(a) | fd | Q-9 ($R^4$ = Me, $R^{18}$ = COMe, X = O) |
| 12(a) | fe | Q-9 ($R^4$ = Me, $R^{18}$ = $CO_2$Me, X = O) |
| 12(a) | ff | Q-9 ($R^4$ = Me, $R^{18}$ = $SO_2$Me, X = O) |
| 12(a) | fg | Q-9 ($R^4$ = Et, $R^{18}$ = $SO_2$Me, X = O) |
| 12(a) | fh | Q-9 ($R^4$ = Et, $R^{18}$ = Me, X = O) |
| 12(a) | fi | Q-9 ($R^4$ = Et, $R^{18}$ = COMe, X = O) |
| 12(a) | fj | Q-9 ($R^4$ = Et, $R^{18}$ = $CO_2$Me, X = O) |

KEY FOR TABLE 13

$$Q-\overset{\overset{X^1}{|}}{C}=N-G$$

II

| Table | Group | Q |
|---|---|---|
| 13(b) | a | Q-1 (A = $CH_2$) |
| 13(b) | b | Q-1 (A = $CH_2CH_2$) |
| 13(b) | c | Q-1 (A = CHMe) |
| 13(b) | d | Q-1 (A = CH(Me)$CH_2$) |
| 13(b) | e | Q-1 (A = $CH_2$CHCl) |
| 13(b) | f | Q-1 (A = $CH_2$CHMe) |
| 13(b) | g | Q-1 (A = O) |
| 13(b) | h | Q-1 (A = $OCH_2$) |
| 13(b) | i | Q-1 (A = S) |
| 13(b) | j | Q-1 (A = $SCH_2$) |
| 13(b) | k | Q-1 (A = NH) |
| 13(b) | l | Q-1 (A = NMe) |
| 13(b) | m | Q-1 (A = N(Me)$CH_2$) |
| 13(b) | n | Q-1 (A = $NHCH_2$) |
| 13(b) | o | Q-1 (A = $NCH_2$Ph) |
| 13(b) | p | Q-1 (A = N($CH_2$Ph)$CH_2$) |
| 13(b) | q | Q-2 (A = $CH_2$) |
| 13(b) | r | Q-2 (A = $CH_2CH_2$) |
| 13(b) | s | Q-2 (A = CHMe) |
| 13(b) | t | Q-2 (A = CH(Me)$CH_2$) |
| 13(b) | u | Q-2 (A = $CH_2$CHCl) |
| 13(b) | v | Q-2 (A = $CH_2$CHMe) |
| 13(b) | w | Q-2 (A = O) |
| 13(b) | x | Q-2 (A = $OCH_2$) |
| 13(b) | y | Q-2 (A = S) |
| 13(b) | z | Q-2 (A = $SCH_2$) |
| 13(b) | aa | Q-2 (A = NH) |
| 13(b) | ab | Q-2 (A = NMe) |
| 13(b) | ac | Q-2 (A = N(Me)$CH_2$) |
| 13(b) | ad | Q-2 (A = $NHCH_2$) |
| 13(b) | ae | Q-2 (A = NCHPh) |
| 13(b) | af | Q-2 (A = N($CH_2$Ph)$CH_2$) |
| 13(b) | ag | Q-3 (A = CH(Me)$CH_2$, $R^4$ = H, $Y^1$ = H) |
| 13(b) | ah | Q-3 (A = $CH_2CH_2$, $R^4$ = H, $Y^1$ = H) |
| 13(b) | ai | Q-3 (A = CHMe, $R^4$ = H, $Y^1$ = H) |
| 13(b) | aj | Q-3 (A = $CH_2$CHMe, $R^4$ = H, $Y^1$ = H) |
| 13(b) | ak | Q-3 (A = CH(Me)$CH_2$, $R^4$ = H, $Y^1$ = H) |
| 13(b) | al | Q-3 (A = O, $R^4$ = H, $Y^1$ = H) |
| 13(b) | am | Q-3 (A = $OCH_2$, $R^4$ = H, $Y^1$ = H) |
| 13(b) | an | Q-3 (A = S, $R^4$ = H, $Y^1$ = H) |
| 13(b) | ao | Q-3 (A = $SCH_2$, $R^4$ = H, $Y^1$ = H) |
| 13(b) | ap | Q-3 (A = NH, $R^4$ = H, $Y^1$ = H) |
| 13(b) | aq | Q-3 (A = NMe, $R^4$ = H, $Y^1$ = H) |
| 13(b) | ar | Q-3 (A = $NHCH_2$, $R^4$ = H, $Y^1$ = H) |

KEY FOR TABLE 13

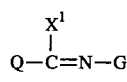

II

| Table | Group | Q |
|---|---|---|
| 13(b) | as | Q-3 (A = N(Me)CH$_2$, R$^4$ = H, Y$^1$ = H) |
| 13(b) | at | Q-3 (A = NCH$_2$Ph, R$^4$ = H, Y$^1$ = H) |
| 13(b) | au | Q-3 (A = N(CH$_2$Ph)CH$_2$, R$^4$ = H, Y$^1$ = H) |
| 13(b) | av | Q-3 (A = CH$_2$, R$^4$ = Me, Y$^1$ = H) |
| 13(b) | aw | Q-3 (A = O, R$^4$ = Me, Y$^1$ = H) |
| 13(b) | ax | Q-3 (A = CH$_2$, R$^4$ = H, Y$^1$ = Me) |
| 13(b) | ay | Q-3 (A = O, R$^4$ = H, Y$^1$ = Me) |
| 13(b) | az | Q-3 (A = CH$_2$, R$^4$ = Me, Y$^1$ = Me) |
| 13(b) | ba | Q-3 (A = O, R$^4$ = Me, Y$^1$ = Me) |
| 13(b) | bb | Q-4 (R$^4$ = H) |
| 13(b) | bc | Q-4 (R$^4$ = Me) |
| 13(b) | bd | Q-4 (R$^4$ = Et) |
| 13(b) | be | Q-5 (R$^{18}$ = H, V = CH$_2$) |
| 13(b) | bf | Q-5 (R$^{18}$ = H, V = O) |
| 13(b) | bg | Q-5 (R$^{18}$ = H, V = NH) |
| 13(b) | bh | Q-5 (R$^{18}$ = H, V = NMe) |
| 13(b) | bi | Q-5 (R$^{18}$ = H, V = NCH$_2$Ph) |
| 13(b) | bj | Q-5 (R$^{18}$ = H, V = S) |
| 13(b) | bk | Q-5 (R$^{18}$ = H, V = CHCH$_3$) |
| 13(b) | bl | Q-5 (R$^{18}$ = COMe, V = CH$_2$) |
| 13(b) | bm | Q-5 (R$^{18}$ = COMe, V = O) |
| 13(b) | bn | Q-5 (R$^{18}$ = COMe, V = NMe) |
| 13(b) | bo | Q-5 (R$^{18}$ = CO$_2$Me, V = CH$_2$) |
| 13(b) | bp | Q-5 (R$^{18}$ = CO$_2$Me, V = O) |
| 13(b) | bq | Q-5 (R$^{18}$ = CO$_2$Me, V = NMe) |
| 13(b) | br | Q-5 (R$^{18}$ = SO$_2$Me, V = CH$_2$) |
| 13(b) | bs | Q-5 (R$^{18}$ = SO$_2$Me, V = O) |
| 13(b) | bt | Q-5 (R$^{18}$ = SO$_2$Me, V = NMe) |
| 13(b) | bu | Q-5 (R$^{18}$ = Me, V = CH$_2$) |
| 13(b) | bv | Q-5 (R$^{18}$ = Me, V = O) |
| 13(b) | bw | Q-5 (R$^{18}$ = Me, V = NMe) |
| 13(b) | bx | Q-6 (R$^{18}$ = H, V = CH$_2$) |
| 13(b) | by | Q-6 (R$^{18}$ = H, V = O) |
| 13(b) | bz | Q-6 (R$^{18}$ = H, V = NH) |
| 13(b) | ca | Q-6 (R$^{18}$ = H, V = NMe) |
| 13(b) | cb | Q-6 (R$^{18}$ = H, V = NCH$_2$Ph) |
| 13(b) | cc | Q-6 (R$^{18}$ = H, V = S) |
| 13(b) | cd | Q-6 (R$^{18}$ = H, V = CHCH$_3$) |
| 13(b) | ce | Q-6 (R$^{18}$ = COMe, V = CH$_2$) |
| 13(b) | cf | Q-6 (R$^{18}$ = COMe, V = O) |
| 13(b) | cg | Q-6 (R$^{18}$ = COMe, V = NMe) |
| 13(b) | ch | Q-6 (R$^{18}$ = CO$_2$Me, V = CH$_2$) |
| 13(b) | ci | Q-6 (R$^{18}$ = CO$_2$Me, V = O) |
| 13(b) | cj | Q-6 (R$^{18}$ = CO$_2$Me, V = NMe) |
| 13(b) | ck | Q-6 (R$^{18}$ = CO$_2$Me, V = S) |
| 13(b) | cl | Q-6 (R$^{18}$ = COMe, V = S) |
| 13(b) | cm | Q-6 (R$^{18}$ = SO$_2$Me, V = CH$_2$) |
| 13(b) | cn | Q-6 (R$^{18}$ = SO$_2$Me, V = O) |
| 13(b) | co | Q-6 (R$^{18}$ = SO$_2$Me, V = S) |
| 13(b) | cp | Q-6 (R$^{18}$ = SO$_2$Me, V = NMe) |
| 13(b) | cq | Q-6 (R$^{18}$ = Me, V = CH$_2$) |
| 13(b) | cr | Q-6 (R$^{18}$ = Me, V = O) |
| 13(b) | cs | Q-6 (R$^{18}$ = Me, V = S) |
| 13(b) | ct | Q-6 (R$^{18}$ = Me, V = NMe) |
| 13(b) | cu | Q-5 (R$^{18}$ = COMe, V = S) |
| 13(b) | cv | Q-5 (R$^{18}$ = CO$_2$Me, V = S) |
| 13(b) | cw | Q-5 (R$^{18}$ = SO$_2$Me, V = S) |
| 13(b) | cx | Q-5 (R$^{18}$ = Me, V = S) |
| 13(b) | cy | Q-7 (A = CH$_2$, R$^4$ = H, R$^{18}$ = H) |
| 13(b) | cz | Q-7 (A = O, R$^4$ = H, R$^{18}$ = H) |
| 13(b) | da | Q-7 (A = CH$_2$CH$_2$, R$^4$ = H, R$^{18}$ = H) |
| 13(b) | db | Q-7 (A = CHMe, R$^4$ = H, R$^{18}$ = H) |
| 13(b) | dc | Q-7 (A = O, R$^4$ = Et, R$^{18}$ = H) |
| 13(b) | dd | Q-7 (A = CH$_2$, R$^4$ = Et, R$^{18}$ = H) |
| 13(b) | de | Q-7 (A = OCH$_2$, R$^4$ = H, R$^{18}$ = H) |
| 13(b) | df | Q-7 (A = CH(Me)CH$_2$, R$^4$ = H, R$^{18}$ = H) |
| 13(b) | dg | Q-7 (A = CH$_2$CH(Me), R$^4$ = H, R$^{18}$ = H) |

KEY FOR TABLE 13

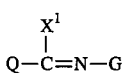

II

| Table | Group | Q |
|---|---|---|
| 13(b) | dh | Q-7 (A = S, R$^4$ = H, R$^{18}$ = H) |
| 13(b) | di | Q-7 (A = SCH$_2$, R$^4$ = H, R$^{18}$ = H) |
| 13(b) | dj | Q-7 (A = NH, R$^4$ = H, R$^{18}$ = H) |
| 13(b) | dk | Q-7 (A = NMe, R$^4$ = H, R$^{18}$ = H) |
| 13(b) | dl | Q-7 (A = NHCH$_2$, R$^4$ = H, R$^{18}$ = H) |
| 13(b) | dm | Q-7 (A = N(Me)CH$_2$, R$^4$ = H, R$^{18}$ = H) |
| 13(b) | dn | Q-7 (A = NCH$_2$Ph, R$^4$ = H, R$^{18}$ = H) |
| 13(b) | do | Q-7 (A = N(CH$_2$Ph)CH$_2$, R$^4$ = H, R$^{18}$ = H) |
| 13(b) | dp | Q-7 (A = CH$_2$, R$^4$ = Me, R$^{18}$ = H) |
| 13(b) | dq | Q-7 (A = O, R$^4$ = Me, R$^{18}$ = H) |
| 13(b) | dr | Q-7 (A = CH$_2$, R$^4$ = Me, R$^{18}$ = Me) |
| 13(b) | ds | Q-7 (A = O, R$^4$ = Me, R$^{18}$ = Me) |
| 13(b) | dt | Q-7 (A = CH$_2$, R$^4$ = Me, R$^{18}$ = COMe) |
| 13(b) | du | Q-7 (A = O, R$^4$ = Me, R$^{18}$ = COMe) |
| 13(b) | dv | Q-7 (A = CH$_2$, R$^4$ = Me, R$^{18}$ = CO$_2$Me) |
| 13(b) | dw | Q-7 (A = O, R$^4$ = ,Me, R$^{18}$ = CO$_2$Me) |
| 13(b) | dx | Q-7 (A = CH$_2$, R$^4$ = Me, R$^{18}$ = SO$_2$Me) |
| 13(b) | dy | Q-7 (A = O, R$^4$ = Me, R$^{18}$ = SO$_2$Me) |
| 13(b) | dz | Q-8 (R$^4$ = H, R$^{18}$ = H) |
| 13(b) | ea | Q-8 (R$^4$ = Me, R$^{18}$ = H) |
| 13(b) | eb | Q-8 (R$^4$ = Et, R$^{18}$ = H) |
| 13(b) | ec | Q-8 (R$^4$ = H, R$^{18}$ = Me) |
| 13(b) | ed | Q-8 (R$^4$ = H, R$^{18}$ = COMe) |
| 13(b) | ee | Q-8 (R$^4$ = H, R$^{18}$ = CO$_2$Me) |
| 13(b) | ef | Q-8 (R$^4$ = H, R$^{18}$ = SO$_2$Me) |
| 13(b) | eg | Q-8 (R$^4$ = Me, R$^{18}$ = Me) |
| 13(b) | eh | Q-8 (R$^4$ = Me, R$^{18}$ = COMe) |
| 13(b) | ei | Q-8 (R$^4$ = Me, R$^{18}$ = CO$_2$Me) |
| 13(b) | ej | Q-8 (R$^4$ = Me, R$^{18}$ = SO$_2$Me) |
| 13(b) | ek | Q-8 (R$^4$ = Et, R$^{18}$ = Me) |
| 13(b) | el | Q-8 (R$^4$ = Et, R$^{18}$ = COMe) |
| 13(b) | em | Q-8 (R$^4$ = Et, R$^{18}$ = CO$_2$Me) |
| 13(b) | en | Q-8 (R$^4$ = Et, R$^{18}$ = SO$_2$Me) |
| 13(b) | eo | Q-9 (R$^4$ = H, R$^{18}$ = H) |
| 13(b) | ep | Q-9 (R$^4$ = Me, R$^{18}$ = H) |
| 13(b) | eq | Q-9 (R$^4$ = Et, R$^{18}$ = H) |
| 13(b) | er | Q-9 (R$^4$ = H, R$^{18}$ = Me) |
| 13(b) | es | Q-9 (R$^4$ = H, R$^{18}$ = COMe) |
| 13(b) | et | Q-9 (R$^4$ = H, R$^{18}$ = CO$_2$Me) |
| 13(b) | eu | Q-9 (R$^4$ = H, R$^{18}$ = SO$_2$Me) |
| 13(b) | ev | Q-9 (R$^4$ = Me, R$^{18}$ = Me) |
| 13(b) | ew | Q-9 (R$^4$ = Me, R$^{18}$ = COMe) |
| 13(b) | ex | Q-9 (R$^4$ = Me, R$^{18}$ = CO$_2$Me) |
| 13(b) | ey | Q-9 (R$^4$ = Me, R$^{18}$ = SO$_2$Me) |
| 13(b) | ez | Q-9 (R$^4$ = Et, R$^{18}$ = Me) |
| 13(b) | fa | Q-9 (R$^4$ = Et, R$^{18}$ = COMe) |
| 13(b) | fb | Q-9 (R$^4$ = Et, R$^{18}$ = CO$_2$Me) |
| 13(b) | fc | Q-9 (R$^4$ = Et, R$^{18}$ = SO$_2$Me) |

(a) Compounds of Table 12 wherein G, R$^1$, R$_a^2$, R$_b^2$, R$^3$ and Y are as set out therein can be prepared according to the teachings of this invention having the recited values of Groups a through fj in the Key for Table 12. Each of these compounds is specifically included within the scope of this invention.

(b) Compounds of Table 13 wherein G, R$^1$, R$_a^2$, R$_b^2$, R$^3$ and X$^1$ are as set out therein can be prepared according to the teachings of this invention having the recited values of Groups a through fc in the Key for Table 13. Each of these compounds is specifically included within the scope of this invention.

Compounds of Tables 12 and 13 wherein Q is as set out therein contain the following substitution patterns for R$_a^2$, R$_b^2$:

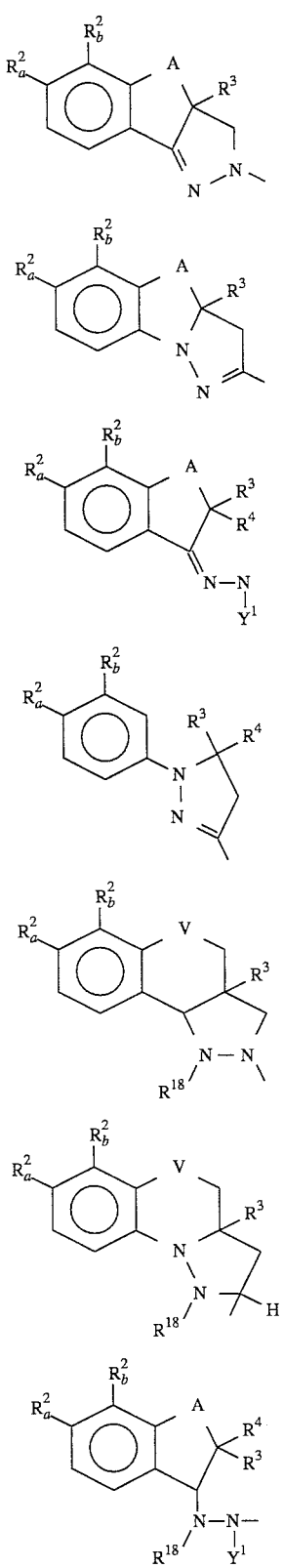

Each compound for which $R_a^2$, $R_b^2$, $R^3$, $R^4$, $R^{18}$, A, $Y^1$ and V are recited is a compound of this invention which can be made according to the preparatory procedures disclosed herein. Each of such compounds is, therefore, a specific embodiment of this invention.

TABLE 12

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| $R_a^2 = R_b^2 = R^3 = Y = H$ | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = R_b^2 = Y = H, R^3 = Me$ | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = Y = H, R^3 = Et$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = Y = H, R^3 = i\text{-}Pr$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = Y = H, R^3 = CO_2Me$

| G | $R^1$ | G | $R^1$ |
|---|---|---|---|
| G-1 | Cl | G-5 | CN |
| G-1 | Br | $CH_2Ph$ | Cl |

$R_a^2 = R_b^2 = Y = H, R^3 = Ph$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = Y = H, R^3 = 4\text{-}F\text{-}Ph$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = Y = H, R^3 = 4\text{-Cl-Ph}$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = Cl, R^3 = H$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = Cl, R^3 = Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = Cl, R^3 = Et$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = Cl, R^3 = i\text{-Pr}$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = Cl, R^3 = CO_2Me$

| G | $R^1$ | G | $R^1$ |
|---|---|---|---|
| G-1 | Cl | G-5 | CN |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = Cl, R^3 = Ph$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = Cl, R^3 = 4\text{-F-Ph}$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = Cl, R^3 = 4\text{-Cl-Ph}$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = Cl, R^3 = H$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = CF_3, R^3 = Me$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = CF_3, R^3 = Et$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = CF_3, R^3 = i\text{-Pr}$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = CF_3, R^3 = CO_2Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = CF_3, R^3 = Ph$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = CF_3, R^3 = 4\text{-F-Ph}$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = CF_3, R^3 = 4\text{-Cl-Ph}$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = Br, R^3 = H$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = Br, R^3 = Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = Br, R^3 = Et$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_b^2 = Y = H, R_a^2 = Br, R^3 = i\text{-Pr}$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-5 | $OCF_3$ | | |
| $R_b^2 = Y = H, R_a^2 = Br, R^3 = CO_2Me$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_b^2 = Y = H, R_a^2 = Br, R^3 = 4\text{-F-Ph}$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_b^2 = Y = H, R_a^2 = Br, R^3 = H$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_b^2 = Y = H, R_a^2 = Br, R^3 = 4\text{-Cl-Ph}$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_b^2 = Y = H, R_a^2 = OCHF_2, R^3 = H$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_b^2 = Y = H, R_a^2 = OCHF_2, R^3 = CO_2Me$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = OCHF_2, R^3 = Ph$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = OCHF_2, R^3 = 4\text{-Cl-Ph}$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-5 | CF$_3$ | | |
| G-5 | OCF$_3$ | | |

$R_b^2 = Y = H, R_a^2 = OCHF_2, R^3 = 4\text{-F-Ph}$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = OCH_2CF_3, R^3 = H$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = OCH_2CF_3, R^3 = Me$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = OCH_2CF_3, R^3 = Et$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = OCH_2CF_3, R^3 = i\text{-Pr}$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = OCH_2CF_3, R^3 = CO_2Me$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = OCH_2CF_3, R^3 = Ph$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_b^2 = Y = H, R_a^2 = OCH_2CF_3, R^3 = 4\text{-Cl-Ph}$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a{}^2 = R_b{}^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-5 | Br | | |
| G-5 | $CF_3$ | | |
| G-5 | $OCF_3$ | | |

$R_b{}^2 = Y = H, R_a{}^2 = OCH_2CF_3, R^3 = 4\text{-F-Ph}$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a{}^2 = Y = H, R_b{}^2 = F, R^3 = H$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a{}^2 = Y = H, R_b{}^2 = F, R^3 = Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a{}^2 = Y = H, R_b{}^2 = F, R^3 = Et$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a{}^2 = Y = H, R_b{}^2 = F, R^3 = i\text{-Pr}$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a{}^2 = Y = H, R_b{}^2 = F, R^3 = CO_2Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = Y = H, R_b^2 = F, R^3 = Ph$ | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = Y = H, R_b^2 = F, R^3 = 4\text{-Cl-Ph}$ | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| $R_a^2 = Y = H, R_b^2 = F, R^3 = 4\text{-F-Ph}$ | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = R_b^2 = H, Y = \text{COMe}, R^3 = \text{Me}$ | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = R_b^2 = H, Y = \text{COMe}, R^3 = \text{i-Pr}$ | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = H, Y = COMe, R^3 = CO_2Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = H, Y = COMe, R^3 = 4$-F-Ph

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = H, Y = CO_2Me, R^3 = Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = H, Y = CO_2Me, R^3 = i$-Pr

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = H, Y = CO_2Me, R^3 = CO_2Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = R_b^2 = H, Y = CO_2Me, R^3 = 4\text{-}F\text{-}Ph$

| G | $R^1$ | G | $R^1$ |
|---|---|---|---|
| G-1 | Cl | G-5 | CN |
| G-1 | Br | $CH_2Ph$ | cl. |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | 0-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = Cl, R_b^2 = H, Y = COMe, R^3 = Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G.3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = Cl, R_b^2 = H, Y = COMe, R^3 = i\text{-}Pr$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = Cl, R_b^2 = H, Y = COMe, R^3 = CO_2Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Ci |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = Cl, R_b^2 = H, Y = COMe, R^3 = 4\text{-}F\text{-}Ph$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = Cl, R_b^2 = H, Y = CO_2Me, R^3 = Me$

| G | $R^1$ | G | $R^1$ |
|---|---|---|---|
| G-1 | Cl | G-5 | CN |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2 = Cl, R_b^2 = H, Y = CO_2Me, R^3 = i\text{-Pr}$

| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2 = Cl, R_b^2 = H, Y = CO_2Me, R^3 = CO_2Me$

| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2 = Cl, R_b^2 = H, Y = CO_2Me, R^3 = 4\text{-F-Ph}$

| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2 = CF_3, R_b^2 = H, Y = COMe, R^3 = Me$

| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2 = CF_3, R_b^2 = H, Y = COMe, R^3 = i\text{-Pr}$

| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_a^2 = CF_3, R_b^2 = H, Y = COMe, R^3 = CO_2Me$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_a^2 = CF_3, R_b^2 = H, Y = CO_2Me, R^3 = 4\text{-F-Ph}$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_a^2 = CF_3, R_b^2 = H, Y = CO_2Me, R^3 = Me$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_a^2 = CF_3, R_b^2 = H, Y = CO_2Me, R^3 = i\text{-Pr}$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_a^2 = CF_3, R_b^2 = H, Y = CO_2Me, R^3 = CO_2Me$ | | | |
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = CF_3, R_b^2 = H, Y = CO_2Me, R^3 = 4$-F-Ph

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = Cl, R_b^2 = Cl, Y = H, R^3 = CO_2Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = Cl, R_b^2 = Cl, Y = H, R^3 = i$-Pr

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = Cl, R_b^2 = F, Y = H, R^3 = CO_2Me$

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2 = Cl, R_b^2 = F, Y = H, R^3 = i$-Pr

| G | $R^1$ | G | $R^1$ |
|---|---|---|---|
| G-1 | Cl | G-5 | CN |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-5 | OCF$_3$ | | |
| $R_a^2 = R_b^2 = H$, Y = Me, $R^3$ = Me | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = R_b^2 = H$, Y = Me, $R^3$ = i-Pr | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = R_b^2 = H$, Y = Me, $R^3$ = CO$_2$Me | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = R_b^2 = H$, Y = Me, $R^3$ = 4-F-Ph | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = Cl$, $R_b^2 = H$, Y = Me, $R^3$ = Me | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = Cl$, $R_b^2 = H$, Y = Me, $R^3$ = i-Pr | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2 = Cl, R_b^2 = H, Y = Me, R^3 = CO_2Me$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2 = Cl, R_b^2 = H, Y = Me, R^3 = 4\text{-}F\text{-}Ph$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2 = CF_3, R_b^2 = H, Y = Me, R^3 = Me$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2 = CF_3, R_b^2 = H, Y = Me, R^3 = i\text{-}Pr$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2 = CF_3, R_b^2 = H, Y = Me, R^3 = CO_2Me$

| G | $R^1$ | G | $R^1$ |
|---|---|---|---|
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |

TABLE 12-continued

This Table contains a large number of compounds of Formula I. A format has been adopted for their recitation that avoids the mechanical reproduction of substituent values that do not vary. For example, the first table entry (where G is G-1, $R^1$ is Cl and $R_a^2 = R_b^b = R^3 = Y = H$) actually specifies 166 separate and distinct compounds because the Key for Table 12 identifies additional substituent values a through fj for each Table 12 entry.

| G | $R^1$ | G | $R^1$ |
|---|---|---|---|
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = CF_3, R_b^2 = H, Y = Me, R^3 = 4\text{-F-Ph}$ | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = R_b^2 = H, Y = Me, R^3 = 4\text{-Cl-Ph}$ | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |
| $R_a^2 = Cl, R_b^2 = H, Y = Me, R^3 = 4\text{-Cl-Ph}$ | | | |
| G-1 | Cl | G-5 | CN |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

TABLE 13

This Table contains a large number of compounds of Formula II. The first entry (where G is G-1, $R^1$ is Cl, $R_a^2 = Cl, R_b^2 = H$, $X^1 = Cl$ and $R^3 = i\text{-Pr}$) actually specifies 159 separate and distinct compounds because the Key for Table 13 identifies additional substituent values a through fc for each Table 13 entry.

| G | $R^1$ | G | $R^1$ |
|---|---|---|---|
| $R_a^2 = Cl, R_b^2 = H, X^1 = Cl, R^3 = i\text{-Pr}$ | | | |
| G-1 | Cl | G-5 | OCF$_3$ |
| G-1 | Br | G-5 | CN |
| G-1 | CF$_3$ | CH$_2$Ph | Cl |
| G-1 | OCF$_3$ | CH$_2$Ph | Br |
| G-1 | CN | CH$_2$Ph | CF$_3$ |

TABLE 13-continued

This Table contains a large number of compounds of Formula II. The first entry (where G is G-1, $R^1$ is Cl, $R_a^2$ = Cl, $R_b^2$ = H, $X^1$ = Cl and $R^3$ = i-Pr) actually specifies 159 separate and distinct compounds because the Key for Table 13 identifies additional substituent values a through fc for each Table 13 entry.

| G | $R^1$ | G | $R^1$ |
|---|---|---|---|
| G-2 | Cl | CH$_2$Ph | OCF$_3$ |
| G-2 | Br | CH$_2$Ph | CN |
| G-2 | CF$_3$ | G-7 | Cl |
| G-2 | OCF$_3$ | G-7 | Br |
| G-2 | CN | G-7 | CF$_3$ |
| G-3 | Cl | G-7 | OCF$_3$ |
| G-3 | Br | G-7 | CN |
| G-3 | CF$_3$ | G-8 | Cl |
| G-3 | OCF$_3$ | G-8 | Br |
| G-3 | CN | G-8 | CF$_3$ |
| G-4 | Cl | G-8 | OCF$_3$ |
| G-4 | Br | G-8 | CN |
| G-4 | CF$_3$ | G-10 | Cl |
| G-4 | OCF$_3$ | G-10 | Br |
| G-4 | CN | G-10 | CF$_3$ |
| G-5 | Cl | G-10 | OCF$_3$ |
| G-5 | Br | G-10 | CN |
| G-5 | CF$_3$ | | |

$R_a^2$ = Cl, $R_b^2$ = H, $X^1$ = Cl, $R^3$ = CO$_2$Me

| G | $R^1$ | G | $R^1$ |
|---|---|---|---|
| G-1 | Cl | G-5 | OCF$_3$ |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2$ = Cl, $R_b^2$ = H, $X^1$ = Cl, $R^3$ = 4-Cl-Ph

| G | $R^1$ | G | $R^1$ |
|---|---|---|---|
| G-1 | Cl | G-5 | OCF$_3$ |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2$ = Cl, $R_b^2$ = H, $X^1$ = Cl, $R^3$ = 4-F-Ph

| G | $R^1$ | G | $R^1$ |
|---|---|---|---|
| G-1 | Cl | G-5 | OCF$_3$ |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2$ = Cl, $R_b^2$ = H, $X^1$ = OAc, $R^3$ = i-Pr

| G | $R^1$ | G | $R^1$ |
|---|---|---|---|
| G-1 | Cl | G-5 | OCF$_3$ |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |
| G-4 | Br | G-10 | Cl |
| G-4 | CF$_3$ | G-10 | Br |
| G-4 | OCF$_3$ | G-10 | CF$_3$ |
| G-4 | CN | G-10 | OCF$_3$ |
| G-5 | Cl | G-10 | CN |
| G-5 | Br | | |
| G-5 | CF$_3$ | | |
| G-5 | OCF$_3$ | | |

$R_a^2$ = Cl, $R_b^2$ = H, $X^1$ = OAc, $R^3$ = CO$_2$Me

| G | $R^1$ | G | $R^1$ |
|---|---|---|---|
| G-1 | Cl | G-5 | OCF$_3$ |
| G-1 | Br | CH$_2$Ph | Cl |
| G-1 | CF$_3$ | CH$_2$Ph | Br |
| G-1 | OCF$_3$ | CH$_2$Ph | CF$_3$ |
| G-1 | CN | CH$_2$Ph | OCF$_3$ |
| G-2 | Cl | CH$_2$Ph | CN |
| G-2 | Br | G-7 | Cl |
| G-2 | CF$_3$ | G-7 | Br |
| G-2 | OCF$_3$ | G-7 | CF$_3$ |
| G-2 | CN | G-7 | OCF$_3$ |
| G-3 | Cl | G-7 | CN |
| G-3 | Br | G-8 | Cl |
| G-3 | CF$_3$ | G-8 | Br |
| G-3 | OCF$_3$ | G-8 | CF$_3$ |
| G-3 | CN | G-8 | OCF$_3$ |
| G-4 | Cl | G-8 | CN |

TABLE 13-continued

This Table contains a large number of compounds of Formula II. The first entry (where G is G-1, $R^1$ is Cl, $R_a^2$ = Cl, $R_b^2$ = H, $X^1$ = Cl and $R^3$ = i-Pr) actually specifies 159 separate and distinct compounds because the Key for Table 13 identifies additional substituent values a through fc for each Table 13 entry.

| G | $R^1$ | G | $R^1$ |
|---|---|---|---|
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = Cl, $R_b^2$ = H, $X^1$ = OAc, $R^3$ = 4-Cl-Ph

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = Cl, $R_b^2$ = H, $X^1$ = OAc, $R^3$ = 4-F-Ph

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = $CF_3$, $R_b^2$ = H, $X^1$ = Cl, $R^3$ = i-Pr

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = $CF_3$, $R_b^2$ = H, $X^1$ = Cl, $R^3$ = $CO_2Me$

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = $CF_3$, $R_b^2$ = H, $X^1$ = Cl, $R^3$ = 4-Cl-Ph

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

TABLE 13-continued

This Table contains a large number of compounds of Formula II.
The first entry (where G is G-1, $R^1$ is Cl, $R_a^2$ = Cl, $R_b^2$ = H,
$X^1$ = Cl and $R^3$ = i-Pr) actually specifies
159 separate and distinct compounds because the Key for Table 13
identifies additional substituent values a through fc
for each Table 13 entry.

| G | $R^1$ | G | $R^1$ |
|---|---|---|---|
| $R_a^2 = CF_3$, $R_b^2 = H$, $X^1 = Cl$, $R^3 = $ 4-F-Ph ||||
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_a^2 = CF_3$, $R_b^2 = H$, $X^1 = OAc$, $R^3 = $ 4-F-Ph ||||
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_a^2 = CF_3$, $R_b^2 = H$, $X^1 = OAc$, $R^3 = $ 4-Cl-Ph ||||
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_a^2 = CF_3$, $R_b^2 = H$, $X^1 = OAc$, $R^3 = CO_2Me$ ||||
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_a^2 = CF_3$, $R_b^2 = H$, $X^1 = OAc$, $R^3 = $ i-Pr ||||
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |
| $R_a^2 = H$, $R_b^2 = F$, $X^1 = Cl$, $R^3 = $ i-Pr ||||
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |

TABLE 13-continued

This Table contains a large number of compounds of Formula II. The first entry (where G is G-1, $R^1$ is Cl, $R_a^2$ = Cl, $R_b^2$ = H, $X^1$ = Cl and $R^3$ = i-Pr) actually specifies 159 separate and distinct compounds because the Key for Table 13 identifies additional substituent values a through fc for each Table 13 entry.

| G | $R^1$ | G | $R^1$ |
|---|---|---|---|
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = H, $R_b^2$ = F, $X^1$ = Cl, $R^3$ = $CO_2Me$

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = H, $R_b^2$ = F, $X^1$ = Cl, $R^3$ = 4-Cl-Ph

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = H, $R_b^2$ = F, $X^1$ = Cl, $R^3$ = 4-F-Ph

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = H, $R_b^2$ = F, $X^1$ = OAc, $R^3$ = 4-F-Ph

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |

TABLE 13-continued

This Table contains a large number of compounds of Formula II.
The first entry (where G is G-1, $R^1$ is Cl, $R_a^2$ = Cl, $R_b^2$ = H,
$X^1$ = Cl and $R^3$ = i-Pr) actually specifies
159 separate and distinct compounds because the Key for Table 13
identifies additional substituent values a through fc
for each Table 13 entry.

| G | $R^1$ | G | $R^1$ |
|---|---|---|---|
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = H, $R_b^2$ = F, $X^1$ = OAc, $R^3$ = $CO_2Me$

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

$R_a^2$ = H, $R_b^2$ = F, $X^1$ = OAc, $R^3$ = i-Pr

| G | $R^1$ | G | $R^1$ |
|---|---|---|---|
| G-1 | Cl | G-5 | $OCF_3$ |
| G-1 | Br | $CH_2Ph$ | Cl |
| G-1 | $CF_3$ | $CH_2Ph$ | Br |
| G-1 | $OCF_3$ | $CH_2Ph$ | $CF_3$ |
| G-1 | CN | $CH_2Ph$ | $OCF_3$ |
| G-2 | Cl | $CH_2Ph$ | CN |
| G-2 | Br | G-7 | Cl |
| G-2 | $CF_3$ | G-7 | Br |
| G-2 | $OCF_3$ | G-7 | $CF_3$ |
| G-2 | CN | G-7 | $OCF_3$ |
| G-3 | Cl | G-7 | CN |
| G-3 | Br | G-8 | Cl |
| G-3 | $CF_3$ | G-8 | Br |
| G-3 | $OCF_3$ | G-8 | $CF_3$ |
| G-3 | CN | G-8 | $OCF_3$ |
| G-4 | Cl | G-8 | CN |
| G-4 | Br | G-10 | Cl |
| G-4 | $CF_3$ | G-10 | Br |
| G-4 | $OCF_3$ | G-10 | $CF_3$ |
| G-4 | CN | G-10 | $OCF_3$ |
| G-5 | Cl | G-10 | CN |
| G-5 | Br | | |
| G-5 | $CF_3$ | | |
| G-5 | $OCF_3$ | | |

Key for Table 14

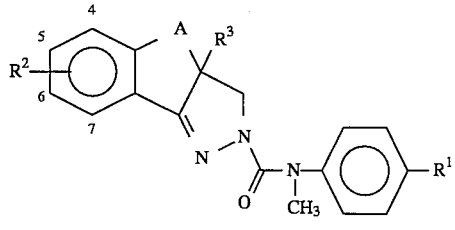

| Group | $R^1$ |
|---|---|
| a | $CF_3$ |
| b | $OCF_3$ |
| c | Cl |
| d | Br |

Compounds of Table 14 wherein A, $R^2$, and $R^3$ are as set out therein can be prepared having the recited values of Groups a through d. That is, for each value of A, $R^2$, and $R^3$ in Table 1, $R^1$ can be $CF_3$, $OCF_3$, Cl or Br. All of said compounds are specifically included within the scope of this invention.

TABLE 14

This Table contains a large number of compounds of Formula I in a format adopted to avoid mechanical reproduction of substituent values that do not vary. For example, the first table entry (where A is $CH_2CH_2$, $R^2$ is 4-F and $R^3$ is CN) actually specifies 4 separate and distinct compounds because the key for Table 14 identifies additional substituent values of $R^1$, namely Group a through d for each Table 14 entry.

| A is $CH_2CH_2$; $R^2$ is 4-F $R^3$ | A is $CH_2CH_2$; $R^2$ is 5-F $R^3$ | A is $CH_2CH_2$; $R^2$ is 5-Cl $R^3$ |
|---|---|---|
| CN | CN | CN |
| $NO_2$ | $NO_2$ | $NO_2$ |
| $N_3$ | $N_3$ | $N_3$ |
| Br | Br | Br |
| $NMe_2$ | $NMe_2$ | $NMe_2$ |
| $NHCO_2Me$ | $NHCO_2Me$ | $NHCO_2Me$ |
| epoxyethyl | epoxyethyl | epoxyethyl |
| epoxyisopropenyl | epoxyisopropenyl | epoxyisopropenyl |
| $SiMe_3$ | $SiMe_3$ | $SiMe_3$ |
| SMe | SMe | SMe |
| S(O)Me | S(O)ME | S(O)ME |
| $SO_2Me$ | $SO_2Me$ | $SO_2Me$ |
| $P(O)(OMe)_2$ | $P(O)(OMe)_2$ | $P(O)(OMe)_2$ |
| $CH_2C(O)NMe_2$ | $CH_2C(O)NMe_2$ | $CH_2C(O)NMe_2$ |
| $CH_2SMe$ | $CH_2SMe$ | $CH_2SMe$ |
| $CH_2OCH_2CF_3$ | $CH_2OCH_2CF_3$ | $CH_2OCH_2CF_3$ |
| $CH_2SiMe_3$ | $CH_2SiMe_3$ | $CH_2SiMe_3$ |
| $CH_2NMe_2$ | $CH_2NMe_2$ | $CH_2NMe_2$ |
| $CH_2$-2-pyridyl | $CH_2$-2-pyridyl | $CH_2$-2-pyridyl |
| 2-pyridyl | 2-pyridyl | 2-pyridyl |
| $C(H)=NOCH_3$ | $C(H)=NOCH_3$ | $C(H)=NOCH_3$ |
| 3-pyridyl | 3-pyridyl | 3-pyridyl |
| 2-thienyl | 2-thienyl | 2-thienyl |
| 3-thienyl | 3-thienyl | 3-thienyl |
| 2-oxazolinyl | 2-oxazolinyl | 2-oxazolinyl |
| 2-(1,3-dioxolanyl) | 2-(1,3-dioxolanyl) | 2-(1,3-dioxolanyl) |
| A is $CH_2CH_2$; $R^2$ is 6-$CF_3$; $R^3$ | A is $OCH_2$; $R^2$ is 4-F; $R^3$ | A is $OCH_2$; $R^2$ is 5-F $R^3$ |
| CN | CN | CN |
| $NO_2$ | $NO_2$ | $NO_2$ |
| $N_3$ | $N_3$ | $N_3$ |
| Br | Br | Br |
| $NMe_2$ | $NMe_2$ | $NMe_2$ |
| $NHCO_2Me$ | $NHCO_2Me$ | $NHCO_2Me$ |
| epoxyethyl | epoxyethyl | epoxyethyl |
| epoxyisopropenyl | epoxyisopropenyl | epoxyisopropenyl |

TABLE 14-continued

This Table contains a large number of compounds of Formula I in a format adopted to avoid mechanical reproduction of substituent values that do not vary. For example, the first table entry (where A is $CH_2CH_2$, $R^2$ is 4-F and $R^3$ is CN) actually specifies 4 separate and distinct compounds because the key for Table 14 identifies additional substituent values of $R^1$, namely Group a through d for each Table 14 entry.

| | | |
|---|---|---|
| $SiMe_3$ | $SiMe_3$ | $SiMe_3$ |
| SMe | SMe | SMe |
| S(O)Me | S(O)Me | S(O)Me |
| $SO_2Me$ | $SO_2Me$ | $SO_2Me$ |
| $P(O)(OMe)_2$ | $P(O)(OMe)_2$ | $P(O)(OMe)_2$ |
| $CH_2C(O)NMe_2$ | $CH_2C(O)NMe_2$ | $CH_2C(O)NMe_2$ |
| $CH_2SMe$ | $CH_2SMe$ | $CH_2SMe$ |
| $CH_2OCH_2CF_3$ | $CH_2OCH_2CF_3$ | $CH_2OCH_2CF_3$ |
| $CH_2SiMe_3$ | $CH_2SiMe_3$ | $CH_2SiMe_3$ |
| $CH_2NMe_2$ | $CH_2NMe_2$ | $CH_2NMe_2$ |
| $CH_2$-2-pyridyl | $CH_2$-2-pyridyl | $CH_2$-2-pyridyl |
| 2-pyridyl | 2-pyridyl | 2-pyridyl |
| 3-pyridyl | 3-pyridyl | 3-pyridyl |
| 2-thienyl | 2-thienyl | 2-thienyl |
| 3-thienyl | 3-thienyl | 3-thienyl |
| 2-oxazolinyl | 2-oxazolinyl | 2-oxazolinyl |
| 2-(1,3-dioxolanyl) | 2-(1,3-dioxolanyl) | 2-(1,3-dioxolanyl) |
| A is $OCH_2$; | A is $OCH_2$; | A is $NHCH_2$; |
| $R^2$ is 5-Cl; | $R^2$ is 5-$CF_3$; | $R^2$ is 4-F |
| $R^3$ | $R^3$ | $R^3$ |
| CN | CN | CN |
| $NO_2$ | $NO_2$ | $NO_2$ |
| $N_3$ | $N_3$ | $NMe_2$ |
| Br | Br | $NHCO_2Me$ |
| $NMe_2$ | $NMe_2$ | epoxyethyl |
| $NHCO_2Me$ | $NHCO_2Me$ | $SiMe_3$ |
| epoxyethyl | epoxyethyl | SMe |
| epoxyisopropenyl | epoxyisopropenyl | $P(O)(OMe)_2$ |
| $SiMe_3$ | $SiMe_3$ | $CH_2SMe$ |
| SMe | SMe | $CH_2OCH_2CF_3$ |
| S(O)Me | S(O)Me | $CH_2SiMe_3$ |
| $SO_2Me$ | $SO_2Me$ | 2-pyridyl |
| $P(O)(OMe)_2$ | $P(O)(OMe)_2$ | 2-thienyl |
| $CH_2C(O)NMe_2$ | $CH_2C(O)NMe_2$ | |
| $CH_2SMe$ | $CH_2SMe$ | |
| A is $OCH_2$; | A is $OCH_2$; | A is $NHCH_2$; |
| $R^2$ is 5-Cl; | $R^2$ is 5-$CF_3$; | $R^2$ is 5-F; |
| $R^3$ | $R^3$ | $R^3$ |
| $CH_2OCH_2CF_3$ | $CH_2OCH_2CF_3$ | CN |
| $CH_2SiMe_3$ | $CH_2SiMe_3$ | $NO_2$ |
| $CH_2NMe_2$ | $CH_2NMe_2$ | $NMe_2$ |
| $CH_2$-2-pyridyl | $CH_2$-2-pyridyl | $NHCO_2Me$ |
| 2-pyridyl | 2-pyridyl | epoxyethyl |
| 3-pyridyl | 3-pyridyl | $SiMe_3$ |
| 2-thienyl | 2-thienyl | SMe |
| 3-thienyl | 3-thienyl | $P(O)(OMe)_2$ |
| 2-oxazolinyl | 2-oxazohnyl | $CH_2SMe$ |
| 2-(1,3-dioxolanyl) | 2-(1,3-dioxolanyl) | $CH_2OCH_2CF_3$ |
| $C(H)=NOCH_3$ | $C(SCH_3)=N(OCH_3)$ | $CH_2SiMe_3$ |
| $C(CH_3)=NOCH_3$ | $C(H)=NOCH_3$ | 2-pyridyl |
| $C(Cl)=NOCH_3$ | $C(H)=NOCH_2CH_3$ | 2-thienyl |
| $C(CN)=NOCH_3$ | $C(CH_3)=NOCH_3$ | |
| $C(OCH_3)=NOCH_3$ | $C(H)=NOH$ | |
| A is $NHCH_2$; | A is $N(Me)CH_2$; | A is $N(Me)CH_2$; |
| $R^2$ is 5-Cl; | $R^2$ is 4-F; | $R^2$ is 5-Cl |
| $R^3$ | $R^3$ | $R^3$ |
| CN | CN | CN |
| $NO_2$ | $NO_2$ | $NO_2$ |
| $NMe_2$ | $NMe_2$ | $NMe_2$ |
| $NHCO_2Me$ | $NHCO_2Me$ | $NHCO_2Me$ |
| epoxyethyl | epoxyethyl | epoxyethyl |
| $SiMe_3$ | $SiMe_3$ | $SiMe_3$ |
| SMe | SMe | SMe |
| $P(O)(OMe)_2$ | $P(O)(OMe)_2$ | $P(O)(OMe)_2$ |
| $CH_2SMe$ | $CH_2SMe$ | $CH_2SMe$ |
| $CH_2OCH_2CF_3$ | $CH_2OCH_2CF_3$ | $CH_2OCH_2CF_3$ |
| $CH_2SiMe_3$ | $CH_2SiMe_3$ | $CH_2SiMe_3$ |
| 2-pyridyl | 2-pyridyl | 2-pyridyl |
| 2-thienyl | 2-thienyl | 2-thienyl |
| A is $NHCH_2$; | A is $N(Me)CH_2$; | A is $N(Me)CH_2$; |
| $R^2$ is 5-$CF_3$; | $R^2$ is 5-F; | $R^2$ is 5-$CF_3$; |
| $R^3$ | $R^3$ | $R^3$ |
| CN | CN | CN |
| $NO_2$ | $NO_2$ | $NO_2$ |
| $NMe_2$ | $NMe_2$ | $NMe_2$ |
| $NHCO_2Me$ | $NHCO_2Me$ | $NHCO_2Me$ |
| epoxyethyl | epoxyethyl | epoxyethyl |
| $SiMe_3$ | $SiMe_3$ | $SiMe_3$ |
| SMe | SMe | SMe |
| $P(O)(OMe)_2$ | $P(O)(OMe)_2$ | $P(O)(OMe)_2$ |
| $CH_2SMe$ | $CH_2SMe$ | $CH_2SMe$ |
| $CH_2OCH_2CF_3$ | $CH_2OCH_2CF_3$ | $CH_2OCH_2CF_3$ |
| $CH_2SiMe_3$ | $CH_2SiMe_3$ | $CH_2SiMe_3$ |
| 2-pyridyl | 2-pyridyl | 2-pyridyl |
| 2-thienyl | 2-thienyl | 2-thienyl |
| $C(H)=NOCH_3$ | $C(CH_3)=NOCH_3$ | $C(OCH_3)=NOCH_3$ |

Formulation and Use

The Compounds of this invention will generally be used in formulation with an agriculturally suitable carrier comprising a liquid or solid diluent or an organic solvent. Useful formulations of the compounds of Formulas I and II can be prepared in conventional ways. They include dusts, granules, baits, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain from less than about 1% to 99% by weight of active ingredient(s) and at least one of a) about 0.1% to 20% surfactant(s) and b) about 5% to 99% solid or liquid diluent(s). More specifically, they will contain effective amounts of these ingredients in the following approximate proportions:

| | Percent by Weight | | |
|---|---|---|---|
| | Active Ingredient | Diluent(s) | Surfactant(s) |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, U.S. Pat. No. 3,060,084). Granules and pellets can be made by spraying the active material upon preformed granular carriers or by agglomeration techniques. See J. E. Browning, "Agglomeration", *Chemical Engineering*-, Dec. 4, 1967, pages 147 and following, and "Perry's Chemical Engineer's Handbook", 4th Ed., McGraw-Hill, New York, 1963, pages 8 to 59 and following.

| Emulsifiable Concentrate | |
|---|---|
| 7-chloro-,3a-cyano-3a,4-dihydro-N-[4-(trifluoromethyl)phenyl][1]benzopyrano-[4,3-C]pyrazole-2(3H)-carboxamide | 20% |
| blend of oil soluble sulfonates and polyoxyethylene ethers | 10% |
| isophorone | 70% |

The ingredients are combined and stirred with gentle warming to speed solution. A fine screen filter is included in packaging operation to insure the absence of any extraneous undissolved material in the product.

| Wettable Powder | |
|---|---|
| 7-chloro-,3a-cyano-3a,4-dihydro-N-[4-(trifluoromethyl)phenyl][1]benzopyrano-[4,3-C]pyrazole-2(3H)-carboxamide | 30% |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammer-mill, the material is re-blended and sifted through a 50 mesh screen.

| Dust | |
|---|---|
| Wettable powder of Example B | 10% |
| pyrophyllite (powder) | 90% |

The wettable powder and the pyrophyllite diluent are thoroughly blended and then packaged. The product is suitable for use as a dust.

| Granule | |
|---|---|
| 7-chloro-2,3,3a,4-tetrahydro-3a-oxiranyl-N-[4-(trifluoromethyl)phenyl][1]benzopyrano-[4,3-C]pyrazole-2-carboxamide | 10% |
| attapulgite granules (low volative matter, 0.71/0.30 mm; U.S.S. No. 25–50 sieves) | 90% |

The active ingredient is dissolved in a volatile solvent such as acetone and sprayed upon dedusted and pre-warmed attapulgite granules in a double cone blender. The acetone is then driven off by heating. The granules are then allowed to cool and are packaged.

| Granule | |
|---|---|
| Wettable powder of Example B | 15% |
| gypsum | 69% |
| potassium sulfate | 16% |

The ingredients are blended in a rotating mixer and water sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 4.5% active ingredient.

| Solution | |
|---|---|
| 7-chloro-2,3,3a,4-tetrahydro-3a-oxiranyl-N-[4-(trifluoromethyl)phenyl][1]benzopyrano-[4,3-C]pyrazole-2-carboxamide | 25% |
| N-methyl-pyrrolidone | 75% |

The ingredients are combined and stirred to produce a solution suitable for direct, low volume application.

| Aqueous Suspension | |
|---|---|
| 3a-(5-chloro-2-thienyl)-3a,4-dihydro-F-(trifluoromethyl)-N-[4-(trifluoromethyl)phenyl][1]benzopyrano-[4,3-C]pyrazole-2(3H)-carboxamide | 40% |
| polyacrylic acid thickener | 0.3% |
| dodecyclophenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles substantially all under 5 microns in size.

| Oil Suspension | |
|---|---|
| 7-chloro-2,3,3a,4-tetrahydro-3a-oxiranyl-N-[4-(trifluoromethyl)phenyl][1]benzopyrano-[4,3-C]pyrazole-2-carboxamide | 35.0% |
| blend of polyalcohol carboxylic esters and oil soluble petroleum sulfonates | 6.0% |
| | 59.0% |

-continued

| Oil Suspension |
|---|
| xylene range solvent |

The ingredients are combined and ground together in a sand mill to produce particles substantially all below 5 microns. The product can be used directly, extended with oils, or emulsified in water.

| Bait Granules | |
|---|---|
| 2-(2,3,3a,8a-tetrahydrocyclopent[a]inden-8(1H)-ylidene-N-[4-(trifluoromethyl)phenyl]hydrazinecarboxamide | 25% |
| blend of polyethoxylated nonylphenols and sodium dodecylbenzene sulfonates | 9.0% |
| ground up corn cobs | 88.0% |

The active ingredient and surfactant blend are dissolved in a suitable solvent such as acetone and sprayed onto the ground corn cobs. The granules are then dried end packaged.

Compounds of Formulas I and H can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of this invention can be formulated are:

Insecticides 3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl O-(methylcarbamoyl)thiolacetohydroxamate (methomyl)
N'-(4-chloro-o-tolyl)-N,N-dimethylformamidine (chlordimeform)
O,O-diethyl-O-(2-isopropyl-4-methyl-6-pyrimidylphosphorothioate (diazinon)
octachlorocamphene (toxaphene)
O-ethyl-O-p-nitrophenyl phenylphosphonothioate (EPN)
(S)-α-cyano-m-phenoxybenzyl(1R,3R)-3-(2,2-dibromovinyl)-2,2-dimethylcyclopropanecarboxylate (deltamethrin)
Methyl-N',N'-dimethyl-N-[(methylcarbamoyl)oxy]-1-thioox amimidate (oxamyl)
cyano(3-phenoxyphenyl)-methyl-4-chloro-α(1-methylethyl)benzeneacetate (fenvalerate)
(3-phenoxyphenyl)methyl(+)-cis,trans-3-(2,2-dichloro ethenyl)-2,2-dimethylcyclopropanecarboxylate (permethrin)
α-cyano-3-phenoxybenzyl 3-(2,2-dichlorovinyl)-2,2-dimethylcyclopropane carboxylate (cypermethrin)
O-ethyl-S-(p-chlorophenyl)ethylphosphonodithioate (profenofos)
phosphorothiolothionic acid, O-ethyl-O-[4-(methylthio)-phenyl]-S-n-propyl ester (sulprofos).

Additional insecticides are listed hereafter by their common names: triflumuron, diflubenzuron, methoprene, buprofezin, thiodicarb, acephate, azinphosmethyl, chlorpyrifos, dimethoate, fonophos, isofenphos, methidathion, methamidiphos, monocrotphos, phosmet, phosphamidon, phosalone, pirimicarb, phorate, terbufos, trichlorfon, methoxychlor, bifenthrin, biphenate, cyfluthrin, fenpropathrin, fluvalinate, flucythrinate, tralomethrin, metal-dehyde and rotenone.

Fungicides:

methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2-ylmethyl]-1H-1,2,4-triazole (propiconazole)
2-cyano-N-ethylcarbamoyl-2-methoxyiminoacetamide (cymoxanil)
1-(4-chlorophenoxy)-3,3-dimethyl-1-(1H-1,2,4-triazol-1-yl)-2-butanone (triadimefon)
N-(trichloromethylthio)tetrahydrophthalimide (captan)
N-(trichloromethylthio)phthalimide (folpet)
1-[[[bis(4-fluorophenyl)][methyl]silyl]methyl]-1H-1,2,4-triazole.

Nematocides:

S-methyl 1-(dimethylcarbamoyl)-N-(methylcarbamoyloxy)-thioformimidate
S-methyl 1-carbamoyl-N-(methylcarbamoyloxy)-thioformimidate
N-isopropylphosphoramidic acid O-ethyl O'-[4-(methylthio)-m-tolyl]diester (fenamiphos)

Bactericides:

tribasic copper sulfate
streptomycin sulfate

Acaricides:

senecioic acid, ester with 2-sec-butyl-4,6-dinitro-phenol (binapacryl)
6-methyl-1,3-cithiolo[4,5-β]quinoxalin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl)(dienochlor)
tricyclohexyltin hydroxide (cyhexatin)
trans-5-(4-chlorophenyl)-N-cyclohexyl-4-methyl-2-oxo-thiazolidine-3-carboxamide (hexythiazox)
amitraz
propargite
fenbutatin-oxide Biological

*Bacillus thuringiensis*
Avermectin B.

Utility

The compounds of this invention exhibit activity against a wide spectrum of foliar and soil inhabiting arthropods which are pests of growing and stored agronomic crops, forestry, greenhouse crops, ornamentals, nursery crops, stored food and fiber products, livestock, household, and public and animal health. Those skilled in the art will recognize that not all compounds are equally effective against all pests but the compounds of this invention display activity against economically important agronomic, forestry, greenhouse, ornamental food and fiber product, stored product, domestic structure, and nursery pests, such as:

larvae of the order Lepidoptera including fall and beet armyworm and other *Spodoptera spp.*, tobacco budworm, corn earworm and other *Heliothis spp.*, European corn borer, navel orangeworm, stalk/stem borers and other pyralids, cabbage and soybean loopers And other loopers, codling moth, grape berry moth and other tortricids, black cutworm, spotted cutworm, other cutworms And other noctuids, diamondback moth, green cloverworm, velvetbean caterpillar, green cloverworm, pink bollworm, gypsy moth, and spruce budworm;

foliar feeding larvae and adults of the order Coleoptera including Colorado potato beetle, Mexican bean beetle, flea beetle, Japanese beetles, and other leaf beetles, boll weevil, rice water weevil, granary weevil, rice weevil and other weevil pests, and soil inhabiting insects such as Western corn rootworm and other *Diabrotica spp.*, Japanese beetle, European chafer and other coleopteran grubs, and wireworms;

adults and larvae of the orders Hemiptera and Homoptera including tarnished plant bug and other plant bugs (miridae), aster leafhopper and other leafhoppers (cicadellidae), rice planthopper, brown planthopper, and other planthoppers (fulgoroidea), psylids, whiteflies (aleurodidae), aphids (aphidae), scales (coccidae and diaspididae), lace bugs (tingidae), stink bugs (pentatomidae), cinch bugs and other seed bugs (lygaeidae), cicadas (cicadidae), spittlebugs (cercopids), squash bugs (coreidae), red bugs and cotton stainers (pyrrhocoridae);

adults and larvae of the order acari (mites) including European red mite, two spotted spider mite, rust mites, McDaniel mite, and foliar feeding mites;

adults and immatures of the order Orthoptera including grasshoppers;

adults and immatures of the order Diptera including leafminers, midges, fruit flies (tephritidae), and soft maggots;

adults and immatures of the order Thysanoatera including onion thrips and other foliar feeding thrips.

The compounds are also active against economically important livestock, household, public and animal health pests such as:

insect pests of the order Hymenoptera including carpenter ants, bees, hornets, and wasps;

insect pests of the order Diptera including house flies, stable flies, face flies, horn flies, blow flies, and other muscoid fly pests, horse flies, deer flies and other Brachycera, mosquitoes, black flies, biting midges, sand flies, sciarids, and other Nematocera;

insect pests of the order Orthoptera including cockroaches and crickets;

insect pests of the order Isoptera including the Eastern subterranean termite and other termites;

insect pests of the order Mallophaga and Anoplura including the head louse, body louse, chicken head louse and other sucking and chewing parasitic lice that attack man and animals;

insect pests of the order Siphonoptera including the cat flea, dog flea and other fleas.

The specific species for which control is exemplified are: fall armyworm, *Spodoptera fruigiperda*; tobacco budworm, *Heliothis virescens*; boll weevil, *Anthonomus grandis*; aster leafhopper, *Macrosteles fascifrons*; black bean aphid, (*Aphis fabae*); southern corn rootworm, *Diabrotica undecimpunctata*. The pest control protection afforded by the compounds of the present invention is not limited, however, to these species. The compounds of this invention may also be utilized as rodenticicles.

Application

Arthropod pests are controlled and protection of agronomic crops, animal and human health is achieved by applying one or more of the Formula I or II compounds of this invention, in an effective amount, to the environment of the pests including the agronomic and/or nonagronomic locus of infestation, to the area to be protected, or directly on the pests to be controlled. Because of the diversity of habitat and behavior of these arthropod pest species, many different methods of application are employed. A preferred method of application is by spraying with equipment that distributes the compound in the environment of the pests, on the foliage, animal, person, or premise, in the soil or animal, to the plant part that is infested or needs to be protected. Alternatively, granular formulations of these toxicant compounds can be applied to or incorporated into the soil. Other methods of application can also be employed including direct and residual sprays, aerial sprays, baits, eartags, boluses, loggers, aerosols, and many others. The compounds can be incorporated into baits that are consumed by the arthropods or in devices such as traps and the like which entice them to ingest or otherwise contact the compounds.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrates, and synergists such as piperonyl butoxide often enhance the efficacy of the compounds of Formula I and II.

The rate of application of the Formula I and II compounds required for effective control will depend on such factors as the species of arthropod to be controlled, the pest's life cycle, life stage, its size, location, time of year, host crop or animal, feeding behavior, mating behavior, ambient moisture, temperature, etc. In general, application rates of 0.01 to 2 kg of active ingredient per hectare are sufficient to provide large-scale effective control of pests in agronomic ecosystems under normal circumstances, but as little as 0.001 kg/hectare or as much as 8 kg hectare may be required. For nonagronomic applications, effective use rates will range from about 1.0 to 50 mg/square meter but as little as about 0.1 mg/square meter or as much as 150 mg/square meter may be required.

The following Tests demonstrate the control efficacy of compounds of Formula I and II on specific pests; see Index Tables A through I for compound descriptions. Compounds not included in the tests had activities that gave <80% mortality or were not screened.

INDEX TABLE A

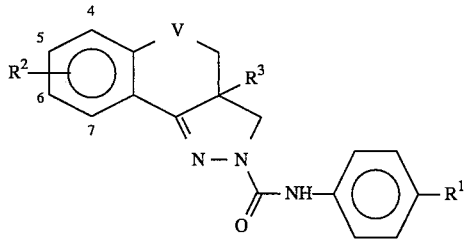

| CMPD | Y | R¹ | R² | R³ | mp (°C.) |
|---|---|---|---|---|---|
| 1 | CH₂ | CF₃ | 5-Cl | CN | 227–229 |
| 2 | CH₂ | CF₃ | CF₃ | CN | 220–222 |
| 3 | CH₂ | CF₃ | CF₃ | NHCO₂Me | 271–272 |

INDEX TABLE A

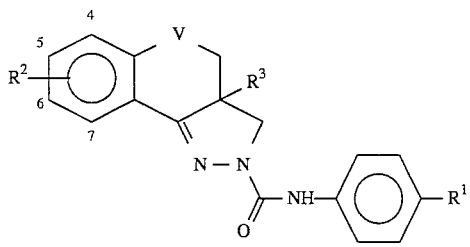

| CMPD | Y | R¹ | R² | R³ | mp (°C.) |
|---|---|---|---|---|---|
| 4 | O | CF₃ | 5-CF₃ | 2-oxazolinyl | 247–251 |
| 5 | O | CF₃ | 5-CF₃ | CN | 265–269 |
| 6 | O | CF₃ | 5-CF₃ | NHCO₂Me | >245 |
| 7 | O | CF₃ | 5-CF₃ | 2-Cl-thienyl | 184–187 |
| 8 | O | CF₃ | 5-Cl | CH₂SiMe₃ | 152–154 |
| 9 | O | CF₃ | 5-Cl | epoxyethyl isomer 1 | 187–190[a] |
| 10 | O | CF₃ | 5-Cl | epoxyethyl isomer 2 | 79–81[a] |
| 11 | O | CF₃ | H | epoxyethyl isomer 1 | 159–162[a] |
| 12 | O | CF₃ | H | epoxyethyl isomer 2 | 135–138[a] |
| 36 | O | CF₃ | CF₃ | C(H)=NOCH₃ | 155–159 |

[a] Two diastereoisomers were isolated after column chromatography of these compounds.

INDEX TABLE B

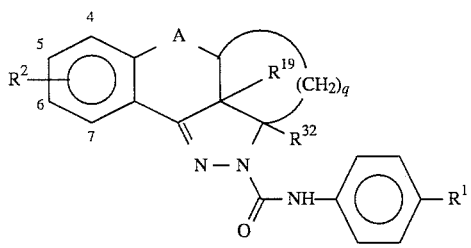

| CMPD | V | R¹ | R² | R¹⁹ | R³² | q | mp (°C.) |
|---|---|---|---|---|---|---|---|
| 13 | O | CF₃ | 5-Cl | H | H | 3 | 208–209 |
| 14 | O | Cl | 5-Cl | H | H | 3 | 166–167 |
| 15 | O | CF₃ | 4-F | H | H | 3 | 197–198 |
| 16 | O | Cl | 4-F | H | H | 3 | 175–177 |
| 17 | O | Cl | 5-CF₃ | H | H | 3 | 170–171 |
| 18 | O | CF₃ | 5-CF₃ | H | H | 3 | 194–195 |
| 19 | O | CF₃ | 5-Cl | Me | H | 3 | 69–71 |
| 20 | O | CF₃ | 5-Cl | H | H | 4 | 240–242 |
| 21 | O | Br | 5-Cl | H | H | 4 | 250–252 |
| 22 | O | CF₃ | 5-Cl | iPr | H | 3 | 141–142 |
| 23 | O | CF₃ | 5-Cl | Ph | H | 3 | semi-solid |
| 24 | O | CF₃ | 5-Cl | H | CO₂Me | 3 | 196–199 |
| 25 | O | CF₃ | 5-CF₃ | CO₂Me | H | 3 | 190–192 |
| 26 | O | CF₃ | 5-Cl | CO₂Me | H | 3 | 114–117 |
| 27 | O | CF₃ | 5-CF₃ | Me | H | 3 | 64–65 |
| 28 | O | CF₃ | 5-CF₃ | iPr | H | 3 | semi-solid |
| 29 | O | CF₃ | 5-Cl | CH₂OH | H | 3 | 115–117 |

INDEX TABLE C

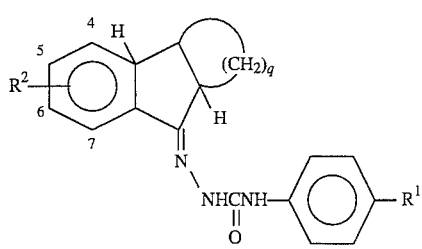

| CMPD | R¹ | R² | q | mp (°C.) |
|---|---|---|---|---|
| 30 | CF₃ | H | 3 | 214–215 |
| 31 | Br | H | 3 | 221–223 |
| 32 | Cl | H | 3 | 230–233 |
| 33 | CF₃ | 5-Cl | 4 | 218–223 |
| 34 | Cl | 5-Cl | 4 | 232–243 |
| 35 | Br | 5-Cl | 4 | 231–235 |

INDEX TABLE D

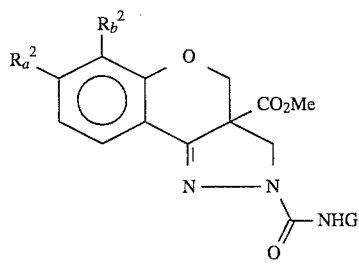

| CMPD | G | R¹ | R$_a^2$ | R$_b^2$ | mp (°C.) |
|---|---|---|---|---|---|
| 37 | G-2 | Cl | CF₃ | H | 236–238 |
| 38 | G-1 | CF₃ | CF₃ | H | 194–195 |
| 39 | G-1 | Cl | CF₃ | H | 196–198 |
| 40 | G-1 | Br | CF₃ | H | 179–181 |
| 41 | G-1 | H | CF₃ | H | 193–197 |
| 42 | CH₂Ph | CF₃ | CF₃ | H | 165–167 |
| 43 | CH₂Ph | OCF₃ | CF₃ | H | 137–139 |
| 44 | CH₂Ph | Br | CF₃ | H | 159–161 |
| 45 | CH₂Ph | Cl | CF₃ | H | 65–67 |
| 46 | CH₂Ph | F | CF₃ | H | 64–66 |
| 47 | CH₂CH₂Ph | H | CF₃ | H | 54–56 |
| 48 | G-2 | OMe | CF₃ | H | 78–81 |
| 49 | CH₂CH₂Ph | Cl | CF₃ | H | 54–56 |
| 50 | G-4 | Cl | CF₃ | H | 212–214 |
| 51 | G-10 | Cl | CF₃ | H | 180–182 |
| 52 | G-10 | Br | CF₃ | H | 189–191 |

INDEX TABLE E

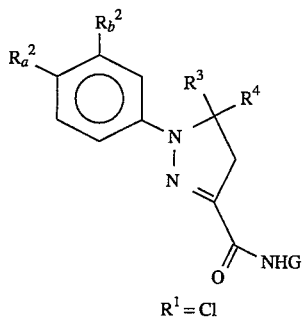

$R^1 = Cl$

| CMPD | G | $R_a^2$ | $R_b^2$ | $R^3$ | $R^4$ | mp (°C.) |
|---|---|---|---|---|---|---|
| 53 | G-2 | Cl | H | Me | CO₂Me | 174–177 |
| 54 | G-2 | Cl | H | 4-F-Ph | H | 191–193 |

INDEX TABLE F

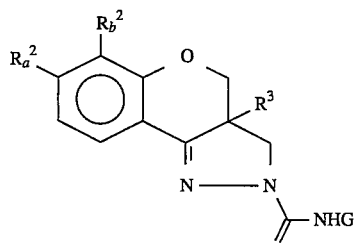

| CMPD | G | $R^1$ | $R_a^2$ | $R_b^2$ | $R^3$ | mp (°C.) |
|---|---|---|---|---|---|---|
| 55 | G-2 | Cl | H | H | c-Hex | Oil |
| 56 | G-2 | Cl | Cl | H | c-Hex | Oil |
| 57 | G-2 | Cl | Cl | H | 4-F-Ph | 230–232 |
| 58 | G-2 | Cl | Cl | H | i-Pr | 218–220 |
| 59 | G-1 | Cl | Cl | H | i-Pr | 167–169 |
| 60 | G-1 | Br | Cl | H | i-Pr | 145–147 |
| 61 | G-1 | Cl | Cl | H | 4-F-Ph | 218–220 |
| 62 | G-1 | Br | Cl | H | 4-F-Ph | 210–212 |
| 63 | G-1 | CF₃ | Cl | H | 4-F-Ph | >250° C. |
| 64 | G-2 | Cl | Cl | H | 4-Cl-Ph | >250° C. |
| 65 | G-1 | Cl | Cl | H | 4-Cl-Ph | 214–217 |
| 66 | G-1 | CF₃ | Cl | H | 4-Cl-Ph | 250–252 |
| 67 | G-2 | Cl | H | F | 4-F-Ph | 234–236 |

INDEX TABLE G

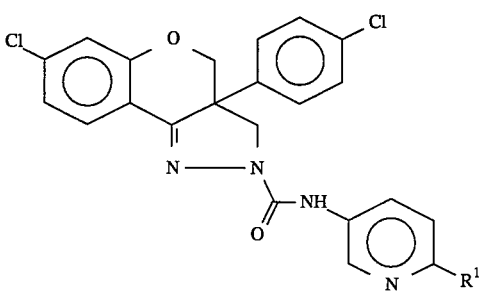

| CMPD | $R^1$ | mp (°C.) |
|---|---|---|
| 68 | —O—⟨C₆H₄⟩—F | 119–121 |
| 78 | —S—⟨C₆H₄⟩—F | 194–196 |

INDEX TABLE H

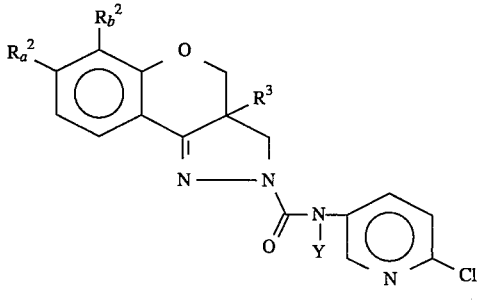

| CMPD | Y | $R_a^2$ | $R_b^2$ | $R^3$ | mp (°C.) |
|---|---|---|---|---|---|
| 69 | COMe | Cl | H | 4-F-Ph | 121–123 |
| 70 | COMe | Cl | H | 4-Cl-Ph | oil |
| 71 | COMe | H | F | 4-F-Ph | oil |
| 72 | COCH₂CH₃ | Cl | H | 4-F-Ph | oil |
| 73 | CO₂Me | Cl | H | 4-F-Ph | oil |

INDEX TABLE I

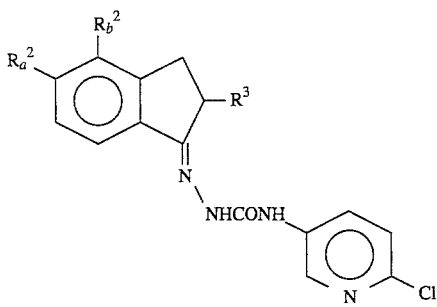

| CMPD | $R_a^2$ | $R_b^2$ | $R^3$ | mp (°C.) |
|---|---|---|---|---|
| 74 | Cl | H | 4-Cl-Ph | 207–209 |
| 75 | F | H | 4-F-Ph | 201–204 |
| 76 | Cl | H | n-Pr | 218–220 |
| 77 | H | F | 4-F-Ph | 224–226 |

TEST A

Fall Armyworm

Test units, each consisting of an 8-ounce (230 mL) plastic cup containing a layer of wheat germ diet, approximately 0.5 cm thick, were prepared. Five third-instar larvae of fall armyworm (*Spodoptera frugiperda*) were placed into each cup. Solutions of each of the test compounds (acetone/distilled water 75/25 solvent) were sprayed into the cups. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i. (207 kPa). The cups were then covered and held at 27° C. and 50% relative humidity for 72 hours, after which time readings were taken. Of the compounds tested, the following gave mortality levels of 80% or higher: 1, 4, 5, 6, 7, 8, 10, 13, 14, 17, 18, 19, 20, 22, 23, 24, 26, 27, 28, 29, 30, 33, 36, 37, 38, 40, 51, 54, 55, 57, 58, 60, 61, 62, 63, 64, 65, 66, 67, 68, 69, 70, 72, 73, 74, 75, and 78.

TEST B

Tobacco Budworm

The test procedure of Test A was repeated for efficacy against third-instar larvae of the tobacco budworm (*Heliothis virescens*) except that mortality was assessed at 48 hours. Of the compounds tested, the following gave mortality level of 80% or higher: 1, 4, 5, 6, 7, 8, 9, 10, 13, 14, 15, 16, 17, 18, 19, 20, 22, 23, 24, 26, 27, 28, 33, 34, 36, 37, 38, 39, 40, 54, 57, 58, 59, 61, 62, 63, 64, 65, 66, 67, 68, 69, 70, 71, 72, 73, 74, 75 and 78.

TEST C

Southern Corn Rootworm

The units, each consisting of an 8-ounce (230 mL) plastic cup containing 1 sprouted corn seed, were prepared. Test units were sprayed as described in Test A with individual solutions of the test compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken: Of the compounds tested, the following gave mortality levels of 80% or higher: 1, 2, 4, 5, 6, 7, 8, 9, 11, 13, 14, 18, 19, 21, 22, 23, 28, 30, 31, 32, 33, 34, 35, 36, 37, 39, 54, 57, 58, 63, 64, 67, 68, 69, 71, 72, 73, 74, 75, 76, 77 and 78.

TEST D

Aster Leafhopper

Test units were prepared from a series of 12-ounce (350 mL) cups, each containing oat (*Arena sativa*) seedlings in a 1-inch (2.54 cm) layer of sterilized soil. The test units were sprayed as described in Test A with individual solutions of the below-listed compounds. After the oats had dried from the spraying, between 10 and 15 adult aster leafhoppers (*Mascrosteles fascifrons*) were aspirated into each of the covered cups. The cups were held at 27° C. and 50% relative humidity for 48 hours, after which time mortality readings were taken. Of the compounds tested, the following gave mortality levels of 80% or higher: 1, 9, 10, 13, 14, 17, 18, 19, 20, 22, 23, 30, 31, 33, 36, 57, 58, 64, 67, 69, 70, 71, 72, 73 and 74.

TEST E

Boll Weevil

Five adult boll weevils (*Anthonomus grandis grandis*) were placed into each of a series of 9 ounce (260 mL) cups. The test procedure employed was then otherwise the same as in Test A. Mortality readings were taken 48 hours after treatment. Of the compounds tested, the following gave mortality levels of 80% or higher: 1, 2, 4, 5, 8, 9, 10, 13, 14, 16, 17, 19, 23, 26, 27, 30, 33, 36, 37, 38, 39, 57, 58, 64, 67, 69, 70, 71, 72, 73 and 74.

TEST F

Black Bean Aphid

Individual nasturtium leaves were infested with 5 to 10 aphids (all stages of *Aphis fabae*) and sprayed with their undersides facing up on a hydraulic sprayer as described in Test A. The leaves were then set in 1-inch diameter vials containing sugar water solution and covered with a clear plastic 1 oz-portion cup to prevent escape of aphids that drop from the leaves. The test units were held at 27° C. and 50% relative humidity for 48 hours, after which time mortality readings were taken. Of the compounds tested, the following gave mortality levels of 80% or higher: 63 and 78.

TEST G

Two-Spotted Spider Mite

One inch squares of kidney bean leaves that have been infested on the undersides with 25 to 30 adult mites (*Tetranychus urtical*) were sprayed with their undersides facing up on a hydraulic sprayer as described in Test A. The leaf squares were placed underside up on a square of wet cotton in a petri dish and the perimeter of the leaf square was tamped down onto the cotton with forceps so that the mites cannot escape onto untreated leaf surface. The test units were held at 27° C. and 50% relative humidity for 48 hours, after which time mortality readings were taken. Of the compounds tested, Compounds 23 and 69 produced mortality levels of greater than 80%.

We claim:
1. A compound selected from

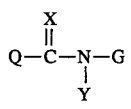

and

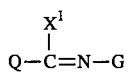

wherein

Q is selected from the group

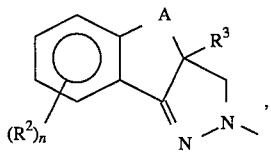

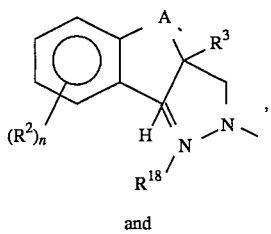

and

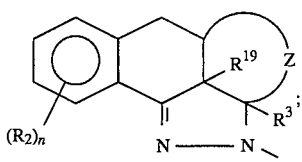

A is selected from the group $CH_2$ and $CH_2CH_2$, each optionally substituted with substituents independently selected from 1 to 2 halogen and methyl;

G is selected from the group

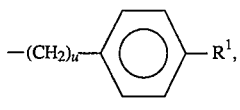

and

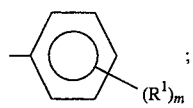

X is selected from the group O and S;

$X^1$ is selected from the groups Cl, Br, $OR^6$, $SR^6$ and $N(R^6)R^7$;

Y is H;

$R^1$ and $R^2$ are independently selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, $N_3$, SCN, $NO_2$, $OR^{15}$, $SR^{15}$, $S(O)R^{15}$, $S(O)_2R^{15}$, $OC(O)R^{15}$, $OS(O)_2R^{15}$, $CO_2R^{15}$, $C(O)R^{15}$, $C(O)N(R^{15})R^{16}$, $SO_2N(R^{15})R^{16}$, $N(R^{15})R^{16}$, $N(R^{16})C(O)R^{15}$, $OC(O)NHR^{15}$, $N(R^{16})C(O)NHR^{15}$, $N(R^{16})SO_2R^{15}$, phenyl optionally substituted with 1 to 3 substituents independently selected from W and benzyl optionally substituted with 1 to 3 substituents independently selected from W; or when m, n or p is 2, $(R^1)_2$ can be taken together, or $(R^2)_2$ can be taken together or $(R^{14})_2$ can be taken together as —$6OCH_2O$, —$OCF_2O$, $OCH_2CH_2O$, $CF_2CF_2O$, —$CH_2C(CH_3)_2O$— or —$OCF_2CF_2O$— to form a cyclic bridge between adjacent atoms on the same ring;

$R^3$ is selected from the group consisting of pyrrolyl, pyrazolyl, imidazolyl, pyridyl, pyrazinyl, pyrimidinyl, and pyridazinyl, containing one carbonyl and optionally containing one substituent group selected from W;

Z is $(CH_2)_q$ where q is 2–4, wherein said group is optionally substituted with 1–2 $CH_3$;

$R^{18}$ is selected from the group H, $C_1$–$C_4$ alkyl, $C_1$–$C_4$ haloalkyl, $C_2$–$C_4$ alkylcarbonyl, $C_2$–$C_4$ haloalkylcarbonyl, $C_2$–$C_4$ alkoxycarbonyl, $C_2$–$C_4$ haloalkoxycarbonyl, $C_2$–$C_5$ alkylaminocarbonyl, $C_3$–$C_6$ cycloalkyl, $C_3$–$C_6$ halocycloalkyl, $C_4$–$C_7$ alkylcycloalkyl, $C_4$–$C_7$ haloalkylcycloalkyl, $C_1$–$C_4$ alkylsulfonyl, $C_1$–$C_4$ haloalkylsulfonyl and $SO_2Ph$ optionally substituted with Cl, Br or $CH_3$;

$R^{19}$ is selected from the group H, $C_1$–$C_3$ alkyl, $CO_2R^{18}$, phenyl and phenyl substituted with W;

$R^6$ is selected from the group $C_1$–$C_3$ alkyl, $C_2$–$C_4$ alkenyl, $C_2$–$C_4$ alkynyl, $C_1$–$C_3$ haloalkyl, $C_2$–$C_4$ haloalkenyl, $C_3$–$C_6$ cycloalkyl and $C_1$–$C_3$ alkyl substituted with $OCH_3$, $OCH_2CH_3$, $NO_2$, CN, $CO_2CH_3$, $CO_2CH_2CH_3$, $SCH_3$ or $SCH_2CH_3$; benzyl optionally substituted with the group halogen, CN, $C_1$–$C_3$ haloalkyl and $C_1$–$C_3$ haloalkoxy;

$R^7$ is selected from the group H, $C_1$–$C_4$ alkyl, $C_1$–$C_4$ haloalkyl, $C_2$–$C_4$ alkoxycarbonyl, optionally substituted phenyl and optionally substituted pyridinyl wherein the substituent(s) are selected from the group halogen, CN, $C_1$–$C_3$ haloalkyl and $C_1$–$C_3$ haloalkoxy;

$R^{15}$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, optionally substituted phenyl and optionally substituted benzyl wherein the substituent(s) are 1 to 3 substituents independently selected from W;

$R^{16}$ is selected from H and $C_1$–$C_4$ alkyl;

W is selected from the group halogen, CN, $NO_2$, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, $C_1$–$C_2$ alkylsulfonyl and $C_1$–$C_2$ haloalkylsulfonyl;

m is 1 to 3;

n is 1 to 3; and u is 1 or 2.

2. A compound according to claim 1 wherein:

$R^1$ is selected from the group H, halogen, CN, SCN, $NO_2$, $OR^{15}$, $SR^{15}$, $SO_2R1^5$, $CO_2R^{15}$, $C(O)R^{15}$, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycoalkyl, phenyl optionally substituted with 1 to 3 substituents independently selected from W, and benzyl optionally substituted with 1 to 3 substituents independently selected from W;

$R^2$ is selected from the group H, halogen, CN, SCN, $NO_2$, $OR^{15}$, $SR^{15}$, $S(O)_2R^{15}$, $OC(O)R^{15}$, $OS(O)_2R^{15}$, $CO_2R^{15}$, $C(O)R^{15}$, $C(O)N(R^5)R^{16}$, $SO_2N(R^{15})R^{16}$, $N(R^{15})R^{16}$, $C_1$–$C_6$ alkyl, $C_1$–C haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, phenyl optionally substituted with 1 to 3 substituents independently selected from W, and benzyl optionally substituted with 1 to 3 substituents independently selected from W;

$R^{18}$ is H;

X is O;

$X^1$ is selected from the group Cl, $OR^6$, $SR^6$ and $N(CH_3)_2$;

$R^{15}$ selected from the group $C_1$–$C_4$ alkyl, $C_1$–$C_2$ haloalkyl, $C_3$–$C_4$ alkenyl and propargyl;

$R^{16}$ is selected from H and $CH_3$;

W is selected from the group Cl, F, Br, CN, $CF_3$, $C_1$–$C_2$ alkyl, $C_1$–$C_2$ alkoxy, $OCF_2H$, $OCF_3$ and $NO_2$;

Z is —$CH_2CH_2CH_2$— or —$CH_2CH_2$—;

m is 1 or 2; and n is 1 or 2.

3. A compound according to claim 2 wherein: G is G-9.

4. A compound according to claim 3 where $R^3$ is pyridyl.

5. A compound according to claim 1 of Formula I.

6. A Compound according to claim 5 wherein Q is Q-1.

7. An arthropodicidal composition comprising an arthropodicidally effective amount of a compound according to any one of claims 2 to 6 and 1 and a carrier therefor.

8. A method for controlling arthropods comprising applying to them or to their environment an arthropodicidally effective amount of a compound according to any one of claims 2 to 6 and 1.

* * * * *

UNITED STATES PATENT AND TRADEMARK OFFICE
CERTIFICATE OF CORRECTION

PATENT NO. : 5,474,998
DATED : 12/12/95
INVENTOR(S) : Charles R. Harrison et al.

It is certified that error appears in the above-identified patent and that said Letters Patent is hereby corrected as shown below:

Column 124, line 9, change "-6OCH$_2$O-" to read --6--.

Column 124, line 16, insert the word --optionally-- before the word "containing".

Column 124, line 10, insert --OCH$_2$O--, at the beginning of the line, as the beginning of the paragraph.

Signed and Sealed this

Eleventh Day of February, 1997

Attest:

BRUCE LEHMAN

*Attesting Officer*  *Commissioner of Patents and Trademarks*